(12) United States Patent
Carroll et al.

(10) Patent No.: US 8,846,730 B2
(45) Date of Patent: *Sep. 30, 2014

(54) COMPOUNDS AS CANNABINOID RECEPTOR LIGANDS

(75) Inventors: William A. Carroll, Evanston, IL (US); Michael J. Dart, Highland Park, IL (US); Jennifer M. Frost, Grayslake, IL (US); Teodozyj Kolasa, Lake Villa, IL (US); Tongmei Li, Lake Bluff, IL (US); Bo Liu, Waukegan, IL (US); Arturo Perez-Medrano, Grayslake, IL (US); Meena Patel, Green Oaks, IL (US); Xueqing Wang, Evanston, IL (US); Sridhar Peddi, Grayslake, IL (US)

(73) Assignee: AbbVie Inc., North Chicago, IL (US)

( * ) Notice: Subject to any disclaimer, the term of this patent is extended or adjusted under 35 U.S.C. 154(b) by 408 days.

This patent is subject to a terminal disclaimer.

(21) Appl. No.: 12/554,445

(22) Filed: Sep. 4, 2009

(65) Prior Publication Data

US 2010/0063022 A1 Mar. 11, 2010

Related U.S. Application Data

(60) Provisional application No. 61/095,000, filed on Sep. 8, 2008, provisional application No. 61/224,205, filed on Jul. 9, 2009.

(51) Int. Cl.
*A61K 31/426* (2006.01)
*C07D 277/08* (2006.01)

(52) U.S. Cl.
USPC ........... 514/371; 548/146; 548/190; 548/195; 514/365

(58) Field of Classification Search
USPC ........... 548/146, 190, 193, 195; 514/365, 371
See application file for complete search history.

(56) References Cited

U.S. PATENT DOCUMENTS

| | | | |
|---|---|---|---|
| 3,843,683 A | 10/1974 | Bell | |
| 3,928,327 A | 12/1975 | Takamizawa et al. | |
| 4,885,295 A | 12/1989 | Bell | |
| 4,966,828 A | 10/1990 | Doenges et al. | |
| 4,973,587 A | 11/1990 | Ward et al. | |
| 4,978,664 A | 12/1990 | Bell | |
| 5,013,837 A | 5/1991 | Ward et al. | |
| 5,055,579 A | 10/1991 | Pawlowski et al. | |
| 5,250,498 A | 10/1993 | Andree et al. | |
| 5,468,722 A | 11/1995 | Shibata et al. | |
| 5,530,019 A | 6/1996 | Okada et al. | |
| 5,654,322 A | 8/1997 | Hirata et al. | |
| 6,323,214 B1 | 11/2001 | Baraldi | |
| 6,358,992 B1 | 3/2002 | Pamukcu et al. | |
| 6,369,052 B1 | 4/2002 | Kellar et al. | |
| 6,559,186 B1 | 5/2003 | Campbell | |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 7,560,456 B2 | 7/2009 | Araki et al. | |
| 7,560,481 B2 | 7/2009 | Frost et al. | |
| 7,674,912 B2 * | 3/2010 | Sams et al. | 548/195 |
| 7,683,084 B2 | 3/2010 | Faghih et al. | |
| 7,750,039 B2 | 7/2010 | Frost et al. | |
| 7,868,038 B2 | 1/2011 | Nelson et al. | |
| 7,872,006 B2 * | 1/2011 | Moritani et al. | 514/236.5 |
| 7,872,033 B2 * | 1/2011 | Carroll et al. | 514/372 |
| 7,875,639 B2 * | 1/2011 | Florjancic et al. | 514/367 |
| 7,875,640 B2 | 1/2011 | Kolasa et al. | |
| 7,985,768 B2 | 7/2011 | Nelson et al. | |
| 8,044,071 B2 | 10/2011 | Carroll | |
| 8,058,293 B2 | 11/2011 | Kolasa et al. | |
| 8,158,663 B2 | 4/2012 | Carroll et al. | |
| 8,173,687 B2 | 5/2012 | Carroll et al. | |

(Continued)

FOREIGN PATENT DOCUMENTS

| | | |
|---|---|---|
| CA | 2587667 A1 | 5/2006 |
| DE | 1522361 A1 | 7/1969 |

(Continued)

OTHER PUBLICATIONS

Dart et al (2007): STN International HCAPLUS database, Columbus (OH), accession No. 2007: 1396538.*

(Continued)

*Primary Examiner* — Golam M M Shameem

(74) *Attorney, Agent, or Firm* — Lisa V. Mueller; Michael Best & Friedrich LLP

(57) ABSTRACT

The present application relates to cannabinoid receptor ligands of formula (I)

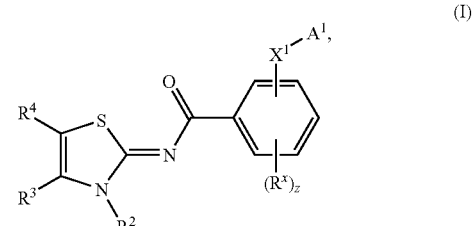

wherein $X^1$, $A^1$, $R^x$, $R^2$, $R^3$, $R^4$, and z are as defined in the specification. The present application also relates to compositions comprising such compounds, and methods for treating conditions and disorders using such compounds and compositions.

22 Claims, No Drawings

(56) References Cited

U.S. PATENT DOCUMENTS

| | | |
|---|---|---|
| 8,236,822 B2 | 8/2012 | Wang et al. |
| 8,288,428 B2 | 10/2012 | Wang et al. |
| 8,338,467 B2 | 12/2012 | Kolasa et al. |
| 8,481,574 B2 | 7/2013 | Meyer et al. |
| 8,492,371 B2 | 7/2013 | Carroll et al. |
| 8,501,794 B2 | 8/2013 | Carroll et al. |
| 8,586,596 B2 | 11/2013 | Dart et al. |
| 2004/0023862 A1 | 2/2004 | Smart et al. |
| 2004/0029040 A1 | 2/2004 | Watanabe et al. |
| 2004/0034090 A1 | 2/2004 | Barth et al. |
| 2004/0077617 A1 | 4/2004 | Bennani et al. |
| 2004/0166539 A1 | 8/2004 | Akhavan-Tafti et al. |
| 2004/0259912 A1 | 12/2004 | Matsumoto et al. |
| 2005/0176713 A1 | 8/2005 | Freyne et al. |
| 2006/0199817 A1 | 9/2006 | Tasker et al. |
| 2007/0061360 A1 | 3/2007 | Holcombe et al. |
| 2007/0155738 A1 | 7/2007 | Steeneck et al. |
| 2008/0058335 A1 | 3/2008 | Florjancic et al. |
| 2008/0058355 A1 | 3/2008 | Westheim et al. |
| 2008/0139635 A1 | 6/2008 | Martin et al. |
| 2008/0242654 A1 | 10/2008 | Kolasa et al. |
| 2008/0287510 A1 | 11/2008 | Carroll et al. |
| 2008/0312435 A1 | 12/2008 | Saito et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105305 A1 | 4/2009 | Butlin et al. |
| 2009/0105306 A1 | 4/2009 | Carroll et al. |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2010/0041720 A1 | 2/2010 | Carroll et al. |
| 2010/0069348 A1 | 3/2010 | Carroll et al. |
| 2010/0069349 A1 | 3/2010 | Carroll et al. |
| 2010/0093814 A1 | 4/2010 | Florjancic et al. |
| 2010/0216760 A1 | 8/2010 | Frost |
| 2011/0065685 A1 | 3/2011 | Frost et al. |
| 2011/0082116 A1 | 4/2011 | Carroll et al. |
| 2011/0086832 A1 | 4/2011 | Kolasa et al. |
| 2011/0086838 A1 | 4/2011 | Nelson et al. |

FOREIGN PATENT DOCUMENTS

| | | | |
|---|---|---|---|
| DE | 1772867 A1 | 6/1971 | |
| DE | 2458933 A1 | 6/1975 | |
| DE | 3533331 A1 | 3/1987 | |
| EP | 412404 A2 | 2/1991 | |
| EP | 568096 A1 | 11/1993 | |
| EP | 0619316 A1 | 10/1994 | |
| EP | 0639569 A1 | 2/1995 | |
| EP | 1060734 A2 | 12/2000 | |
| EP | 1219612 A1 | 7/2002 | |
| EP | 1300401 A1 | 4/2003 | |
| EP | 1640369 A1 | 3/2006 | |
| EP | 1820504 A1 | 8/2007 | |
| FR | 2796643 A1 | 1/2001 | |
| JP | S57171986 A | 10/1982 | |
| JP | 6345736 A | 12/1994 | |
| WO | WO9507271 A1 | 3/1995 | |
| WO | WO-9531448 A1 | 11/1995 | |
| WO | WO-9601591 A1 | 1/1996 | |
| WO | WO-9700860 A1 | 1/1997 | |
| WO | WO9710223 A1 | 3/1997 | |
| WO | WO-0063207 A1 | 10/2000 | |
| WO | WO-0116138 A1 | 3/2001 | |
| WO | WO-0128557 A1 | 4/2001 | |
| WO | WO-0155139 A1 | 8/2001 | |
| WO | WO-0155140 A1 | 8/2001 | |
| WO | WO-0183422 A1 | 11/2001 | |
| WO | WO-0242269 A1 | 5/2002 | |
| WO | WO-02060447 A1 | 8/2002 | |
| WO | WO-02102232 A2 | 12/2002 | |
| WO | WO-03049741 A1 | 6/2003 | |
| WO | WO-03097605 A1 | 11/2003 | |
| WO | WO-2004050086 A1 | 6/2004 | |
| WO | WO-2004110453 A1 | 12/2004 | |
| WO | WO-2005023818 A2 | 3/2005 | |
| WO | WO2005058887 A1 | 6/2005 | |
| WO | WO-2005075464 A1 | 8/2005 | |
| WO | WO2005099353 A2 | 10/2005 | |
| WO | WO-2005099353 A3 | 10/2005 | |
| WO | WO-2005115972 A1 | 12/2005 | |
| WO | WO-2005115986 A1 | 12/2005 | |
| WO | WO 2006008754 A1 | 1/2006 | |
| WO | WO2006051704 A1 | 5/2006 | |
| WO | WO-2006051704 A1 | 5/2006 | |
| WO | WO-2006070106 A1 | 7/2006 | |
| WO | WO2006100208 A1 | 9/2006 | |
| WO | WO-2007061360 A2 | 5/2007 | |
| WO | WO2007140385 A2 | 12/2007 | |
| WO | WO2007140439 A2 | 12/2007 | |
| WO | WO2007140439 A3 | 1/2008 | |
| WO | WO2007140385 A3 | 2/2008 | |
| WO | WO-2008063781 A2 | 5/2008 | |
| WO | WO2008079687 A1 | 7/2008 | |
| WO | WO-2008121558 A1 | 10/2008 | |
| WO | WO-2008130953 A2 | 10/2008 | |
| WO | WO2008144360 A1 | 11/2008 | |
| WO | WO-2009009550 A1 | 1/2009 | |
| WO | WO2009048936 A1 | 4/2009 | |
| WO | WO2009067613 A1 | 5/2009 | |
| WO | WO2009114566 A1 | 9/2009 | |
| WO | WO-2010019547 A1 | 2/2010 | |
| WO | WO-2010033543 A2 | 3/2010 | |
| WO | WO-2010054024 A2 | 5/2010 | |
| WO | WO-2010071783 A1 | 6/2010 | |
| WO | WO-2010111573 A1 | 9/2010 | |
| WO | WO-2010111574 A1 | 9/2010 | |

OTHER PUBLICATIONS

Florjancic et al (2010): STN International HCAPLUS database, Columbus (OH), accession No. 2010: 478868.*

Arevalo-Martin A. et al., "Therapeutic Action of Cannabinoids in a Murine Model of Multiple Sclerosis," Journal of Neuroscience, 2003, vol. 23 (7), pp. 2511-2516.

Benito C. et al., "Cannabinoid CB2 Receptors and Fatty Acid Amide Hydrolase Are Selectively Overexpressed in Neuritic Plaque-Associated Glia in Alzheimer's Disease Brains," Journal of Neuroscience, 2003, vol. 23 (35), pp. 11136-11141.

Bennett et al. "A peripheral mononeuropathy in rat that produces disorders of pain sensation like those seen in man", Pain, 1988, 33, 87-107.

Berge S. M., et al., "Pharmaceutical Salts," J Pharmaceutical Sciences, 1977, 66 (1), 1-19.

Blagojevic N., et al., "Role of heavy water in Boron Neutron Capture Therapy," in Topics in Dosimetry & Treatment Planning for Neutron Capture Therapy, Advanced Medical Publishing, Madison, WI, 1994, 125-134.

Blake et al., "Studies with deuterated drugs," J. Pharm. Sci., 1975, 64 (3), 367-391.

Bouchard J. F et al., "Contribution of endocannabinoids in the endothelial protection afforded by ischemic preconditioning in the isolated rat heart," Life Sciences, 2003, vol. 72, pp. 1859-1870.

Boyle W. J. et al., "Osteoclast differentiation and activation," Nature, 2003, vol. 423, pp. 337-342.

Brennan T. J. et al., "Characterization of a rat model of incisional pain," Pain, 1996, vol. 64, pp. 493-501.

Brickner S. J., et al., "Synthesis and antibacterial activity of U-100592 and U-100766, two oxazolidinone antibacterial agents for the potential treatment of multidrug-resistant gram-positive bacterial infections," J Med Chem., 1996, 39 (3), 673-679.

Buckley N. E. et al., "Immunomodulation by cannabinoids is absent in mice deficient for the cannabinoid CB receptor," European Journal of Pharmacology, 2000, vol. 396, pp. 141-149.

(56) References Cited

OTHER PUBLICATIONS

Carlisle S. J. et al., "Differential expression of the CB2 cannabinoid receptor by rodent macrophages and macrophage-like cells in relation to cell activation," International Immunopharmacology, 2002, vol. 2, pp. 69.
Carrier E. J. et al., "Endocannabinoids in Neuroimmunology and Stress," Current Drug Targets CNS & Neurological Disorders, 2005, vol. 4, pp. 657-665.
Casanova M. L. et al., "Inhibition of skin tumor growth and angiogenesis in vivo by activation of cannabinoid receptors," Journal of Clinical Investigation, 2003, vol. 111, pp. 43-50.
Chaplan S. R. et al., "Quantitative assessment of tactile allodynia in the rat paw," Journal of Neuroscience Methods, 1994, vol. 53, pp. 55-63.
Cichewicz D. L. et al., "Synergistic interactions between cannabinoid and opioid analgesics," Life Sciences, 2004, vol. 74, pp. 1317-1324.
Clayton N., et al., "CB1 and CB2 cannabinoid receptors are implicated in inflammatory pain," Pain, 2002, vol. 96, pp. 253-260.
Czajka D. M., "Effect of deuterium oxide on the reproductive potential of mice," Ann NY Acad Sci, 1960, vol. 84, pp. 770-779.
Czajka D.M., et al., "Physiological effects of deuterium on dogs," Am. J. Physiol., 1961, 201 (2), 357-362.
Dixon W. J. et al., "Efficient analysis of experimental observations," Annual Review of Pharmacology and Toxicology, 1980, vol. 20, pp. 441-462.
Filippo C. D. et al., "Cannabinoid CB2 receptor activation reduces mouse myocardial ischemic-reperfusion injury: involvement of cytokine/chemokines and PMN," Journal of Leukocyte Biology, 2004, vol. 75, pp. 453-459.
Foster, A.B., et al., "Deuterium Isotope Effects in the Metabolism of Drugs and Xenobiotics: Implications for Drug Design," Advances in Drug Research, 1985, 14, Academic Press, London, 2-36.
Galiégue et al., "Expression of central and peripheral cannabinoid receptors in human immune tissues and leukocyte subpopulations," European Journal of Biochemistry, 1995, vol. 232, pp. 54-61.
Greene T.W., et al., "Protection for the Amino group," Protective Groups in Organic Synthesis, 1999, Edition 3, John Wiley & Sons, 494-653.
Grotenhermen F. et al., "IACM 2nd Conference on Cannabinoids in Medicine," Expert Opinion in Pharmacotherapy, 2003, vol. 4 (12), pp. 2367-2371.
Hanus L. et al., "HU-308: A specific agonist for CB 2, a peripheral cannabinoid receptor," Proceedings of the National Academy of Science, 1999, vol. 96, pp. 14228-14233.
Hohmann A. G. et al., "Selective Activation of Cannabinoid CB2 Receptors Suppresses Hyperalgesia Evoked by Intradermal Capsaicin," Journal of Pharmacology and Experimental Therapeutics, 2004, vol. 308, pp. 446-453.
Ibrahim M. M. et al., "Activation of CB2 cannabinoid receptors by AM1241 inhibits experimental neuropathic pain: Pain inhibition by receptors not present in the CNS," Proceedings of the National Academy of Science, 2003, vol. 100 (18), pp. 10529-10533.
Ibrahim M. M. et al., "CB2 cannabinoid receptor activation produces antinociception by stimulating peripheral release of endogenous opioids," Proceedings of the National Academy of Science, 2005, vol. 102 (8), pp. 3093-3098.
Ihenetu K. et al., "Inhibition of interleukin-8 release in the human colonic epithelial cell line HT-29 by cannabinoids," European Journal of Pharmacology, 2003, vol. 458, pp. 207-215.
IUPAC Commission on Nomenclature of Organic Chemistry: Rules for the Nomenclature of Organic Chemistry Section E: Stereochemistry, Pure Appl Chem, 1976, 45, 11-30.
Joshi S. K., et al., "Comparison of Antinociceptive Actoins of Standard Analgesics in Attenuating Capsaicin and Nerve-Injury-Induced Mechanical Hypersensitivty," Neurosci, 2006, vol. 143, pp. 587-596.
Julien B et al., "Antifibrogenic Role of the Cannabinoid Receptor CB2 in the Liver," Gastroenterology, 2005, vol. 128, pp. 742-755.
Karsak M. et al., "Cannabinoid receptor type 2 gene is associated with human osteoporosis," Human Molecular Genetics, 2005, vol. 14 (22), pp. 3389-3396.

Kato et al., "Synthesis of Deuterated Mosapride Citrate," J. Labelled Comp. Radiopharmaceut, 1995, 36 (10), 927-932.
Kim S. H. et al., "An experimental model for peripheral neuropathy produced by segmental spinal nerve ligation in the rat," Pain, 1992, vol. 50 (3), pp. 355-363.
Kushner et al., "Pharmacological uses and perspectives of heavy water and deuterated compounds," Can J Physiol Pharmacol, 1999, vol. 77, pp. 79-88.
Lepicier P. et al., "Endocannabinoids protect the rat isolated heart against ischaemia," British Journal of Pharmacology, 2003, vol. 139, pp. 805-815.
Lizondo J., et al., "Linezolid: Oxazolidinone antibacterial," Drugs of the Future, 1996, 21 (11), 1116-1123.
Lotersztajn S. et al., "Hepatic Fibrosis: Molecular Mechanisms and Drug Targets," Annual Review of Pharmacology and Toxicology, 2005, vol. 45, pp. 605-628.
Malan T. P. et al., "CB2 cannabinoid receptor-mediated peripheral antinociception," Pain, 2001, vol. 93, pp. 239-245.
Mallesham B., et al., "Highly efficient Cul-catalyzed coupling of aryl bromides with oxazolidinones using Buchwald's protocol: a short route to linezolid and toloxatone," Org. Lett., 2003, 5 (7), 963-965.
Maresz K. et al., "Modulation of the cannabinoid CB2 receptor in microglial cells in response to inflammatory stimuli," Journal of Neurochemistry, 2005, vol. 95, pp. 437-445.
Mathison R. et al., "Effects of cannabinoid receptor-2 activation on accelerated gastrointestinal transit in lipopolysaccharide-treated rats," British Journal of Pharmacology, 2004, vol. 142, pp. 1247-1254.
McKallip R. J., et al., "Targeting CB2 cannabinoid receptors as a novel therapy to treat malignant lymphoblastic disease," Blood, 2002, vol. 15 (2), pp. 627-634.
Nackley A. G. et al., "Selective activation of cannabinoid CB2 receptors suppresses spinal fos protein expression and pain behavior in a rat model of inflammation," Neuroscience, 2003, vol. 119, pp. 747-757.
Ni X. et al., "Win 55212-2, a cannabinoid receptor agonist, attenuates leukocyte/endothelial interactions in an experimental autoimmune encephalomyelitis model," Multiple Sclerosis, 2004, vol. 10, pp. 158-164.
Patel J. J. et al., "Inhibition of guinea-pig and human sensory nerve activity and the cough reflex in guinea-pigs by cannabinoid (CB2) receptor activation," British Journal of Pharmacology, 2003, vol. 140, pp. 261-268.
PCT international partial search report for application No. PCT/US2009/056179 mailed on Nov. 23, 2009, 1 page.
Pertwee R. G., "Cannabinoids and multiple sclerosis," Pharmacology & Therapeutics, 2002, vol. 95, pp. 165-174.
Prescott et al., "Lipid Vesicles as Carriers for Introducing Biologically Active Materials into Cells," Methods in Cell Biology, 1976, Academic Press, 33-71.
Quartilho A. et al., "Inhibition of Inflammatory Hyperalgesia by Activation of Peripheral CB2 Cannabinoid Receptors," Anesthesiology, 2003, vol. 99, pp. 955-960.
Ralston S. H., "Regulation of bone mass, bone loss and osteoclast activity by cannabinoid receptors," Nature Medicine, 2005, vol. 11, pp. 774-779.
Ramirez B. G. et al., "Prevention of Alzheimer's Disease Pathology by Cannabinoids: Neuroprotection Mediated by Blockade of Microglial Activation," Journal of Neuroscience, 2005, vol. 25 (8), pp. 1904-1913.
Sanchez C. et al., "Inhibition of Glioma Growth in Vivo by Selective Activation of the CB2 Cannabinoid Receptor1," Cancer Research, 2001, vol. 61, pp. 5784-5789.
Steffens S. et al., "Low dose oral cannabinoid therapy reduces progression of atherosclerosis in mice," Nature, 2005, vol. 434, pp. 782-786.
Thomson J. F., "Physiological effects of D20 in mammals," Ann. New York Acad. Sci., 1960, 84, 736-744.
Valenzano K. J. et al., "Pharmacological and pharmacokinetic characterization of the cannabinoid receptor 2 agonist, GW405833, utilizing rodent models of acute and chronic pain, anxiety, ataxia and catalepsy," Neuropharmacology, 2005, vol. 48, pp. 658-672.

(56) References Cited

OTHER PUBLICATIONS

Warhurst A. C. et al., "Interferon gamma induces differential upregulation of alpha and beta chemokine secretion in colonic epithelial cell lines," Gut, 1998, vol. 42, pp. 208-213.
Williams P. D., et al., "Renin inhibitors containing conformationally restricted P1-P1 dipeptide mimetics", J. Med. Chem., 1991, 34, pp. 887-900. , Journal of Medicinal Chemistry, 1991, vol. 34, pp. 887-900.
Wright K. et al., "Differential Expression of Cannabinoid Receptors in the Human Colon: Cannabinoids Promote Epithelial Wound Healing," Gastroenterology, 2005, vol. 129, pp. 437-453.
Yoshihara S. et al., "Cannabinoid Receptor Agonists Inhibit Sensory Nerve Activation in Guinea Pig Airways," American Journal of Respiratory and Critical Care Medicine, 2004, vol. 170, pp. 941-946.
Yoshihara S. et al., "Endogenous Cannabinoid Receptor Agonists Inhibit Neurogenic Inflammations in Guinea Pig Airways," Allergy and Immunology, 2005, vol. 138, pp. 80-87.
Yoshihara S. et al., "The Cannabinoid Receptor Agonist WIN 55212-2 Inhibits Neurogenic Inflammations in Airway Tissues," Journal of Pharmacological Sciences, 2005, vol. 98 (1), pp. 77-82.
Abreo, et al., "Novel 3-Pyridyl Ethers with Subnanomolar Affinity for Central Neuronal Nicotonic Acetylcholine Receptors," Journal of Medicinal Chemistry, 1996, vol. 39 (4), pp. 817-825.
Ambartsumova, et al., "Effect of Various Factors on the Reaction of 2-Aminobenzothiazoles with Propylene Oxide," Chemistry of Heterocyclic Compounds, 2002, vol. 38 (8), pp. 994-999.
Araki, et al., (2003): STN International HCAPLUS database, (Columbus, OH). Accession No. 2003-931334.
Baker, et al., "Regiospecific Vinyl Phosphate/β-Keto Phosphonate Rearrangements Initiated by Halogen-Metal Exchange," Journal of Organic Chemistry, 1998, vol. 63 (8), pp. 2613-2618.
Benito, et al., "A Glial Endogenous Cannabinoid System is Upregulated in the Brains of Macaques with Simian Immunodeficiency Virus-Induced Encephalitis," Journal of Neuroscience, 2005, vol. 25 (10), pp. 2530-2536.
Beylot, et al., "In Vivo Studies of Intrahepatic Metabolic Pathways," Diabetes Metabolism, 1997, vol. 23 (3), pp. 251-257.
Bozidar, et al., "Transformations of 1,2,4-Thiadiazolo/2,3-X/ Azines," Heterocycles, 1987, vol. 26 (3), pp. 689-697.
Bozidar, et al., "Transformations of 1-(2-Chloropyridyl-3)-4-ethoxycarbonyland 1-(2-Chloropyridyl-3)-4-ethoxycarbonylmethyl Thiosemicarbazides. Attempts to Prepare Pyrido [3,2-e]-1,2,4-thiadiazine," Monatshefte Fur Chemie, 1988, vol. 119, pp. 333-339.
CAPLUS Record of U.S. Patent Application Publication No. 2008/0058335 by Westheim, et al., 2007.
CAPLUS Record of U.S. Patent Application Publication No. 2008/0242654 by Kolasa, et al., 2008.
Dart, et al., (2007): STN International HCAPLUS database, Columbus (OH), Accession No. 2007:1396538.
Final Office Action mailed Dec. 28, 2011 for U.S. Appl. No. 12/639,173, filed Sep. 16, 2009.
Final Office Action mailed Mar. 10, 2010 for U.S. Appl. No. 11/755,434 filed May 30, 2007.
Final Office Action mailed Feb. 15, 2011 for U.S. Appl. No. 12/120,969, filed on May 15, 2008.
Final Office Action mailed Mar. 24, 2011 for U.S. Appl. No. 11/755,434, filed May 30, 2007.
Florjancic, et al (2009): Caplus Entry for WO2009067613, Accession No. 2009:649814.
Florjancic, et al (2010): STN International HCAPLUS database, Columbus (OH), Accession No. 2010:478868.
Giron, D., "Applications of Thermal Analysis and Coupled Techniques in Pharmaceutical Industry," Journal of Thermal Analysis and Calorimetry, 2002, vol. 68, pp. 335-357.
Giron, D., "Investigations of Polymorphism and Pseudo-Polymorphism in Pharmaceuticals by Combined Thermoanalytical Techniques," The Journal of Thermal Analysis and Calorimetry, 2001, vol. 64, pp. 37-60.
Golech, et al., "Human Brain Endothelium: Coexpression and Function of Vannilloid and Endocannabinoid Receptors," Molecular Brain Research, 2004, vol. 132 (1), pp. 87-92.
Golub, et al., "Molecular Classification of Cancer: Class Discovery and Class Prediction by Gene Expression Monitoring," Science, 1999, vol. 286 (5439), pp. 531-537.
Gouldson, et al., "Mutational Analysis and Molecular Modeling of the Antagonist SR144528 Binding Site on the Human Cannabinoid CB2 Receptor; Figures 4 and 5," European Journal of Pharmacology, 2000, vol. 401 (1), pp. 17-25.
Hargreaves, et al., "A New and Sensitive Method for Measuring Thermal Nociception in Cutaneous Hyperalgesia," Pain, 1988. 32 (1), pp. 77-88.
International Search Report for Application No. PCT/US07/069921, mailed on Nov. 27, 2007, 4 pages.
International Search Report for Application No. PCT/US08/063648, mailed on Aug. 13, 2008, 3 pages.
International Search Report for Application No. PCT/US2009/056179, mailed on Jun. 9, 2010, 4 pages.
International Search Report for Application No. PCT/US2009/057088, mailed on Oct. 5, 2010, 4 pages.
International Search Report for Application No. PCT/US2009/068173, mailed on Feb. 5, 2010, 3 pages.
Kreutzberg, et al., "Microglia: A Sensor for Pathological Events in the CNS," Trends in Neuroscience, 1996, vol. 19, pp. 312-318.
Li, et al., "An Improved Synthesis of Pyran-3,5-Dione: Application to the Synthesis of Abt-598, A Potassium Channel Opener, Via Hantzsch Reaction," Journal of Organic Chemistry, 2006, vol. 71 (4), pp. 1725-1727.
Maligres, et al., "Stereocontrolled Preparation of a Nonpeptidal (−)-Spirobicyclic NK-1 Receptor Antagonist," Journal of Organic Chemistry, 2002, vol. 67 (4), pp. 1093-1101.
Manaka, et al., "2-Acylimino-3H-thiazoline Derivatives: A Novel Template for Platelet GPIIb/IIIa Receptor Antagonists," Bioorganic & Medicinal Chemistry Letters, 2001, vol. 11, pp. 1031-1035.
Molina-Holgado, et al., "Endogenous Interleukin-1 Receptor Antagonist Mediates Anti-Inflammatory and Neuroprotective Actions of Cannabinoids in Neurons and Glia," Journal of Neuroscience, 2003, vol. 23 (16), pp. 6470-6474.
Non-Final Office Action mailed Jun. 2, 2009 for U.S. Appl. No. 11/755,434, filed May 30, 2007.
Non-Final Office Action mailed May 17, 2011 for U.S. Appl. No. 12/560,893, filed Sep. 16, 2009.
Non-Final Office Action mailed Jun. 29, 2010 for U.S. Appl. No. 11/755,434, filed May 30, 2007.
Non-Final Office Action mailed Nov. 30, 2010 for U.S. Appl. No. 11/755,434, filed May 30, 2007.
Nunez, et al., "Cannabinoid CB2 Receptors Are Expressed by Perivascular Microglial Cells in the Human Brain: An Immunohistochemical Study," Synapse, 2004, vol. 53, pp. 208-213.
Ohta, et al., "N-Alkyidenearylcarboxamides as a new Potent and Selective CB2 Cannabinoid Receptor Agonist with an Analgesic Action," Bioorganic and Medicinal Chemistry Letters, 2007, vol. 17 (22), pp. 6299-6304.
Opposition filed by "Asociacion de Industrias Farmaceuticas Dominicanas Inc" for the Dominican Patent application Nr P2008-0060, received on Apr. 1, 2009, 8 pages.
Poste, et al., "Lipid Vesicles as Carriers for Introducing Biologically Active Materials into Cells," Methods in Cell Biology, 1976, vol. 14, pp. 33-71.
Radulescu, et al., "Actes Du Colloque Franco-Roumain De Chimie Appliquee, 3Rd, Bacau, Romania," 2004, pp. 117-120.
Radulescu, et al., "Synthesis and Characteristics of Compact Condensed Heterocyclic System 2-Aminothiazolo[5,4-c]Pyridine," Revista de Chimie, 2004, vol. 55 (11), pp. 889-893.
Radulescu, et al., "The Comparative Study on the Synthesis Methods of a Heterocyclic System 2-Aminothiazolo[4,5-13]Pyricline," Revista de Chimie, 2005, vol. 56 (6), pp. 659-662.
Rautio, et al, "Prodrugs: Design and Clinical Applications," Nature Reviews Drug Discovery, 2008, vol. 7 (3), pp. 255-270.
Rodriquez-Spong, et al., "General Principles of Pharmaceutical Solid Polymorphism: A Supramolecular Perspective," Advanced Drug Delivery Reviews, 2004, vol. 56 (3), pp. 241-274.

(56) References Cited

OTHER PUBLICATIONS

Ross, et al., "Antianaphylactic agents. 1. 2-(Acylamino)oxazoles," Journal of Medicinal Chemistry, 1979, vol. 22(4), pp. 412-417.
Shilpi, et al., "The Synthesis and Antimicrobial Screening of Some Novel Aza-Imidoxy Compounds as Potential Chemotherapeutic Agents," Phosphorus Sulfur and Silicon, 2006, vol. 181 (7), pp. 1665-1673.
Smith, D., "Do Prodrugs Deliver?" Current Opinion in Drug Discovery and Development, 2007, vol. 10 (5), 550-559.
Souillac, et al, "Characterization of Delivery Systems, Differential Scanning Calorimetry," Encyclopedia of Controlled Drug Delivery, 1999, pp. 217-218.
Testa, B., "Prodrugs: Bridging Pharmacodynamic/Pharmacokinetic Gaps," Current Opinion in Chemical Biology, 2009, vol. 13 (3), pp. 338-344.
Walter, et al., "Cannabinoids and Neuroinflammation," British Journal of Pharmacology, 2004, vol. 141 (5), pp. 775-785.
Wang, et al., Drug Delivery: Principles and Applications, John Wiley & Sons, Inc., 2005, pp. 136-137.
Watkins, et al., "Glial Activation: A Driving Force for Pathological Pain," Trends in Neuroscience, 2001, vol. 24 (8), pp. 450-455.
Werbel, et al., "1-Alkyl-3-(3-alkyl-5-nitro-4-thiazolin-2-ylidene)ureasa nd Related Compounds as Schistosomicides," Journal of Medicinal Chemistry, 1972, vol. 15 (9), pp. 955-963.
Weyer, et al., "Blutzuckersenkende Chinolin-8-Carboxamidoalkyl-Benzol Sulfonamid Derivate," Arzneimittel-Forschung, 1974, vol. 24 (3), pp. 269-275.
Widdowson, et al., "Palladium Catalysed Suzuki Reactions of Fluoroarenes," Chemical Communication (Camb), 2003, vol. 5, pp. 578-579.
Zimmer, et al., "Increased Mortality, Hypoactivity, and Hypoalgesia in Cannabinoid CB1 Receptor Knockout Mice," Proceedings of the National Academy of Science, 1999, vol. 96 (10), pp. 5780-5785.
Final Office Action mailed Mar. 14, 2014 for U.S. Appl. No. 12/970,480, filed Dec. 16, 2010.
Notice of Allowance mailed Apr. 14, 2014 for U.S. Appl. No. 12/967,282, filed Dec. 14, 2010.
Notice of Allowance mailed Jan. 17, 2014 for U.S. Appl. No. 12/120,969, filed May 15, 2008.
Non-Final Rejection mailed Dec. 5, 2013 for U.S. Appl. No. 12/967,282, filed Dec. 14, 2010.
Office Action mailed Nov. 15, 2013 for European Application No. 05855099.7 filed Dec. 21, 2005.
Alfaro I., et al., "Dihydroaromatic Compounds in the Diels-Alder Reaction—III: In Situ Generation and Diels-Alder Reaction of Cyclohexa-1,3-Dienes," Tetrahedron, 1970, vol. 26, pp. 201-218.
Andreani, et al., "Ring-opened, etc," Collection of Czechoslovak Chemical Communications, 1999, vol. 64, pp. 299-312.
Ansell M.F., et al., "The Synthesis of (+/−)-10a-Homo-11a-CarbathromboxaneA1, a Stable Thromboxane A Analogue," Journal of Chemical Society Perkin Trans, 1984, pp. 1061-1068.
Atwood B.K., et al., "CB: Therapeutic Target-in-Waiting," Progress in Neuro-Psychopharmacology & Biological Psychiatry, 2012, vol. 38 (1), pp. 16-20.
Bacon E.R., et al., "Synthesis of 7-Ethyl-4, 7-dihydro-4-oxo-2-(4-pyridinyl)thieno[2,3-b]pyridine-5-carboxylic Acid," Journal of Heterocyclic Chemistry, 1991, vol. 28, pp. 1953-1955.
Baker T.J., et al., "Regiospecific Vinyl Phosphate/β-Keto Phosphonate Rearrangements Initiated by Halogen-Metal Exchange," Journal of Organic Chemistry, 1998, vol. 63 (8), pp. 2613-2618.
Bartlett P.A., et al., "Chorismate Mutase Inhibitors: Synthesis and Evaluation of Some Potential Transition-State Analogues," Journal of Organic Chemistry, 1988, vol. 53, pp. 3195-3210.
Bermudez-Silva, et al., "Role of Cannabinoid CB2 Receptors in Glucose Homeostasis in Rats," European Journal of Pharmacology, 2007, vol. 565 (1-3), pp. 207-211.
Bruson H.A., et al., "Action of Sulfuric Acid upon Unsaturated Isothiocyanates: Mercaptothiazolines," Journal of American Chemical Society, 2011, vol. 59 (10), pp. 2011-2013.
Cai, et al., Ex Parte Appeal No. 2011005302, decided Jul. 12, 2011.
Campbell V.A., et al., "Alzheimer's Disease; Taking the Edge off with Cannabinoids?," British Journal of Pharmacology, 2007, vol. 152 (5), pp. 655-662.
Caplus Entry for International Application Publication No. WO2008130953, Accessed Aug. 14, 2012, with Structures Relevant to Claim 25 as Filed Aug. 11, 2011.
Caplus Entry for International Application Publication No. WO2008130953, Accessed Aug. 14, 2012, with Structures Relevant to Claim 35 as Filed Aug. 11, 2011.
CAS Registry No. 1061668-81-2, which entered STN on Oct. 15, 2008.
Castejon P., et al., "A Convenient, Stereodivergent Approach to the Enantioselective Synthesis of N-Boc-Aminoalkyl Epoxides," Tetrahedron Letters, 1995, vol. 36 (17), pp. 3019-3022.
Chauhan M.S., "The Reaction of Some Heterocyclic Thiones with Ethyl Azidoformate," Canadian Journal of Chemistry, 1976, vol. 54 (24), pp. 3879-3883.
Chemical Abstracts Accession No. 1030770638, Jun. 26, 2008.
Cotarca L., et al., "Bis (trichloromethyl) Carbonate in Organic Synthesis," 1996, vol. 6, pp. 553-576.
Cross., et al., "Rules for the Nomenclature of Organic Chemistry, Section E: Stereochemistry," International Union of Pure and Applied Chemistry, 1976, vol. 45, pp. 11-30.
Database Registry [Online] Chemical Abstracts Service, Columbus, Ohio, US, Mar. 2, 2008, XP002687516, Database Accession No. 1006022-43-0.
Database Registry [Online] Chemical Abstracts Service, Columbus, Ohio, US, Mar. 2, 2008, XP002687517, Database Accession No. 1005993-02-1.
Database Registry [Online] Chemical Abstracts Service, Columbus, Ohio, US, Mar. 6, 2008, XP002687515, Database Accession No. 1006758-59-3.
Database Registry [Online] Chemical Abstracts Service, Columbus, Ohio, US, Mar. 7, 2008, XP002687514, Database Accession No. 1007004-94-5.
Database Registry [Online] Chemical Abstracts Service, Columbus, Ohio, US, Mar. 10, 2008, XP002687513, Database Accession No. 1007244-89-4.
Database Registry [Online] Chemical Abstracts Service, Columbus, Ohio, US, Feb. 29, 2008, XP002687518, Database Accession No. 1005931-81-6.
Dauben W.G., et al., "Organic Reactions at High Pressure Cycloadditions with Furans," Journal of the American Chemical Society, 1976, vol. 98 (7), pp. 1992-1993.
Dawood K.M., et al., "Synthesis, Anticonvulsant, and Anti-Inflammatory Evaluation of Some New Benzotriazole and Benzofuran-Based Heterocycles," Bioorganic & Medicinal Chemistry, 2006, vol. 14 (11), pp. 3672-3680.
Dellemijn P.L., et al., "Randomised Double-Blind Active-Placebo-Controlled Crossover Trial of Intravenous Fentanyl in Neuropathic Pain," Lancet, 1997, vol. 349 (9054), pp. 753-758.
DeWolfe R.H., "Reactions of Aromatic Amines with Aliphatic Ortho Esters. A Convenient Synthesis of Alkyl N-Arylimidic Esters," Journal of Organic Chemistry, 1962, vol. 27, pp. 490-493.
Dorsch J.B., et al., "The Preparation of Benzoylacetic Ester and Some of its Homologs," Journal of the American Chemical Society, 1932, vol. 54, pp. 2960-2964.
Ebata et al., "Synthesis of Both Enantiomers of 4-Hexanolide and 4-Dodecanolide," Agriculture Biochemical, 1991, vol. 55 (6), pp. 1685-1686.
Eckert H., et al., "Triphosgene, a Crystalline Phosgene Substitute," Angewandte Chemie International Edition in English, 1987, vol. 26 (9), pp. 894-895.
European Search Report for Application No. EP12187944, mailed on Nov. 20, 2012, 7 pages.
Ex Parte Quayle Action mailed Oct. 12, 2012 for U.S. Appl. No. 13/160,952, filed Jun. 15, 2011.
Fattori D., et al. "The Demjanov and Tiffeneau-Demjanov One-Carbon Ring Enlargements of 2-Aminomethy1-7-Oxabicyclo[2.2.1]Heptane derivatives. The Stereo- and Regioselective Additions of 8-Oxabicyclo[3.2.1]Oct-6-en-2-One to Soft Electrophiles," Tetrahedron, 1993, vol. 49 (8), pp. 1649-1664.

(56) References Cited

OTHER PUBLICATIONS

Final Office Action mailed Oct. 3, 2013 for U.S. Appl. No. 12/246,808, filed Oct. 7, 2008.
Final Office Action mailed Jul. 14, 2011 for U.S. Appl, No. 12/246,808, filed Oct. 7, 2008.
Final Office Action mailed Sep. 14, 2011 for U.S. Appl. No. 12/274,105, filed Nov. 19, 2008.
Final Office Action mailed Feb. 15, 2011 for U.S. Appl. No. 12/120,969, filed May 15, 2008.
Final Office Action mailed Nov. 16, 2011 for U.S. Appl. No. 12/554,445, filed Sep. 4, 2009.
Final Office Action mailed Nov. 16, 2011 for U.S. Appl. No. 12/560,897, filed Sep. 16, 2009.
Final Office Action mailed Apr. 19, 2011 for U.S. Appl. No. 12/539,120, filed Aug. 11, 2009.
Final Office Action mailed Oct. 19, 2011 for U.S. Appl. No. 12/560,893, filed Sep. 16, 2009.
Final Office Action mailed Nov. 21, 2012 for U.S. Appl. No. 12/120,969, filed May 15, 2008.
Final Office Action mailed Apr. 23, 2013 for U.S. Appl. No. 12/967,275, filed Dec. 14, 2010.
Florjancic A., et al (2009): Caplus Entry for WO2009067613, Accession No. 2009:649814.
Goerdeler J., et al., "Uber Isothiazole, VIII. Synthese von Sulfonylamino-isothiazolen und Sulfonyliminoisothiazolinen aus Sulfonylsenfolen," Chemische Berichte, 1969, vol. 102 (7), pp. 2273-2284.
Goodman A.J., et al., "CB2 Selective Sulfamoyl Benzamides; Optimization of the Amide Functionality," Bioorganic & Medicinal Chemistry Letters, 2009, vol. 19 (2), pp. 309-313.
Greene T.W., et al., in: Protective Groups in Organic Synthesis, 3rd Edition, John Wiley and Sons, Inc., 1999, Preface, Table of Contents, Abbreviations.
Hamuro Y., et al., "Solid-Phase Synthesis of Acyclic and Cyclic Amino Acid Derived Urea Peptidomimetics Using Phoxime Resin," The Journal of Combinatorial Chemistry, 1999, vol. 1, pp. 163-172.
Horig H., et al., "From Bench to Clinic and Back: Perspective on the 1st IQPC Translational Research conference," Journal of Translational Medicine, 2004, vol. 2 (44).
Hutchins S.M., et al., "A General Method for the Solid Phase Synthesis of Ureas," Tetrahedron Letters, 1994, vol. 35 (24), pp. 4055-4058.
Hutchins S.M., et al., "A Strategy for Urea Linked Diamine Libraries," Tetrahedron Letters, 1995, vol. 36 (15), pp. 2583-2586.
International Preliminary Report on Patentability and Written Opinion for Application No. PCT/US07/081263, mailed on Apr. 15, 2010, 8 pages.
International Preliminary Report on Patentability and Written Opinion for Application No. PCT/US08/069453, mailed on Jan. 12, 2010, 6 pages.
International Preliminary Report on Patentability and Written Opinion for Application No. PCT/US08/079182, mailed on Apr. 13, 2010, 5 pages.
International Preliminary Report on Patentability and Written Opinion for Application No. PCT/US08/080253, mailed on Apr. 20, 2010, 6 pages.
International Preliminary Report on Patentability and Written Opinion for Application No. PCT/US2005/046480, mailed on Jun. 26, 2007, 8 pages.
International Preliminary Report on Patentability and Written Opinion for Application No. PCT/US2007/0087175, mailed on Jun. 23, 2009, 8 pages.
International Preliminary Report on Patentability and Written Opinion for Application No. PCT/US2007/069921, mailed on Dec. 3, 2008, 10 pages.
International Preliminary Report on Patentability and Written Opinion for Application No. PCT/US2007/070029, mailed on Dec. 3, 2008, 8 pages.
International Preliminary Report on Patentability and Written Opinion for Application No. PCT/US2007/077321, mailed on Mar. 3, 2009, 7 pages.
International Preliminary Report on Patentability and Written Opinion for Application No. PCT/US2008/057460, mailed on Sep. 29, 2009, 11 pages.
International Preliminary Report on Patentability and Written Opinion for Application No. PCT/US2008/060400, mailed on Oct. 20, 2009, 11 pages.
International Preliminary Report on Patentability and Written Opinion for Application No. PCT/US2008/063648, mailed on Nov. 24, 2009, 7 pages.
International Preliminary Report on Patentability and Written Opinion for Application No. PCT/US2008/084216, mailed on May 25, 2010, 5 pages.
International Preliminary Report on Patentability and Written Opinion for Application No. PCT/US2009/053369, mailed on Feb. 15, 2011, 6 pages.
International Preliminary Report on Patentability and Written Opinion for Application No. PCT/US2009/056179, mailed on Mar. 8, 2011, 9 pages.
International Preliminary Report on Patentability and Written Opinion for Application No. PCT/US2009/063318, mailed on May 10, 2011, 5 pages.
International Preliminary Report on Patentability and Written Opinion for Application No. PCT/US2009/068173, mailed on Jun. 21, 2011, 8 pages.
International Preliminary Report on Patentability and Written Opinion for Application No. PCT/US2010/028790, mailed on Sep. 27, 2008, 5 pages.
International Preliminary Report on Patentability for Application No. PCT/US2007/077320, mailed on Mar. 3, 2009, 1 page.
International Preliminary Report on Patentability for Application No. PCT/US2009/036715, mailed on Sep. 14, 2010, 1 page.
International Search Report and Written Opinion for Application No. PCT/US2007/077320, mailed on Feb. 7, 2008, 12 pages.
International Search Report and Written Opinion for Application No. PCT/US2009/036715, mailed on Jun. 10, 2009, 9 pages.
International Search Report for Application No. PCT/US07/070029, mailed on Nov. 30, 2007, 3 pages.
International Search Report for Application No. PCT/US07/081263, mailed on Nov. 27, 2008, 3 pages.
International Search Report for Application No. PCT/US08/057460, mailed on Aug. 20, 2008, 3 pages.
International Search Report for Application No. PCT/US08/060400, mailed on Oct. 17, 2008, 3 pages.
International Search Report for Application No. PCT/US08/069453, mailed on Sep. 25, 2008, 2 pages.
International Search Report for Application No. PCT/US08/079182, mailed on Dec. 15, 2008, 2 pages.
International Search Report for Application No. PCT/US08/080253, mailed on Mar. 3, 2009, 3 pages.
International Search Report for Application No. PCT/US2005/0046480, mailed on Apr. 18, 2006, 5 pages.
International Search Report for Application No. PCT/US2007/0077321, mailed on Feb. 1, 2008, 3 pages.
International Search Report for Application No. PCT/US2007/0087175, mailed on Apr. 8, 2008, 4 pages.
International Search Report for Application No. PCT/US2008/084216, mailed on Feb. 19, 2009, 1 page.
International Search Report for Application No. PCT/US2009/053369, mailed on Oct. 22, 2009, 3 pages.
International Search Report for Application No. PCT/US2009/063318, mailed on May 6, 2010, 3 pages.
International Search Report for Application No. PCT/US2010/028790, mailed Jul. 19, 2010, 3 pages.
International Search Report for Application No. PCT/US2010/028794, mailed Jul. 20, 2010, 3 pages.
International Search Report for Application No. PCT/US2010/028796, mailed Jul. 16, 2010, 4 pages.
International Search Report for Application No. PCT/US2011/040501, mailed on Oct. 24, 2011, 2 pages.

(56) References Cited

OTHER PUBLICATIONS

Izdebski J., et al., "A New Convenient Method for the Synthesis of Symmetrical and Unsymmetrical N,N'-Disubstituted Ureas," Synthesis, 1989, pp. 423-425.
Jasys V.J., et al., "Preparation of Fluoroadamantane Acids and Amines: Impact of Bridgehead Fluorine Substitution on the Solution- and Solid-State Properties of Functionalized Adamantanes," Journal of the American Chemical Society, 2000, vol. 122, pp. 466-473.
Jhaveri M.D., et al., "Cannabinoid CB2 Receptor-Mediated Anti-Nociception in Models of Acute and Chronic Pain," Molecular Neurobiology, 2007, vol. 36 (1), pp. 26-35.
Katritzky A.R., et al., "A General Synthesis of Unsymmetrical Tetrasubstituted Ureas," Journal of Organic Chemistry, 1997, vol. 62 (11), pp. 4155-4158.
Kherjee S., et al., "Species Comparison and Pharmacological Characterization of Rat and Human Cb2 Cannabinoid Receptors," European Journal of Pharmacology, 2004, vol. 505 (1-3), pp. 1-9.
Khusnutdinov R.I., et al., "Chlorination of Adamantane and its Derivatives by Carbon Tetrachloride in the Presence of Manganese-, Vanadium-, and molybdenum-Containing Catalysts," Neftekhimiya, 2004, vol. 44 (2), pp. 148-155.
Knolker H.J., et al., "A Novel Method for the Synthesis of Isocyanates Under Mild Conditions," Angewandte Chemie International Edition in English, 1995, vol. 34 (22), pp. 2497-2500.
Knolker H.J., et al., "Synthesis of Symmetrical and Unsymmetrical Ureas by DMAP-Catalyzed Reaction of Alkyl- and Arylamines with Di-tert-butyldicarbonate," Synlett, 1996, pp. 502-504.
Kolasa., "Thiazolylidene Derivatives as Cannabinoid Receptor Ligands and Their Preparation" Accession No. 2008:1184581, Mar. 22, 2011.
Kruijtzer J., et al., "Approaches to the Synthesis of Ureapeptoid Peptidomimetics," Tetrahedron Letters, 1997, vol. 38 (30), pp. 5335-5338.
Kubinyi, "3D QSAR in Drug Design: Ligand Protein Interactions & Molecular Similarity, 800 pages," Springer, 1998, vol. 2-3, pp. 243-244.
Lamothe M., et al., "A Simple One-Pot Preparation of N,N'-unsymmetrical ureas from N-Boc Protected Primary Anilines and Amines," Synlett, 1996, vol. 6, pp. 507-508.
Lemoucheux L., et al., "Debenzylation of Tertiary Amines Using Phosgene or Triphosgene: An Efficient and Rapid Procedure for the Preparation of Carbamoyl Chlorides and Unsymmetrical Ureas. Application in Carbon-11 Chemistry," Journal of Organic Chemistry, 2003, vol. 68 (19), pp. 7289-7297.
Leung M.K., et al., "S,S-Dimethyl Dithiocarbonate: A Convenient Reagent for the Synthesis of Symmetrical and Unsymmetrical Ureas," Journal of Organic Chemistry, 1996, vol. 61 (12), pp. 4175-4179.
Linn, et al., Journal of American Chemistry Society, 1963, 2032, vol. 85.
Maclennan S.J., et al., "Evidence for Inverse Agonism of SR141716A at Human Recombinant Cannabinoid CB1 and CB2 Receptors," British Journal of Pharmacology, 1998, vol. 124 (4), pp. 619-622.
Majer P., et al., "A Safe and Efficient Method for Preparation of N,"-Unsymmetrically Disubstituted Ureas Utilizing Triphosgene," Journal of Organic Chemistry, 1994, vol. 59, pp. 1937-1938.
Malan T.P., et al., "Inhibition of Pain Responses by Activation of CB(2) Cannabinoid Receptors," Chemistry and Physics of Lipids, 2002, vol. 121 (1-2), pp. 191-200.
Mallat A., et al., "Cannabinoid Receptors as New Targets of Antifibrosing Strategies during Chronic Liver Diseases," Expert Opinion on Therapeutic Targets, 2007, vol. 11 (3), pp. 403-409.
Masciadri R., et al., "Regioselective Friedel_Crafts Alkylation of Anilines and Amino-Substituted Heteroarenes with Hexafluoroacetone Sesquihydrate," European Journal of Organic Chemistry, 2003, vol. 2003 (21), pp. 4286-4291.
Mayo clinic, Alzheimer's disease, [retrieved on Mar. 11, 2013]. Retrieved from the Internet< URL: http://www.mayoclinic.com/health/alzheimers-disease/DS00161/DSECTION=prevention>.

Meyers A.I., et al., "Oxazolines. XX. Synthesis of Achiral and Chiral Thiiranes and Olefins by Reaction of Carbonyl Compounds with 2-(Alkylthio)-2-oxazolines ," Journal of Organic Chemistry, 1976, vol. 41 (10), pp. 1735-1742.
Miyaura N., et al., ed., Topics in Current Chemistry: Cross-Coupling Reactions, Springer, 2002, Table of Contents.
Morii T., et al., "A General Strategy to Determine a Target DNA Sequence of a Short Peptide: Application to a [D]-Peptide," Journal American Chemical Society, 2002, vol. 124 (2), pp. 180-181.
Morissette S.L., et al., "High-throughput Crystallization: Polymorphs, Salts, Co-crystals and Solvates of Pharmaceutical Solids.," Advanced Drug Delivery Reviews, 2004, vol. 56 (3), pp. 275-300.
Mucke L., "Neuroscience: Alzheimer's Disease," Nature, 2009, vol. 461 (7266), pp. 895-897.
Negishi E., et al., eds., Handbook of Organopalladium Chemistry For Organic Synthesis, vol. 1, John Wiley & Sons, 2002, Table of Contents.
Nieuwenhuijzen J.W., et al., "Solid and Solution Phase Combinatorial Synthesis of Ureas," Tetrahedron Letters, 1998, vol. 39, pp. 7811-7814.
Non-Final Office Action mailed Jun. 1, 2011 for U.S. Appl. No. 12/554,445, filed Sep. 4, 2009.
Non-Final Office Action mailed Jun. 1, 2011 for U.S. Appl. No. 12/560,897, filed Sep. 16, 2009.
Non-Final Office Action mailed Sep. 7, 2010 for U.S. Appl. No. 12/120,969, filed May 15, 2008.
Non-Final Office Action mailed Mar. 9, 2012 for U.S. Appl. No. 12/732,428, filed Mar. 26, 2010.
Non-Final Office Action mailed Jan. 12, 2010 for U.S. Appl. No. 12/120,969, filed May 15, 2008.
Non-Final Office Action mailed Aug. 23, 2011 for U.S. Appl. No. 12/639,173, filed Dec. 16, 2009.
Non-Final Office Action mailed Jan. 27, 2011 for U.S. Appl. No. 12/274,105, filed Nov. 19, 2008.
Ohta H., et al., "Imine Derivatives as new Potent and Selective CB2 Cannabinoid Receptor agonist with an Analgesic Action," Bioorganic and Medicinal Chemistry, 2007, vol. 16 (3), pp. 1111-1124.
Ozaki S., et al., "Recent Advances in Isocyanate Chemistry," Chemical Reviews, 1972, vol. 72 (5), pp. 457-496.
Padgett L.W., et al., "Recent Developments in Cannabinoid Ligands," Life Sciences, 2005, vol. 77 (14), pp. 1767-1798.
Partch, R., et al., "2-Oxaadamantane-1-N,N,N-trimethylmethanaminium Iodide:1 Synthesis and Potential for Muscarinic Activity," Croatia Chemical Acta, 1985, vol. 58 (4), pp. 661-669.
Ralston S.H., "Genetic Determinants of Susceptibility to Osteoporosis," Current Opinion in Pharmacology, 2003, vol. 3, pp. 286-290.
Rezoni G.E., et al., "Synthesis of 7-Carboxytricyclo[33103,7]nonan-3-ol," Journal of Organic Chemistry, 1983, vol. 48, pp. 5231-5236.
Sabnis R.W., et al., "2-Aminothiophenes by the Gewald Reaction," Journal of Heterocyclic Chemistry, 1999, vol. 36, pp. 333-345.
Schafer S., et al., "Failure is an Option: Learning from Unsuccessful Proof-of-concept Trials," Drug Discovery Today, 2008, vol. 13 (21-22), pp. 913-916.
Schuart J., et al., "2-aminooxazoles and 2-iminooxazolines. 3. Selected Examples of a Homolog Series of 3 Substituted 2-imino-4-methyl-5-phenyloxazolines," Die Pharmazie, 1974, vol. 29 (3), pp. 170-172.
Scialdone M.A., et al., "Phosgenated p-nitrophenyl(polystyrene)ketoxime or phoxime resin. A new resin for the solid-phase synthesis of ureas via thermolytic cleavage of oxime-carbamates", Journal of Organic Chemistry, 1998, vol. 63, pp. 4802-4807.
Shultz D.A., et al., "Synthesis of Bis(semiquinone)s and their Electrochemical and Electron Paramagnetic Resonance Spectral Characterization," Journal of Organic Chemistry, 1998, vol. 63(25), pp. 9462-9469.
STN International HCAPLUS database Accession No. 2008:1184581, Columbus, Ohio, Lolasa et al, 2008.
Supplementary European Search Report for Application No. EP08837396, mailed on Jan. 16, 2012, 2 pages.

(56) References Cited

OTHER PUBLICATIONS

Supplementary European Search Report for Application No. EP08852528, mailed on Nov. 8, 2010, 2 pages.
Takeda K., et al., "Convenient Methods for Syntheses of Active Carbamates, Ureas and Nitrosoureas Using N,N-disuccinimido Carbonate (DSC)," Tetrahedron Letters, 1983, vol. 24, pp. 4569-4572.
Vasil'Eva V.F., et al., " Synthesis and Properties of 2-imino-3-benzyl-5-phenyl-1,3,4-oxadiazoline, "Caplus, 1970.
Viallet, et al., "2-Aminothiazoline, etc," 1980, CA 93:8074.
Vippagunta S.R., et al., "Crystalline Solids," Advanced Drug Delivery Reviews, 2001, vol. 48 (1), pp. 3-26.
Wermuth, "The practice of Medicinal chemistry," 2003, Chapters 9-10, 2nd edition, 768 pages.
Whiteside G.T., et al., "The Role of the Cannabinoid Cb2 Receptor in Pain Transmission and Therapeutic Potential of Small Molecule CB2 Receptor Agonists," Current medicinal chemistry, 2007, vol. 14 (8), pp. 917-936.
Williams K., et al., "Central Nervous System Perivascular Cells Are Immunoregulatory Cells that Connect the CNS tith the Peripheral mune System," Journal Of Glia, 2001, vol. 36 (2), pp. 156-164.
Wu K.M., et al., "Regulatory Perspectives of Type II Prodrug Development and Time-Dependent Toxicity Management Nonclinical Pharm/Tox Analysis and the Role of Comparative Toxicology," Toxicology, 2007, vol. 236 (1-2), pp. 1-6.
Yao B.B., et al., "In Vitro Pharmacological Characterization Of Am1241: A Protean Agonist At The Cannabinoid Cb2 Receptor," British Journal Pharmacology, 2006, vol. 149 (2), pp. 145-154.
Final Office Action mailed May 23, 2014 for U.S. Appl. No. 12/246,808, filed Oct. 7, 2008.
Notice of Allowance mailed Jun. 9, 2014 for U.S. Appl. No. 12/560,893, filed Sep. 16, 2009.
Notice of Allowance mailed Jun. 9, 2014 for U.S. Appl. No. 12/639,173, filed Dec. 16, 2009.
Notice of Allowance mailed Jun. 9, 2014 for U.S. Appl. No. 12/970,435, filed Dec. 16, 2010.
Notice of Allowance mailed May 14, 2014 for U.S. Appl. No. 12/274,105, filed Nov. 19, 2008.
Office Action mailed Jun. 30, 2014 for U.S. Appl. No. 12/970,480, filed Dec. 16, 2010.

\* cited by examiner

COMPOUNDS AS CANNABINOID RECEPTOR LIGANDS

This application claims priority to U.S. Patent Application Ser. No. 61/095,000 filed Sep. 8, 2008 and U.S. Patent Application Ser. No. 61/224,205 filed Jul. 9, 2009, both of which are incorporated herein by reference in its entirety.

TECHNICAL FIELD AND BACKGROUND

Compounds that are cannabinoid receptor ligands, compositions comprising such compounds, and methods of treating conditions and disorders using such compounds and compositions, are disclosed herein.

(−)-$\Delta^9$-Tetrahydrocannabinol ($\Delta^9$-THC), the major psychoactive constituent of marijuana, exerts a broad range of effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in pre-clinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic). Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, fibromyalgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

SUMMARY

Disclosed herein are compounds of formula (I)

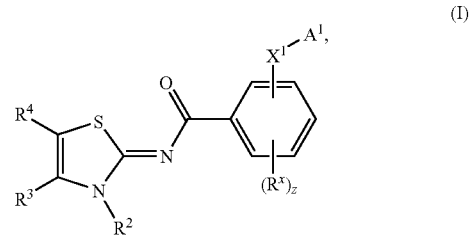

(I)

or pharmaceutically acceptable salts, solvates, prodrugs, salts of prodrugs, or combinations thereof, wherein $X^1$ is O, S, S(O), S(O)$_2$, or N(R$^{bx}$); wherein R$^{bx}$ is hydrogen, alkyl, haloalkyl, alkoxyalkyl, —C(O)O(alkyl), monocyclic cycloalkyl, —(CR$^{1c}$R$^{1d}$)$_{q3}$-(monocyclic cycloalkyl), or haloalkoxyalkyl; and $A^1$ is -G$^{1a}$-G$^{1b}$, —(CR$^{1a}$R$^{1b}$)$_{q1}$-G$^{1c}$, —(CR$^{1a}$R$^{1b}$)$_{q1}$-A$^2$, —(CR$^{1g}$R$^{1h}$)$_{q2}$-A$^4$, —N(R$^b$)C(O)R$^a$, —N(R$^b$)C(O)OR$^d$, —N(R$^b$)C(O)N(R$^b$)(R$^c$), —N(R$^b$)(R$^c$), or —N=C(R$^p$)(R$^q$); or $X^1$ and $A^1$ together is N=N(R$^{cx}$); wherein R$^{cx}$ is alkyl, haloalkyl, —(CR$^{1a}$R$^{1b}$)$_{q3}$-A$^3$, G$^{1d}$, or —(CR$^{1a}$R$^{1b}$)$_{q3}$-G$^{1d}$;

R$^p$ is hydrogen, alkyl, haloalkyl, —(CR$^{1a}$R$^{1b}$)$_{q3}$-A$^3$, —C(O)OR$^d$, —C(O)R$^d$, G$^{1d}$, or —(CR$^{1a}$R$^{1b}$)$_{q3}$-G$^{1d}$;

R$^q$ is hydrogen, alkyl, haloalkyl, —N(R$^b$)(R$^c$), —(CR$^{1a}$R$^{1b}$)$_{q3}$-A$^3$, G$^{1d}$, or —(CR$^{1a}$R$^{1b}$)$_{q3}$-G$^{1d}$; or R$^p$ and R$^q$, together with the carbon atom to which they are attached, form a monocyclic 5-, 6-, 7-, or 8-membered cycloalkyl or heterocycle ring, optionally substituted with 1, 2, 3, 4, or 5 substituents independently selected from the group consisting of oxo, alkyl, haloalkyl, and halogen;

$A^2$ is —C(O)R$^a$, —S(O)$_2$R$^d$, —C(O)N(R$^b$)(R$^c$), —C(S)N(R$^b$)(R$^c$), —S(O)$_2$N(R$^b$)(R$^c$), —C(=NOR$^f$)R$^a$, —CN, —N(R$^c$)C(O)R$^d$, —N(R$^c$)C(O)OR$^d$, —N(R$^c$)S(O)$_2$R$^d$, —N(R$^c$)C(O)N(R$^b$)(R$^c$), —N(R$^c$)S(O)$_2$N(R$^b$)(R$^c$), -L$^1$-G$^{1d}$, -L$^1$—(CR$^{1a}$R$^{1b}$)$_{q3}$-G$^{1d}$, -L$^1$—(CR$^{1a}$R$^{1b}$)$_{q1}$-A$^3$, —O—(CR$^{1a}$R$^{1b}$)$_{q2}$—O-alkyl, —OH, or —O(haloalkyl);

$A^3$ is C(O)R$^h$, —S(O)$_2$R$^e$, —C(O)N(R$^h$)$_2$, —C(S)N(R$^h$)$_2$, —S(O)$_2$N(R$^h$)$_2$, —C(=NOR$^h$)R$^h$, —N(R$^h$)C(O)R$^h$, —N(R$^h$)C(O)OR$^e$, —N(R$^h$)S(O)$_2$R$^e$, —N(R$^h$)C(O)N(R$^h$)$_2$, —N(R$^h$)S(O)$_2$N(R$^h$)$_2$, —CN, —OR$^j$, or —N(R$^h$)$_2$;

$A^4$ is cycloalkyl, alkoxy, or N(R$^{1m}$)$_2$;

$L^1$ is O or N(R$^b$);

$R^a$ and $R^c$, at each occurrence, are each independently hydrogen, alkyl, haloalkyl, —$(CR^{1a}R^{1b})_{q3}$—O-alkyl, —$(CR^{1a}R^{1b})_{q3}$-$A^3$, $G^{1d}$, or —$(CR^{1a}R^{1b})_{q3}$-$G^{1d}$;

$R^b$, at each occurrence, is each independently hydrogen, alkyl, haloalkyl, alkoxyalkyl, cycloalkyl, —$(CR^{1c}R^{1d})_{q3}$-(cycloalkyl), or haloalkoxyalkyl;

$R^d$, at each occurrence, is alkyl, haloalkyl, —$(CR^{1a}R^{1b})_{q3}$—O-alkyl, —$(CR^{1a}R^{1b})_{q3}$-$A^3$, $G^{1d}$, or —$(CR^{1a}R^{1b})_{q3}$-$G^{1d}$;

$R^j$ is hydrogen, $C_1$-$C_4$ haloalkyl, monocyclic cycloalkyl, or —$(CR^{1c}R^{1d})_{q3}$-(monocyclic cycloalkyl);

$R^m$ is haloalkyl, —$(CR^{1a}R^{1b})_{q3}$—O-alkyl, —$(CR^{1a}R^{1b})_{q3}$-$A^3$, $G^{1d}$, or —$(CR^{1a}R^{1b})_{q3}$-$G^{1d}$;

$R^{1b}$, at each occurrence, is independently hydrogen, halo, $C_1$-$C_4$ alkyl, $C_1$-$C_4$ haloalkyl, —$OR^h$, —$N(R^h)_2$, —$N(R^h)C(O)R^h$, —$N(R^h)C(O)OR^h$, or —$N(R^h)S(O)_2R^e$;

$R^{1g}$, at each occurrence, is independently hydrogen, halo, $C_1$-$C_4$ alkyl, $C_1$-$C_4$ haloalkyl, —$OR^h$, —$N(R^h)_2$, —$N(R^h)C(O)R^h$, —$N(R^h)C(O)OR^e$, or —$N(R^h)S(O)_2R^e$; provided that at least one occurrence of $R^{1g}$ is halo, $C_1$-$C_4$ haloalkyl, —$OR^h$, —$N(R^h)_2$, —$N(R^h)C(O)R^h$, —$N(R^h)C(O)OR^e$, or —$N(R^h)S(O)_2R^e$;

$R^{1m}$ is hydrogen, alkyl, haloalkyl, alkylcarbonyl, formyl, or alkoxyalkyl; or two $R^{1m}$ taken together with the nitrogen atom to which they are attached form a heterocyclic ring, optionally substituted with 1, 2, 3, or 4 substituents selected from alkyl, hydroxy, oxo and haloalkyl;

$G^{1a}$ and $G^{1b}$, are each independently cycloalkyl, cycloalkenyl, heterocycle, aryl, or heteroaryl;

$G^{1c}$ is cycloalkenyl, heterocycle, aryl, or heteroaryl;

wherein the ring as represented by $G^{1a}$ is optionally substituted with 1, 2, 3, 4, or 5 substituents independently selected from the group consisting of alkyl, alkenyl, alkynyl, halo, haloalkyl, =N—CN, =N—$OR^f$, —CN, oxo, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, and —$N(R^f)C(O)N(R)_2$;

wherein the cycloalkyl of $A^4$ and the rings as represented by $G^{1b}$ and $G^{1c}$, are each optionally substituted with 1, 2, 3, 4, or 5 substituents independently selected from the group consisting of $G^{1d}$, —$(CR^{1c}R^{1d})_{q3}$-$G^{1d}$, alkyl, alkenyl, alkynyl, halo, haloalkyl, =N—CN, =N—$OR^f$, —CN, oxo, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$; —$(CR^{1c}R^{1d})_{q3}$—C(=$NOR^f$)($R^a$), —$(CR^{1c}R^{1d})_{q3}$—$OR^f$, —$(CR^{1c}R^{1d})_{q3}$—$OC(O)R^f$, —$(CR^{1c}R^{1d})_{q3}$—$OC(O)N(R^f)_2$, —$(CR^{1c}R^{1d})_{q3}$—$S(O)_2R^e$, —$(CR^{1c}R^{1d})_{q3}$—$S(O)_2N(R^f)_2$, —$(CR^{1c}R^{1d})_{q3}$—$C(O)R^f$, —$(CR^{1c}R^{1d})_{q3}$—$C(O)OR^f$, —$(CR^{1c}R^{1d})_{q3}$—$C(O)N(R^f)_2$, —$(CR^{1c}R^{1d})_{q3}$—$N(R^f)_2$, —$(CR^{1c}R^{1d})_{q3}$—$N(R^f)C(O)R^f$, —$(CR^{1c}R^{1d})_{q3}$—$N(R^f)S(O)_2R^e$, —$(CR^{1c}R^{1d})_{q3}$—$N(R^f)C(O)O(R^e)$, —$(CR^{1c}R^{1d})_{q3}$—$N(R^f)C(O)N(R^f)_2$, and —$(CR^{1c}R^{1d})_{q3}$—CN;

$G^{1d}$, at each occurrence, is independently a monocyclic heterocycle, a monocyclic heteroaryl, a phenyl, a monocyclic cycloalkyl, or a monocyclic cycloalkenyl; optionally substituted with 1, 2, 3, or 4 substituents selected from the group consisting of —$N(R^h)_2$, —CN, oxo, alkyl, haloalkyl, alkoxy, haloalkoxy, halo, and hydroxy;

$R^e$ and $R^i$, at each occurrence, are each independently $C_1$-$C_4$ alkyl, $C_1$-$C_4$ haloalkyl, monocyclic cycloalkyl, or —$(CR^{1c}R^{1d})_{q3}$-(monocyclic cycloalkyl);

$R^f$, at each occurrence, is independently hydrogen, $C_1$-$C_4$ alkyl, $C_1$-$C_4$ haloalkyl, —$(CR^{1c}R^{1d})_{q3}$—$OR^g$, monocyclic cycloalkyl, monocyclic heterocycle, or —$(CR^{1c}R^{1d})_{q3}$-(monocyclic cycloalkyl);

$R^g$ and $R^h$, at each occurrence, are each independently hydrogen, $C_1$-$C_4$ alkyl, $C_1$-$C_4$ haloalkyl, monocyclic cycloalkyl, or —$(CR^{1c}R^{1d})_{q3}$-(monocyclic cycloalkyl);

wherein the cycloalkyl, the monocyclic cycloalkyl, and the monocyclic heterocycle, as a substituent or part of a substituent, of $R^b$, $R^{bx}$, $R^e$, $R^i$, $R^f$, $R^g$, $R^h$, and $R^j$, at each occurrence, are each independently unsubstituted are substituted with 1, 2, 3, or 4 substituents selected from the group consisting of $C_1$-$C_4$ alkyl, halo, hydroxy, $C_1$-$C_4$ alkoxy, $C_1$-$C_4$ haloalkoxy, and $C_1$-$C_4$ haloalkyl;

$R^2$ is —$(CR^{2a}R^{2b})_{q4}$—OH, —$(CR^{2a}R^{2b})_{q4}$—O-alkyl, —$(CR^{2a}R^{2b})_{q4}$—O—$(CR^{2c}R^{2d})_{q3}$—O-alkyl, or —$(CR^{2a}R^{2b})_{q5}$-$G^2$;

$G^2$ is a 4-, 5-, 6-, 7-, 8-, or 9-membered monocyclic heterocycle containing zero or one double bond, one or two oxygen, and zero or one nitrogen as ring atoms; two non-adjacent atoms of said heterocycle ring can be optionally linked by an alkenylene bridge of 2, 3, or 4 carbon atoms, or optionally linked by an alkylene bridge of 1, 2, 3, or 4 carbon atoms; or $G^2$ is furanyl, oxazolyl, isoxazolyl, or oxadiazolyl; each ring $G^2$ is optionally fused with a monocyclic ring selected from the group consisting of benzo, cycloalkyl, cycloalkenyl, heterocycle and heteroaryl; and each $G^2$ is independently unsubstituted or substituted with 1, 2, 3, 4, 5, or 6 substituents independently selected from the group consisting of oxo, alkyl, halo, —OH, alkoxy, and haloalkyl;

$R^3$ and $R^4$ are each independently $G^3$, hydrogen, alkyl, alkenyl, alkynyl, —$NO_2$, —CN, halo, —$OR^h$, —$N(R^h)_2$, —$C(O)R^h$, —$C(O)O(R^h)$, haloalkyl, —$(CR^{3a}R^{3b})_{q6}$—$OR^h$, —$(CR^{3a}R^{3b})_{q6}$—$N(R^h)_2$, —$(CR^{3a}R^{3b})_{q3}$—$C(O)R^h$, or —$(CR^{3a}R^{3b})_{q3}$—$C(O)O(R^h)$;

$R^3$ and $R^4$, together with the carbon atoms to which they are attached, optionally form a 4-, 5-, 6-, or 7-membered monocyclic ring that contains zero, one or two additional double bond, zero or one oxygen atom, and zero, one or two nitrogen atom as ring atoms; two non-adjacent atoms of said monocyclic ring can be optionally linked by an alkenylene bridge of 2, 3, or 4 carbon atoms, or optionally linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, —OH, alkoxy, and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl;

$G^3$ is cycloalkyl, cycloalkenyl, aryl, heterocycle, or heteroaryl, each of which is independently unsubstituted or substituted with 1, 2, 3, or 4 substituents selected from the group consisting of $C_1$-$C_4$ alkyl, $C_2$-$C_4$ alkenyl, $C_2$-$C_4$ alkynyl, halo, $C_1$-$C_4$ haloalkyl, =N—CN, =N—$OR^h$, —CN, oxo, —$OR^h$, —$OC(O)R^h$, —$OC(O)N(R^h)_2$, —$S(O)_2R^1$, —$S(O)_2N(R^h)_2$, —$C(O)R^h$, —$C(O)OR^h$, —$C(O)N(R^h)_2$, —$N(R^h)_2$, —$N(R^h)C(O)R^h$, —$N(R^h)S(O)_2R^1$, —$N(R^h)C(O)O(R^1)$, and —$N(R^h)C(O)N(R^h)_2$;

$R^{1a}$, $R^{1h}$ $R^{1c}$, $R^{1d}$, $R^{2a}$, $R^{2b}$, $R^{2c}$, $R^{2d}$, $R^{3a}$, and $R^{3a}$, at each occurrence, are each independently hydrogen, halo, $C_1$-$C_4$ alkyl, or $C_1$-$C_4$ haloalkyl;

$R^x$, at each occurrence, is independently $G^{1d}$, alkyl, alkenyl, alkynyl, halo, haloalkyl, —CN, —$OR^f$, —$OC(O)R^f$, —$OC(O)N(R^f)_2$, —$S(O)_2R^e$, —$S(O)_2N(R^f)_2$, —$C(O)R^f$, —C(O)OR$^f$, —C(O)N(R$^f$)$_2$, —N(R$^f$)C(O)R$^f$, —N(R$^f$)S(O)$_2$R$^e$, —N(R$^f$)C(O)O(R$^e$), —N(R$^f$)C(O)N(R$^f$)$_2$, —(CR$^{1c}$R$^{1d}$)$_{q3}$—OR$^f$, —(CR$^{1c}$R$^{1d}$)$_{q3}$—OC(O)R$^f$, —(CR$^{1c}$R$^{1d}$)$_{q3}$—OC(O)N(R$^f$)$_2$, —(CR$^{1c}$R$^{1d}$)$_{q3}$—S(O)$_2$R$^e$, —(CR$^{1c}$R$^{1d}$)$_{q3}$—S(O)$_2$N(R$^f$)$_2$, —(CR$^{1c}$R$^{1d}$)$_{q3}$—C(O)R$^f$, —(CR$^{1c}$R$^{1d}$)$_{q3}$—C(O)OR$^f$, —(CR$^{1c}$R$^{1d}$)$_{q3}$—C(O)N(R$^f$)$_2$, —(CR$^{1c}$R$^{1d}$)$_{q3}$—N(R$^f$)$_2$, —(CR$^{1c}$R$^{1d}$)$_{q3}$—N(R$^f$)C(O)R$^f$, —(CR$^{1c}$R$^{1d}$)$_{q3}$—N(R$^f$)S(O)$_2$R$^e$, —(CR$^{1c}$R$^{1d}$)$_{q3}$—N(R$^f$)C(O)O(R$^e$), —(CR$^{1c}$R$^{1d}$)$_{q3}$—N(R$^f$)C(O)N(R$^f$)$_2$, or —(CR$^{1c}$R$^{1d}$)$_{q3}$—CN;

q1 is 1, 2, 3, or 4;

q2 and q4, at each occurrence, are each independently 2, 3, 4, or 5;

q3 is 1, 2 or, 3;

q5 and q6, at each occurrence, are each independently 1, 2, 3, 4, 5, or 6; and z is 0, 1, 2, 3, or 4;

with the proviso that (i) when X$^1$ is N(R$^{bx}$) wherein R$^{bx}$ is hydrogen, alkyl, haloalkyl or alkoxyalkyl; and R$^2$ is —(CR$^{2a}$R$^{2b}$)$_{q4}$—OH or —(CR$^{2a}$R$^{2b}$)$_{q4}$—O-alkyl; then A$^1$ is not —(CR$^{1a}$R$^{1b}$)$_{q1}$—OH;

(ii) when X$^1$ is O; and G$^{1b}$ and G$^{1c}$ are heterocycle, then G$^{1b}$ and G$^{1c}$ are each connected to the parent moiety through the ring carbon atom; and (iii) when X$^1$ is S(O)$_2$ and R$^2$ is —(CR$^{2a}$R$^{2b}$)$_{q4}$—OH or —(CR$^{2a}$R$^{2b}$)$_{q4}$—O-alkyl; then A$^1$ is not N(H)$_2$, N(alkyl)(H), or N(alkyl)$_2$.

Another aspect relates to pharmaceutical compositions comprising therapeutically effective amount of one or more compound(s) described herein or pharmaceutically acceptable salts or solvates thereof, in combination with one or more pharmaceutically acceptable carrier(s). Such compositions can be administered in accordance with a methods described herein, typically as part of a therapeutic regimen for treatment or prevention of conditions and disorders related to cannabinoid (CB) receptor subtype CB$_2$. More particularly, the methods are useful for treating conditions related to pain such as, but not limited to, neuropathic pain, nociceptive pain, osteoarthritic pain, inflammatory pain, cancer pain, lower back pain, eye pain, and post-operative pain; inflammatory disorders, immune disorders, neurological disorders, cancers of the immune system, respiratory disorders, obesity, diabetes, cardiovascular disorders, or for providing neuroprotection.

Further, provided herein is the use of present compounds or pharmaceutically acceptable salts or solvates thereof, in the manufacture of medicaments for the treatment of the disease conditions described above, alone or in combination with one or more pharmaceutically acceptable carrier(s), particularly for the treatment of pain such as, but not limited to, neuropathic pain, nociceptive pain, osteoarthritic pain, inflammatory pain, cancer pain, lower back pain, eye pain, and post-operative pain, or combinations thereof.

The compounds, compositions comprising the compounds, and methods for treating or preventing conditions and disorders by administering the compounds or compositions are further described herein.

These and other objectives of the invention are described in the following paragraphs. These objectives should not be deemed to narrow the scope of the invention.

DETAILED DESCRIPTION

Compounds of formula (I)

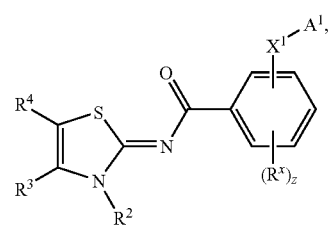

wherein X$^1$, A$^1$, R$^x$, R$^2$, R$^3$, R$^4$, and z are as defined above in the Summary and below in the Detailed Description. Compositions comprising such compounds and methods for treating conditions and disorders using such compounds and compositions are also disclosed.

In various embodiments, compounds described herein may contain variables that occur more than one time in any substituent or in the compound described or any other formulae herein. Definition of a variable on each occurrence is independent of its definition at another occurrence. Further, combinations of variables are permissible only if such combinations result in stable compounds. Stable compounds are compounds that can be isolated from a reaction mixture.

a. DEFINITIONS

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "C$_2$-C$_4$ alkenyl" means an alkenyl group containing 2-4 carbon atoms. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double. Representative examples of alkenylene include, but are not limited to, —CH=CH— and —CH$_2$CH=CH—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkyl" as used herein, means a straight or branched, saturated hydrocarbon chain containing from 1 to 10 carbon atoms. The term "C$_1$-C$_4$ alkyl" means a straight or branched chain hydrocarbon containing 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" means an alkyl group as defined herein, appended to the parent molecular moiety through a C(O) group. Representative examples of alkylcarbonyl include, but are not limited to, acetyl, 1-oxopropyl, 2,2-dimethyl-1-oxopropyl, 1-oxobutyl, and 1-oxopentyl.

The term "alkylene" means a divalent group derived from a straight or branched chain hydrocarbon of 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "C$_2$-C$_4$ alkynyl" means an alkynyl group of 2 to 4 carbon atoms. Representative examples of alkynyl include, but are not limited to, acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups can be unsubstituted or substituted.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. The term "C$_1$-C$_4$ haloalkyl" means a haloalkyl group of 1-4 carbon atoms. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "haloalkoxy" as used herein, means an alkoxy group, as defined herein, in which one, two, three, four, five or six hydrogen atoms are replaced by halogen. Representative examples of haloalkyl include, but are not limited to, 2-fluoroethoxy, 2,2,2-trifluoroethoxy, trifluoromethoxy, and difluoromethoxy.

The term "haloalkoxyalkyl" as used herein, means a haloalkoxy group, as defined herein, appended to the parent moiety through an alkyl group, as defined herein.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl (e.g. azetidin-2-yl. azetidin-3-yl), azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl (e.g. morpholin-2-yl, morpholin-3-yl, etc.), oxadiazolinyl, oxadiazolidinyl, oxazolinyl, oxazolidinyl, piperazinyl (piperazin-2-yl, and the like), piperidinyl (e.g. piperidin-2-yl, piperidin-3-yl, piperidin-4-yl, etc.), pyranyl, pyrazolinyl, pyrazolidinyl, pyrrolinyl, pyrrolidinyl (e.g. pyrrolidin-2-yl, pyrrolidin-3-yl, and the like), tetrahydrofuranyl, tetrahydropyranyl (e.g. tetrahydro-2H-pyran-2-yl, etc.), tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, 2,3-dihydrobenzofuranyl, 2,3-dihydrobenzothienyl, azabicyclo[2.2.1]heptyl (including 2-azabicyclo [2.2.1]hept-2-yl), and 2,3-dihydro-1H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta [b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles can be unsubstituted or substituted. The monocyclic, bicyclic, and tricyclic heterocycles are connected to the parent molecular moiety through any carbon atom or any nitrogen atom contained within the rings, except for those represented by the variables $G^{1b}$ and $G^{1c}$ when $X^1$ is O. When $X^1$ is O, each of the heterocycles represented by $G^{1b}$ and $G^{1c}$ is connected to the parent moiety through the substitutable carbon atom of the rings only. The nitrogen and sulfur heteroatoms in the heterocycle rings may optionally be oxidized (e.g. 1,1-dioxidotetrahydrothienyl, oxidopyrrolidin-2-yl) and the nitrogen atoms may optionally be quarternized.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl (e.g. 1H-imidazol-4-yl, 1H-imidazol-5-yl, etc.), isoxazolyl, isothiazolyl, oxadiazolyl, 1,3-oxazolyl (e.g. 1,3-oxazol-5-yl, etc.), pyridinyl (e.g. pyridin-2-yl, pyridin-3-yl, etc.), pyridazinyl, pyrimidinyl, pyrazinyl (e.g. pyrazin-2-yl, etc.), pyrazolyl (e.g. pyrazol-5-yl, etc.), pyrrolyl (e.g. pyrrol-1-yl, etc.), tetrazolyl, thiadiazolyl, 1,3-thiazolyl (e.g. 1,3-thiazol-2-yl, etc.), thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-c]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any carbon atom or any nitrogen atom contained within the ring systems. The nitrogen heteroatoms of the heteroaryl rings may optionally be oxidized (e.g. oxidopyridinyl), and are contemplated within the scope of the invention.

The term "heteroatom" as used herein, means a nitrogen, oxygen, or sulfur atom.

The term "hydroxyl" or "hydroxy" means a —OH group.

The term "oxo" as used herein, means a =O group.

b. COMPOUNDS

Compounds of formula (I) are as described above.

Particular values of variable groups in compounds of formula (I) are as follows. Such values may be used where appropriate with any of the other values, definitions, claims or embodiments defined hereinbefore or hereinafter.

$R^3$ and $R^4$ have values as described generally for compounds of formula (I).

Certain embodiments provides compounds of formula (I) wherein $R^3$ and $R^4$ the same or different, and are each independently $G^3$, hydrogen, alkyl, alkenyl, alkynyl, —CN, halo, —OR$^h$, haloalkyl, —(CR$^{3a}$R$^{3b}$)$_{q6}$—OR$^h$, or —(CR$^{3a}$R$^{3b}$)$_{q6}$—N(R$^h$)$_2$, wherein $G^3$, $R^{3a}$, $R^{3b}$, $R^h$, and q6 are as described in the Summary and in embodiments herein. For example, $R^{3a}$, $R^{3b}$, and $R^h$ are each independently hydrogen or $C_1$-$C_4$ alkyl. q6, for example, is 1. In certain embodiments, $G^3$ is a monocyclic cycloalkyl, optionally substituted as described generally in the Summary. Examples of compounds of formula (I) include those wherein $R^3$ and $R^4$ are each independently hydrogen or alkyl (for example, $C_1$-$C_4$ alkyl such as, but not limited to, methyl, ethyl, isopropyl, tert-butyl). In certain embodiments, $R^3$ is hydrogen or alkyl (e.g. $C_1$-$C_4$ alkyl such as, but not limited to, methyl) and $R^4$ is alkyl (for example, $C_1$-$C_4$ alkyl such as, but not limited to, methyl, ethyl, isopropyl, tert-butyl). In certain embodiments, $R^3$ is hydrogen and $R^4$ is methyl, tert-butyl, or isopropyl.

In certain embodiments, $R^3$ and $R^4$, together with the carbon atoms to which they are attached form a 4-, 5-, 6-, or 7-membered monocyclic ring that contains zero or one additional double bond and zero or one oxygen atom as ring atoms; two non-adjacent atoms of said monocyclic ring can be optionally linked by an alkenylene bridge of 2, 3, or 4 carbon atoms, or optionally linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, —OH, —O(alkyl), and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl; or $R^3$ and $R^4$, together with the carbon atoms to which they are attached, optionally form a 6-membered monocyclic ring that contains two additional double bonds and one or two nitrogen atom as ring atoms wherein the monocyclic ring is unsubstituted or substituted with 1, 2 or 3 substituents selected from the group consisting of alkyl, halo, —OH, alkoxy, and haloalkyl.

$X^1$ has values as set forth in the Summary. For example, certain embodiments are directed to compounds wherein $X^1$ is O or N(R$^{bx}$). Certain embodiments are directed to those wherein $X^1$ is S. Further embodiments are directed to those wherein $X^1$ is O. In certain classes of compounds $X^1$ is N(R$^{bx}$). R$^{bx}$ in the abovementioned compounds are as set forth in the Summary and embodiments herein. For example, R$^{bx}$ is hydrogen, alkyl (e.g. methyl), or —C(O)O(alkyl). In certain embodiments, R$^{bx}$ is hydrogen.

As described generally above for compounds of formula (I), $A^1$ is -G$^{1a}$-G$^{1b}$, —(CR$^{1a}$R$^{1b}$)$_{q1}$-G$^{1c}$, —(CR$^{1a}$R$^{1b}$)$_{q1}$-A$^2$, —(CR$^{1g}$R$^{1b}$)$_{q2}$-A$^4$, —N(R$^b$)C(O)R$^a$, —N(R$^b$)C(O)OR$^d$, —N(R$^b$)C(O)N(R$^b$)(R$^c$), —N(R$^b$)(R$^c$), or —N=C(R$^p$)(R$^q$). For example, $A^1$ is —(CR$^{1a}$R$^{1b}$)$_{q1}$-G$^{1c}$, R$^{1a}$, R$^{1b}$, q1, G$^{1c}$, A$^2$, R$^{1g}$, R$^{1h}$, q2, A$^4$, R$^p$, R$^q$, R$^b$, R$^a$, R$^d$, and R$^c$ are as described in the Summary and embodiments described herein below.

Certain embodiments relate to compounds wherein $A^1$ is -$G^{1a}$-$G^{1b}$, and $G^{1a}$ and $G^{1b}$ are as described in the Summary and embodiments described herein. For example, $G^{1a}$ is a monocyclic cycloalkyl and $G^{1b}$ is a monocyclic heterocycle or a monocyclic heteroaryl; or $G^{1a}$ is a monocyclic heterocycle or a monocyclic heteroaryl and $G^{1b}$ is a monocyclic cycloalkyl, a monocyclic heterocycle or a monocyclic heteroaryl; and each of the rings as represented by $G^{1a}$ and $G^{1b}$ are independently unsubstituted or substituted as described generally in the Summary and embodiments described herein.

Other embodiments of the invention provide compounds of the formula (I) wherein $A^1$ is —$(CR^{1a}R^{1b})_{q1}$-$G^{1c}$ and $R^{1a}$, $R^{1b}$, q1, and $G^{1c}$ are as described in the Summary and embodiments described herein. For example, $R^{1a}$ and $R^{1b}$ are hydrogen or alkyl (e.g. $C_1$-$C_4$ alkyl such as, but not limited to, methyl). q1, for example, is 1 or 2. $G^{1c}$, for example, is phenyl, a monocyclic heterocycle (e.g. azetidinyl such as, but not limited to, azetidin-2-yl and azetidin-3-yl, pyrrolidinyl such as, but not limited to, pyrrolidin-2-yl, pyrrolidin-3-yl, piperidinyl such as, but not limited to, piperidin-2-yl, piperidin-3-yl, and piperidin-4-yl, tetrahydrofuranyl such as, but not limited to, tetrahydrofuran-2-yl, terahydropyranyl such as, but not limited to, tetrahydro-2H-pyran-2-yl, morpholinyl such as, but not limited to, morpholin-3-yl, piperazinyl such as, but not limited to, piperazin-2-yl), or a monocyclic heteroaryl (e.g. imidazolyl such as, but not limited to, 1H-imidazol-4-yl, 1H-imidazol-5-yl, pyridinyl such as, but not limited to, pyridin-2-yl, pyridin-3-yl, pyrazinyl such as, but not limited to, pyrazin-2-yl, oxazolyl such as, but not limited to, 1,3-oxazol-5-yl, thiazolyl such as, but not limited to, 1,3-thiazol-2-yl), each of the exemplary ring of $G^{1c}$ is independently unsubstituted or substituted as described in the Summary and in embodiments herein. In certain embodiments, the optional substituents of $G^{1c}$ are selected from the group consisting of —$(CR^{1c}R^{1d})_{q3}$-$G^{1d}$ (for example, —$CH_2$-phenyl), alkyl (e.g. $C_1$-$C_4$ alkyl such as, but not limited to, methyl, ethyl, isopropyl), halo, haloalkyl, oxo, —$S(O)_2R^e$ ($R^e$, for example, is $C_1$-$C_4$ alkyl such as, but not limited to, methyl), —$C(O)R^e$ ($R^e$, for example, is $C_1$-$C_4$ alkyl such as, but not limited to, methyl), and —$(CR^{1c}R^{1d})_{q3}$—$C(NOR^f)(R^a)$ wherein $R^f$, $R^a$, $R^{1c}$, $R^{1d}$, and q3 are as defined in the Summary and embodiments herein. For example , in certain embodiments, $R^f$, $R^a$, $R^{1c}$, and $R^{1d}$ are each independently hydrogen or $C_1$-$C_4$ alkyl (e.g. methyl).

In certain embodiments, $A^1$ is —$(CR^{1a}R^{1b})_{q1}$-$A^2$ wherein $R^{1a}$, $R^{1b}$, q1, and $A^2$ are as described in the Summary and in embodiments herein. $A^2$, for example, is $C(O)R^a$, —$C(=NOR^f)R^a$, OH, -$L^1$-$G^{1d}$, or -$L^1$—$(CR^{1a}R^{1b})_{q1}$-$A^3$. In certain embodiments, $A^1$ is —$(CR^{1a}R^{1b})_{q1}$—OH. $R^f$, $R^a$, $R^{1a}$, $R^{1b}$, $A^3$, and q1 are as described in the Summary and the embodiments herein. $L^1$, for example, is $N(R^b)$, and $R^b$ is hydrogen or alkyl (e.g. $C_1$-$C_4$ alkyl such as, but not limited to, methyl). $G^{1d}$, for example, is phenyl, optionally substituted as described in the Summary. $R^a$, for example, is alkyl (e.g. $C_1$-$C_4$ alkyl such as, but not limited to, methyl, ethyl, tert-butyl, etc.). $R^e$, for example, is hydrogen, $C_1$-$C_4$ alkyl, $C_1$-$C_4$ haloalkyl (e.g. $CF_3$), or optionally substituted monocyclic heterocycle (e.g. optionally substituted tetrahydropyranyl). $A^3$, for example, is —$OR^j$ wherein $R^j$ is as disclosed in the Summary and embodiments herein. For example, $R^j$ is hydrogen. $R^{1a}$ and $R^{1b}$, at each occurrence, are for example, independently hydrogen, alkyl (e.g. $C_1$-$C_4$ alkyl), $N(R^h)_2$, or —$N(R^h)C(O)R^h$. $R^h$, for example, is hydrogen, $C_1$-$C_4$ alkyl, or $C_1$-$C_4$ haloalkyl (e.g. $CF_3$). In certain embodiments, $R^{1a}$ and $R^{1b}$, at each occurrence, are for example, independently hydrogen or alkyl (e.g. $C_1$-$C_4$ alkyl).

In certain embodiments, $A^1$ is —$N(R^b)C(O)R^a$, —$N(R^b)C(O)OR^d$, —$N(R^b)C(O)N(R^b)(R^c)$, —$N(R^b)(R^c)$, or —$N=C(R^p)(R^q)$; wherein $R^a$, $R^b$, $R^c$, $R^d$, $R^p$, and $R^q$ are as described generally in the Summary and herein below.

One class of compounds is directed to those wherein $A^1$ is —$N(R^b)C(O)R^a$, —$N(R^b)C(O)OR^d$, or —$N(R^b)C(O)N(R^b)(R^c)$; wherein $R^a$, $R^b$, $R^c$, and $R^d$ are as disclosed in the Summary and herein. $R^b$ and $R^c$, for example, are each independently hydrogen or $C_1$-$C_4$ alkyl (e.g. methyl, ethyl, tert-butyl, etc.). $R^d$, for example, is alkyl (e.g. methyl, ethyl, tert-butyl) or haloalkyl. $R^a$, for example, is $C_1$-$C_4$ alkyl (including but not limited to, methyl, ethyl, tert-butyl), haloalkyl, or $G^{1d}$; wherein $G^{1d}$ are as set forth in the Summary and herein. $G^{1d}$, for example, is optionally substituted phenyl or an optionally substituted monocyclic heteroaryl (including but not limited to, pyridinyl). In certain embodiments, $R^a$ is $C_1$-$C_4$ alkyl (including but not limited to, methyl, ethyl, tert-butyl).

In certain embodiments, $A^1$ is —$N(R^b)(R^c)$ wherein $R^b$ and $R^c$ are as described generally in the Summary and herein. For example, $R^{1p}$ is hydrogen or alkyl (e.g. $C_1$-$C_4$ alkyl such as, but not limited to, isopropyl, methyl, ethyl) and $R^c$ is alkyl (e.g. $C_1$-$C_4$ alkyl such as, but not limited to, tert-butyl, isopropyl, methyl, ethyl), —$(CR^{1a}R^{1b})_{q3}$-$G^{1d}$, or $G^{1d}$ wherein $R^{1a}$, $R^{1b}$, q3, and $G^{1d}$ are as set forth in the Summary and herein. For example, certain embodiments are directed to those wherein $G^{1d}$ is phenyl or monocyclic heteroaryl (including but not limited to, pyridinyl), each of which is optionally substituted as described in the Summary. $R^{1a}$ and $R^{1b}$ are, for example, each independently hydrogen or $C_1$-$C_4$ alkyl. In certain embodiments, $A^1$ is —$N(R^b)(R^c)$ wherein $R^b$ is hydrogen or $C_1$-$C_4$ alkyl and $R^c$ is $C_1$-$C_4$ alkyl.

In certain embodiments, $A^1$ is —$N=C(R^p)(R^q)$ wherein $R^p$ and $R^q$ are as described generally in the Summary and herein. For example, certain embodiments are directed to those wherein $R^p$ is alkyl (e.g. $C_1$-$C_4$ alkyl such as but not limited to, tert-butyl, isopropyl, methyl, ethyl), haloalkyl (e.g. $C_1$-$C_4$ haloalkyl such as, but not limited to, trifluoromethyl), —$C(O)OR^d$, —$C(O)R^d$, or $G^{1d}$; and $R^q$ is hydrogen, alkyl (e.g. $C_1$-$C_4$ alkyl such as but not limited to, methyl, ethyl, isopropyl), haloalkyl (e.g. $C_1$-$C_4$ haloalkyl such as, but not limited to, trifluoromethyl), or —$N(R^b)(R^c)$. In certain embodiments, $R^p$ is alkyl (e.g. $C_1$-$C_4$ alkyl such as but not limited to, tert-butyl, isopropyl, methyl, ethyl), haloalkyl (e.g. $C_1$-$C_4$ haloalkyl such as, but not limited to, trifluoromethyl), or —$C(O)R^d$; and $R^q$ is alkyl (e.g. $C_1$-$C_4$ alkyl such as but not limited to, methyl, ethyl, isopropyl) or haloalkyl (e.g. $C_1$-$C_4$ haloalkyl such as, but not limited to, trifluoromethyl). $R^d$, $G^{1d}$, $R^b$, and $R^c$ are as described in the Summary and embodiments herein. $R^d$, for example, is alkyl (e.g. $C_1$-$C_4$ alkyl such as but not limited to, methyl, ethyl). $G^{1d}$, for example, is phenyl, monocyclic heteroaryl (e.g. pyridinyl), or monocyclic cycloalkyl (e.g. cyclopropyl), each of which is optionally substituted as described in the Summary. $R^b$ and $R^c$, for example, are hydrogen.

In certain embodiments wherein $A^1$ is —$N=C(R^p)(R^q)$, $R^p$ and $R^q$, together with the carbon atom to which they are attached, form a monocyclic 5-, 6-, and 7-membered cycloalkyl or heterocycle ring, optionally substituted as described in the Summary. For example, said monocyclic ring is azepanyl or cyclopentyl, each of which is optionally substituted.

$R^2$ has values as described generally in the Summary.

Certain compounds include, but are not limited to, those wherein $R^2$ is —$(CR^{2a}R^{2b})_{q5}$-$G^2$ or —$(CR^{2a}R^{2b})_{q4}$—O-alkyl wherein $G^2$, $R^{2a}$, $R^{2b}$, q4 and q5 are as described generally in the Summary and in embodiments herein below.

Certain compounds include, but are not limited to, those wherein $R^2$ is —$(CR^{2a}R^{2b})_{q5}$-$G^2$; and $G^2$ is as described generally in the Summary and herein below. For example, $G^2$ is a 4-, 5-, 6-, or 7-membered monocyclic heterocycle containing zero or one double bond, one or two oxygen, and zero or one nitrogen as ring atoms; or $G^2$ is furanyl, oxazolyl, isoxazolyl, or oxadiazolyl. Each $G^2$ is independently unsubstituted or substituted with 1, 2, 3, 4, 5, or 6 substituents independently selected from the group consisting of oxo, alkyl, halo, —OH, alkoxy, and haloalkyl. $R^{2a}$, $R^{2b}$, and q5 are as described in the Summary and in embodiments herein. $R^{2a}$ and $R^{2b}$ are, for example, hydrogen or $C_1$-$C_4$ alkyl (e.g. methyl). In certain embodiments, $R^{2a}$ and $R^{2b}$ are hydrogen. q5, for example, is 1 or 2. In certain embodiments, q5 is 1. $G^2$, for example, is tetrahydrofuranyl such as, but not limited to, tetrahydrofuran-2-yl, optionally substituted as described above. In certain embodiments, $R^2$ is —$(CH_2)$-$G^2$ and $G^2$ is as described in the Summary and embodiments herein.

Certain embodiments include, but are not limited to, those wherein $R^2$ is —$(CR^{2a}R^{2b})_{q4}$—OH, —$(CR^{2a}R^{2b})_{q4}$—O-alkyl, or —$(CR^{2a}R^{2b})_{q4}$—O—$(CR^{2c}R^{2d})_{q3}$—O-alkyl. In certain embodiments, $R^2$ is —$(CR^{2a}R^{2b})_{q4}$—O-alkyl. $R^{2a}$, $R^{2b}$, q4 and q3 are as described generally in the Summary and in embodiments herein. For example, $R^{2a}$ and $R^{2b}$ are hydrogen. q4, for example, is 2 or 3. In certain embodiments, $R^2$ is —$(CH_2)_2$—O—$CH_3$.

$R^x$ and z have values as described generally in the Summary. In certain embodiments, $R^x$ is $G^{1d}$, alkyl, alkenyl, alkynyl, halo, haloalkyl, CN or $OR^f$ wherein $G^{1d}$ and $R^f$ are as disclosed in the Summary, and z is 0, 1, or 2. In yet other embodiments, $R^x$ is alkyl, halo, haloalkyl, or CN, and z is 1.

Accordingly, one aspect is directed to groups of compounds of formula (I) wherein $X^1$ is O or $N(R^{bx})$; $R^3$ and $R^4$ are each independently $G^3$, hydrogen, alkyl, alkenyl, alkynyl, —CN, halo, —$OR^h$, haloalkyl, —$(CR^{3a}R^{3b})_{q6}$—$OR^h$, or —$(CR^{3a}R^{3b})_{q6}$—$N(R^h)_2$, $A^1$ is —$(CR^{1a}R^{1b})_{q1}$-$G^{1c}$, —$(CR^{1a}R^{1b})_{q1}$-$A^2$, —$N(R^b)C(O)R^a$, —$N(R^b)C(O)OR^d$, —$N(R^b)(R^c)$, or —$N$=$C(R^p)(R^q)$; and $R^{bx}$, $R^{1a}$, $R^{1b}$, q1, $G^{1c}$, $A^2$, $R^p$, $R^q$, $R^b$, $R^a$, $R^d$, $R^c$, $G^3$, $R^{3a}$, q6, and $R^h$ are as described generally in the Summary and in the embodiments as described herein above. In certain embodiments, $X^1$ is O. In other embodiments, $X^1$ is $N(R^{bx})$.

Another aspect is directed to groups of compounds of formula (I) wherein $X^1$ is O or $N(R^{bx})$; $R^3$ and $R^4$ are each independently $G^3$, hydrogen, alkyl, alkenyl, alkynyl, —CN, halo, —$OR^h$, haloalkyl, —$(CR^{3a}R^{3b})_{q6}$—$OR^h$, or —$(CR^{3a}R^{3b})_{q6}$—$N(R^h)_2$; $A^1$ is $G^{1a}$-$G^{1b}$; and $R^{bx}$, $G^{1a}$, $G^{1b}$, $G^3$, $R^{3a}$, $R^{3b}$, q6, and $R^h$ are as described generally in the Summary and in the specific embodiments as described herein above. In certain embodiments, $X^1$ is O. In other embodiments, $X^1$ is $N(R^{bx})$.

Another aspect is directed to groups of compounds of formula (I) wherein $X^1$ is O or $N(R^{bx})$; $R^3$ and $R^4$ are each independently $G^3$, hydrogen, alkyl, alkenyl, alkynyl, —CN, halo, —$OR^h$, haloalkyl, —$(CR^{3a}R^{3b})_{q6}$—$OR^h$, or —$(CR^{3a}R^{3b})_{q6}$—$N(R^h)_2$, $A^1$ is —$(CR^{1a}R^{1b})_{q1}$-$G^{1c}$; and $R^{bx}$, $G^{1c}$, $R^{1a}$, $R^{1b}$, q1, $G^3$, $R^{3a}$, $R^{3b}$, q6, and $R^h$ are as described generally in the Summary and in the embodiments as described herein above. In certain embodiments, $X^1$ is O. In other embodiments, $X^1$ is $N(R^{bx})$.

Yet another aspect is directed to groups of compounds of formula (I) wherein $X^1$ is O or $N(R^{bx})$; $R^3$ and $R^4$ are each independently $G^3$, hydrogen, alkyl, alkenyl, alkynyl, —CN, halo, —$OR^h$, haloalkyl, —$(CR^{3a}R^{3b})_{q6}$—$OR^h$, or —$(CR^{3a}R^{3b})_{q6}$—$N(R^h)_2$, and $A^1$ is —$(CR^{1a}R^{1b})_{q1}$-$A^2$; and $R^{bx}$, $A^2$, $R^{1a}$, $R^{1b}$, q1, $G^3$, $R^{3a}$, $R^{3b}$, q6, and $R^h$ are as described generally in the Summary and in the embodiments as described herein above. In certain embodiments, $X^1$ is O. In other embodiments, $X^1$ is $N(R^{bx})$.

Yet another aspect is directed to groups of compounds of formula (I) wherein $X^1$ is O or $N(R^{bx})$; $R^3$ and $R^4$ are each independently $G^3$, hydrogen, alkyl, alkenyl, alkynyl, —CN, halo, —$OR^h$, haloalkyl, —$(CR^{3a}R^{3b})_{q6}$—$OR^h$, or —$(CR^{3a}R^{3b})_{q6}$—$N(R^h)_2$, and $A^1$ is —$(CR^{1a}R^{1b})_{q1}$—OH; and $R^{bx}$, $R^{1a}$, $R^{1b}$, q1, $G^3$, $R^{3a}$, $R^{3b}$, q6, and $R^h$ are as described generally in the Summary and in the embodiments as described herein above. In certain embodiments, $X^1$ is O. In other embodiments, $X^1$ is $N(R^{bx})$.

Yet another aspect of the invention is directed to groups of compounds of formula (I) wherein $X^1$ is O or $N(R^{bx})$; $R^3$ and $R^4$ are each independently $G^3$, hydrogen, alkyl, alkenyl, alkynyl, —CN, halo, —$OR^h$, haloalkyl, —$(CR^{3a}R^{3b})_{q6}$—$OR^h$, or —$(CR^{3a}R^{3b})_{q6}$—$N(R^h)_2$, $A^1$ is —$N(R^b)C(O)R^a$, —$N(R^b)C(O)OR^d$, —$N(R^b)C(O)N(R^b)(R^c)$, —$N(R^b)(R^c)$, or —$N$=$C(R^p)(R^q)$; and $R^{bx}$, $R^a$, $R^b$, $R^c$, $R^d$, $R^p$, $R^q$, $G^3$, $R^{3a}$, $R^{3b}$, q6, and $R^h$ are as described generally in the Summary and in the embodiments as described herein above. In certain embodiments, $X^1$ is O. In other embodiments, $X^1$ is $N(R^{bx})$.

Yet another aspect of the invention is directed to groups of compounds of formula (I) wherein $X^1$ is O or $N(R^{bx})$; $R^3$ and $R^4$ are each independently $G^3$, hydrogen, alkyl, alkenyl, alkynyl, —CN, halo, —$OR^h$, haloalkyl, —$(CR^{3a}R^{3b})_{q6}$—$OR^h$, or —$(CR^{3a}R^{3b})_{q6}$—$N(R^h)_2$, $A^1$ is —$N(R^b)C(O)R^a$, —$N(R^b)C(O)OR^d$, or —$N(R^b)C(O)N(R^b)(R^c)$, and $R^{bx}$, $R^a$, $R^b$, $R^c$, $R^d$, $G^3$, $R^{3a}$, $R^{3b}$, q6, and $R^h$ are as described generally in the Summary and in the embodiments as described herein above. In certain embodiments, $X^1$ is O. In other embodiments, $X^1$ is $N(R^{bx})$.

Yet another aspect is directed to groups of compounds of formula (I) wherein $X^1$ is O or $N(R^{bx})$; $R^3$ and $R^4$ are each independently $G^3$, hydrogen, alkyl, alkenyl, alkynyl, —CN, halo, —$OR^h$, haloalkyl, —$(CR^{3a}R^{3b})_{q6}$—$OR^h$, or —$(CR^{3a}R^{3b})_{q6}$—$N(R^h)_2$, $A^1$ is $N(R^b)(R^c)$, and $R^{bx}$, $R^b$, $R^c$, $G^3$, $R^{3a}$, $R^{3b}$, q6, and $R^h$ are as described generally in the Summary and in the embodiments as described herein above. In certain embodiments, $X^1$ is O. In other embodiments, $X^1$ is $N(R^{bx})$.

Yet another aspect is directed to groups of compounds of formula (I) wherein $X^1$ is O or $N(R^{bx})$; $R^3$ and $R^4$ are each independently $G^3$, hydrogen, alkyl, alkenyl, alkynyl, —CN, halo, —$OR^h$, haloalkyl, —$(CR^{3a}R^{3b})_{q6}$—$OR^h$, or —$(CR^{3a}R^{3b})_{q6}$—$N(R^h)_2$, $A^1$ is —$N$=$C(R^p)(R^q)$, and $R^{bx}$, $R^p$, $R^q$, $G^3$, $R^{3a}$, $R^{3b}$, q6, and $R^h$ are as described generally in the Summary and in the embodiments as described herein above. In certain embodiments, $X^1$ is O. In other embodiments, $X^1$ is $N(R^{bx})$.

A further aspect is directed to groups of compounds of formula (I) wherein $X^1$ is O or $N(R^{bx})$; $R^3$ and $R^4$, together with the carbon atoms to which they are attached, form a ring as described in the Summary and in the embodiments as described herein above, $A^1$ is —$(CR^{1a}R^{1b})_{q1}$-$G^{1c}$, —$(CR^{1a}R^{1b})_{q1}$-$A^2$, —$N(R^b)C(O)R^a$, —$N(R^b)C(O)OR^d$, —$N(R^b)(R^c)$, or —$N$=$C(R^p)(R^q)$; $R^{bx}$, $R^{1a}$, $R^{1b}$, q1, $G^{1c}$, $A^2$, $R^p$, $R^q$, $R^a$, $R^b$, $R^d$, and $R^c$ are as described generally in the Summary and in the specific embodiments as described herein above. In certain embodiments, $X^1$ is O. In other embodiments, $X^1$ is $N(R^{bx})$.

Yet other aspect is directed to groups of compounds of formula (I) wherein $X^1$ is O or $N(R^{bx})$; $R^3$ and $R^4$, together with the carbon atoms to which they are attached, form a ring as described in the Summary and in the embodiments as described herein above, $A^1$ is -$G^{1a}$-$G^{1b}$; and $R^{bx}$, $G^{1a}$, and $G^{1b}$ are as described generally in the Summary and in the specific embodiments as described herein above. In certain embodiments, $X^1$ is O. In other embodiments, $X^1$ is $N(R^{bx})$.

Another aspect is directed to groups of compounds of formula (I) wherein $X^1$ is O or $N(R^{bx})$; $R^3$ and $R^4$, together with the carbon atoms to which they are attached, form a ring as described in the Summary and in the embodiments as described herein above, $A^1$ is —$(CR^{1a}R^{1b})_{q1}$-$G^{1c}$; and $R^{bx}$, $G^{1c}$, $R^{1a}$, $R^{1b}$, and q1 are as described generally in the Summary and in the specific embodiments as described herein above. In certain embodiments, $X^1$ is O. In other embodiments, $X^1$ is $N(R^{bx})$.

Yet another aspect of the invention is directed to groups of compounds of formula (I) wherein $X^1$ is O or $N(R^{bx})$; $R^3$ and $R^4$, together with the carbon atoms to which they are attached, form a ring as described in the Summary and in the embodiments as described herein above, and $A^1$ is —$(CR^{1a}R^{1b})_{q1}$-$A^2$; and $R^{bx}$, $A^2$, $R^{1a}$, $R^{1b}$, and q1 are as described generally in the Summary and in the specific embodiments as described herein above. In certain embodiments, $X^1$ is O. In other embodiments, $X^1$ is $N(R^{bx})$.

Yet another aspect of the invention is directed to groups of compounds of formula (I) wherein $X^1$ is O or $N(R^{bx})$; $R^3$ and $R^4$, together with the carbon atoms to which they are attached, form a ring as described in the Summary and in the embodiments as described herein above, and $A^1$ is —$(CR^{1a}R^{1b})_{q1}$—OH; and $R^{bx}$, $R^{1a}$, $R^{1b}$, and q1 are as described generally in the Summary and in the specific embodiments as described herein above. In certain embodiments, $X^1$ is O. In other embodiments, $X^1$ is $N(R^{bx})$.

Yet another aspect is directed to groups of compounds of formula (I) wherein $X^1$ is O or $N(R^{bx})$; $R^3$ and $R^4$ together with the carbon atoms to which they are attached, form a ring as described in the Summary and in the embodiments as described herein above, $A^1$ is —$N(R^b)C(O)R^a$, —$N(R^b)C(O)OR^d$, —$N(R^b)C(O)N(R^b)(R^c)$, —$N(R^b)(R^c)$, or N=$C(R^p)(R^q)$; and $R^{bx}$, $R^a$, $R^b$, $R^c$, $R^d$, $R^p$, and $R^q$ are as described generally in the Summary and in the embodiments as described herein above. In certain embodiments, $X^1$ is O. In other embodiments, $X^1$ is $N(R^{bx})$.

Yet another aspect is directed to groups of compounds of formula (I) wherein $X^1$ is O or $N(R^{bx})$; $R^3$ and $R^4$, together with the carbon atoms to which they are attached, form a ring as described in the Summary and in the embodiments as described herein above, $A^1$ is —$N(R^b)C(O)R^a$, —$N(R^b)C(O)OR^d$, or —$N(R^b)C(O)N(R^b)(R^c)$, and $R^{bx}$, $R^a$, $R^b$, $R^c$, and $R^d$ are as described generally in the Summary and in the embodiments as described herein above. In certain embodiments, $X^1$ is O. In other embodiments, $X^1$ is $N(R^{bx})$. Yet another aspect is directed to groups of compounds of formula (I) wherein $X^1$ is O or $N(R^{bx})$; $R^3$ and $R^4$, together with the carbon atoms to which they are attached, form a ring as described in the Summary and in the embodiments as described herein above, $A^1$ is —$N(R^b)(R^c)$, and $R^{bx}$, $R^b$, and $R^c$ are as described generally in the Summary and in the embodiments as described herein above. In certain embodiments, $X^1$ is O. In other embodiments, $X^1$ is $N(R^{bx})$.

Yet another aspect is directed to groups of compounds of formula (I) wherein $X^1$ is O or $N(R^{bx})$; $R^3$ and $R^4$, together with the carbon atoms to which they are attached, form a ring as described in the Summary and in the embodiments as described herein above, $A^1$ is —N=$C(R^p)(R^q)$, and $R^{bx}$, $R^p$, and $R^q$ are as described generally in the Summary and in the embodiments as described herein above. In certain embodiments, $X^1$ is O. In other embodiments, $X^1$ is $N(R^{bx})$.

Yet a further aspect is directed to groups of compounds of formula (II)

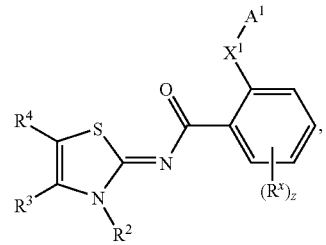

(II)

wherein $X^1$, $A^1$, $R^2$, $R^3$, $R^4$, $R^x$, and z are as described in the Summary and in the embodiments described above for formula (I). Combinations of the embodiments for the variables $X^1$, $A^1$, $R^2$, $R^3$, $R^4$, $R^x$, and z of formula (I) are also contemplated for formula (II).

For each group and subgroup of compounds of formula (I) and (II) described above, $R^2$ has values as described in the Summary and in the embodiments described herein above.

Thus, for each group of compounds of formula (I) or (II) as described above, examples of a subgroup include, but not limited to, those wherein $R^2$ is —$(CR^{2a}R^{2b})_{q4}$—O-alkyl or —$(CR^{2a}R^{2b})_{q5}$-$G^2$; and $G^2$ is as described in the Summary and embodiments herein above. For example, $G^2$ is a 4-, 5-, 6-, or 7-membered monocyclic heterocycle containing zero or one double bond, one or two oxygen, and zero or one nitrogen as ring atoms; or $G^2$ is furanyl, oxazolyl, isoxazolyl, or oxadiazolyl; and each $G^2$ is independently unsubstituted or substituted with 1, 2, 3, 4, 5, or 6 substituents independently selected from the group consisting of oxo, alkyl, halo, —OH, alkoxy, and haloalkyl, $R^{2a}$, $R^{2b}$, q4 and q5 are as described in the Summary and in the embodiments described herein above. In certain embodiments, q4 is 2 or 3.

Examples of another subgroup include, but not limited to, those wherein $R^2$ is —$(CR^{2a}R^{2b})_{q5}$-$G^2$; and $G^2$, $R^{2a}$, $R^{2b}$, and q5 is as described in the Summary and the embodiments herein. In certain embodiments, q5 is 1 or 2. In yet other embodiments, q5 is 1.

Yet other examples of a subgroup include, but not limited to, those wherein $R^2$ is —$(CR^{2a}R^{2b})_{q4}$—OH, —$(CR^{2a}R^{2b})_{q4}$—O-alkyl, or —$(CR^{2a}R^{2b})_{q4}$—O—$(CR^{2c}R^{2d})_{q3}$—O-alkyl. $R^{2a}$, $R^{2b}$, $R^{2c}$, $R^{2d}$, q4, and q3 are as described in the Summary and embodiments herein above.

Yet other examples of a subgroup include, but not limited to, those wherein $R^2$ is —$(CR^{2a}R^{2b})_{q4}$—O-alkyl wherein $R^{2a}$, $R^{2b}$, and q4 are as described in the Summary and embodiments herein above. In certain embodiments, $R^2$ is —$(CH_2)_2$—O—$CH_3$.

Examples of a further subgroup include, but not limited to, those wherein $R^2$ is —$(CH_2)_2$—O—$CH_3$ or —$(CH_2)$-$G^2$; and $G^2$ is as described in the Summary and embodiments herein. In certain embodiments, $G^2$ is optionally substituted tetrahydrofuranyl (e.g. tetrahydrofuran-2-yl).

Within each groups and subgroups of compounds of formula described above, $R^x$ and z have values as disclosed in the Summary and in the embodiments described above.

Thus, compounds comprised herein are groups and subgroups of compounds of formula (I) or (II) as described above in which $R^x$ is $G^{1d}$, alkyl, alkenyl, alkynyl, halo, haloalkyl, CN or $OR^f$ wherein $G^{1d}$ and $R^f$ are as disclosed in the Summary, and in the embodiments described herein above, and z is 0, 1, or 2. In certain embodiments, $R^x$ is alkyl, halo, haloalkyl, or CN, and z is 1.

Specific embodiments of compounds contemplated include, but are not limited to:

2-[(2R)-azetidin-2-ylmethoxy]-N-[(2Z)-5-tert-butyl-3-[(2R)-tetrahydrofuran-2-ylmethyl]-1,3-thiazol-2(3H)-ylidene]-5-(trifluoromethyl)benzamide;

2-[(2S)-azetidin-2-ylmethoxy]-N-[(2Z)-5-tert-butyl-3-[(2R)-tetrahydrofuran-2-ylmethyl]-1,3-thiazol-2(3H)-ylidene]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S)-1-methylazetidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(2S)-piperidin-2-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S)-1-methylpiperidin-2-yl]methoxy}-5-(trifluoromethyl)benzamide ;

N-[(2Z)-5-tert-butyl-3-[(2R)-tetrahydrofuran-2-ylmethyl]-1,3-thiazol-2(3H)-ylidene]-2-[(2R)-piperidin-2-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2R)-1-methylpiperidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2R)-1-methylazetidin-2-yl]methoxy}-5-(trifluoromethyl)benzamide;

2-(azetidin-3-ylmethoxy)-N-[(2Z)-5-tert-butyl-3-[(2R)-tetrahydrofuran-2-ylmethyl]-1,3-thiazol-2(3H)-ylidene]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(3R)-piperidin-3-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(3R)-1-methylpiperidin-3-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(1-methylazetidin-3-yl)methoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(3S)-piperidin-3-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(3S)-1-methylpiperidin-3-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(1-methylpiperidin-4-yl)methoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-(piperidin-4-ylmethoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(1-methyl-1H-imidazol-5-yl)methoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-(pyridin-2-ylmethoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-(pyrazin-2-ylmethoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(1-oxidopyridin-2-yl)methoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-(pyridin-3-ylmethoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(2R)-tetrahydrofuran-2-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(2S)-tetrahydrofuran-2-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S)-1-methylpyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(2R)-pyrrolidin-2-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2R)-1-methylpyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[2-(1-methylpyrrolidin-2-yl)ethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(3R)-pyrrolidin-3-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(3S)-pyrrolidin-3-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(3R)-1-methylpyrrolidin-3-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(3S)-1-methylpyrrolidin-3-yl]methoxy}-5-(trifluoromethyl)benzamide;

2-[(4-benzylmorpholin-2-yl)methoxy]-N-[(2Z)-5-tert-butyl-3-[(2S)-tetrahydrofuran-2-ylmethyl]-1,3-thiazol-2(3H)-ylidene]-5-(trifluoromethyl)benzamide;

2-{[(2R)-2-amino-3-hydroxypropyl]oxy}-N-[(2Z)-5-tert-butyl-3-[(2S)-tetrahydrofuran-2-ylmethyl]-1,3-thiazol-2(3H)-ylidene]-5-(trifluoromethyl)benzamide;

N-[(2Z)-5-tert-butyl-3-[(2S)-tetrahydrofuran-2-ylmethyl]-1,3-thiazol-2(3H)-ylidene]-2-[(1,4-dimethylpiperazin-2-yl)methoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{2-[methyl(phenyl)amino]ethoxy}-5-(trifluoromethyl)benzamide;

2-(benzyloxy)-N-[(2Z)-5-tert-butyl-3-[(2R)-tetrahydrofuran-2-ylmethyl]-1,3-thiazol-2(3H)-ylidene]-5-(trifluoromethyl)benzamide;

N-[(2Z)-5-tert-butyl-3-[(2R)-tetrahydrofuran-2-ylmethyl]-1,3-thiazol-2(3H)-ylidene]-2-(1,3-oxazol-5-ylmethoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-(1,3-thiazol-2-ylmethoxy)-5-(trifluoromethyl)benzamide;

2-(2-tert-butylhydrazino)-N-[(2Z)-5-tert-butyl-3-[(2R)-tetrahydrofuran-2-ylmethyl]-1,3-thiazol-2(3H)-ylidene]-5-(trifluoromethyl)benzamide;

tert-butyl 2-[2-({[(2Z)-5-tert-butyl-3-[(2R)-tetrahydrofuran-2-ylmethyl]-1,3-thiazol-2(3H)-ylidene]amino}carbonyl)-4-(trifluoromethyl)phenyl]hydrazinecarboxylate;

N-[(2Z)-5-tert-butyl-3-(2-methoxyethyl)-1,3-thiazol-2(3H)-ylidene]-2-(pyrazin-2-ylmethoxy)-5-(trifluoromethyl)benzamide;

N-[(2Z)-5-tert-butyl-3-(2-methoxyethyl)-1,3-thiazol-2(3H)-ylidene]-2-(pyridin-2-ylmethoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S)-1-methyl-5-oxopyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(2S)-pyrrolidin-2-yl-methoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S)-1-ethylpyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S)-1-isopropylpyrrolidin-2-yl]methoxy}-5-(trifluoromethyl)benzamide;

2-{[(2S)-1-acetylpyrrolidin-2-yl]methoxy}-N-[(2Z)-5-tert-butyl-3-[(2R)-tetrahydrofuran-2-ylmethyl]-1,3-thiazol-2(3H)-ylidene]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S)-1-(methylsulfonyl)pyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(2R)-(1-methyl-1-oxidopyrrolidin-2-yl)methoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-(3-hydroxy-3-methylbutoxy)-5-(trifluoromethyl)benzamide;

N-[(2Z)-3-(2-methoxyethyl)-5-methyl-1,3-thiazol-2(3H)-ylidene]-2-{[(2S)-1-methylpyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S,4S)-4-fluoro-1-methylpyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S,4R)-4-fluoro-1-methylpyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-({[(2S)-1-methylpyrrolidin-2-yl]methyl}amino)-5-(trifluoromethyl)benzamide;

N-[(2Z)-5-tert-butyl-3-[(2R)-tetrahydrofuran-2-ylmethyl]-1,3-thiazol-2(3H)-ylidene]-2-(1H-pyrazol-5-ylmethoxy)-5-(trifluoromethyl)benzamide;

N-[(2Z)-4-tert-butyl-3-[(2R)-tetrahydrofuran-2-ylmethyl]-1,3-thiazol-2(3H)-ylidene]-2-{[(2S)-1-methylpyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-{2-[(2-hydroxyethyl)amino]ethoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-5-cyano-2-{[(2S)-1-methylpyrrolidin-2-yl]methoxy}benzamide;

N-[(2Z)-4,5-dimethyl-3-[(2R)-tetrahydrofuran-2-ylmethyl]-1,3-thiazol-2(3H)-ylidene]-2-{[(2S)-1-methylpyrrolidin-2-yl]methoxy}-5-(trifluoromethyl)benzamide;

N-[(2Z)-5-tert-butyl-4-methyl-3-[(2R)-tetrahydrofuran-2-ylmethyl]-1,3-thiazol-2(3H)-ylidene]-2-{[(2S)-1-methylpyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(3S)-morpholin-3-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-({2-[(tetrahydro-2H-pyran-2-yloxy)imino]propyl}oxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-({(2R)-3-hydroxy-2-[(trifluoroacetyl)amino]propyl}oxy)-5-(trifluoromethyl)benzamide;

2-[(tert-butylamino)oxy]-N-[(2Z)-5-tert-butyl-3-[(2R)-tetrahydrofuran-2-ylmethyl]-1,3-thiazol-2(3H)-ylidene]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(2S)-morpholin-2-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(1-methyl-1H-imidazol-5-yl)methoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(1-methyl-1H-imidazol-4-yl)methoxy]-5-(trifluoromethyl)benzamide;

2-{[(2R)-2-amino-3-hydroxypropyl]oxy}-N-[(2Z)-5-tert-butyl-3-[(2R)-tetrahydrofuran-2-ylmethyl]-1,3-thiazol-2(3H)-ylidene]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2Z)-2-(hydroxyimino)-3,3-dimethylbutyl]oxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2E)-2-(hydroxyimino)-3,3-dimethylbutyl]oxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-(3,3-dimethyl-2-oxobutoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[2-(hydroxyimino)propyl]oxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[2-methyl-2-(1H-pyrrol-1-yl)propoxy]-5-(trifluoromethyl)benzamide;

2-[(acetylamino)oxy]-N-[(2Z)-5-tert-butyl-3-[(2R)-tetrahydrofuran-2-ylmethyl]-1,3-thiazol-2(3H)-ylidene]-5-(trifluoromethyl)benzamide;

2-[(tert-butylamino)oxy]-N-[(2Z)-5-tert-butyl-3-(2-methoxyethyl)-1,3-thiazol-2(3H)-ylidene]-5-(trifluoromethyl)benzamide;

N-[(2Z)-5-tert-butyl-3-[(2R)-tetrahydrofuran-2-ylmethyl]-1,3-thiazol-2(3H)-ylidene]-2-({(2S)-1-[2-(hydroxyimino)propyl]pyrrolidin-2-yl}methoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(diethylamino)oxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(isopropylamino)oxy]-5-(trifluoromethyl)benzamide;

N-[(2Z)-5-tert-butyl-3-[(2R)-tetrahydrofuran-2-ylmethyl]-1,3-thiazol-2(3H)-ylidene]-5-(trifluoromethyl)-24 {[2,2,2-trifluoro-1-methylethylidene]amino}oxy)benzamide;

N-[(2Z)-5-tert-butyl-3-[(2R)-tetrahydrofuran-2-ylmethyl]-1,3-thiazol-2(3H)-ylidene]-2-{[(2R)-2-hydroxypropyl]oxy}-5-(trifluoromethyl)benzamide;

2-{[2-(tert-butoxyimino)propyl]oxy}-N-[(2Z)-5-tert-butyl-3-[(2R)-tetrahydrofuran-2-ylmethyl]-1,3-thiazol-2(3H)-ylidene]-5-(trifluoromethyl)benzamide;

N-[(2Z)-5-tert-butyl-3-(tetrahydrofuran-2-ylmethyl)-1,3-thiazol-2(3H)-ylidene]-2-[(cyclopentylideneamino)oxy]-5-(trifluoromethyl)benzamide; and N-[(2Z)-5-tert-butyl-3-[(2R)-tetrahydrofuran-2-ylmethyl]-1,3-thiazol-2(3H)-ylidene]-2-({[1-methyl-2-oxopropylidene]amino}oxy)-5-(trifluoromethyl)benzamide;

or pharmaceutically acceptable salts or solvates thereof.

Compounds of the present application may exist as stereoisomers where asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the present compounds. The invention contemplates various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium (2H), tritium (3H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7531685; 7528131; 7521421; 7514068; 7511013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of CB2 ligands in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999).

In addition, non-radio active isotope containing drugs, such as deuterated drugs called "heavy drugs," can be used for the treatment of diseases and conditions related to CB2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D Metal., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling 0 Eds. 1994. Advanced Medical Publishing, Madison Wis. pp. 125-134; Diabetes Metab. 23: 251 (1997)).

Stable isotope labeling of a drug may alter its physicochemical properties such as pKa and lipid solubility. These effects and alterations may affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-istopic compound.

c. BIOLOGICAL DATA (i) In Vitro Methods:

$CB_2$ and $CB_1$ Radioligand Binding Assays:

The $CB_1$ and $CB_2$ radioligand binding assays described herein are utilized to ascertain the affinity of compounds of the present application for binding to $CB_2$ relative to $CB_1$ receptors.

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 µg/well for human $CB_2$) into wells of a deep well plate containing [$^3$H]CP 55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 µL/well of cold assay buffer followed by rapid vacuum filtration through a UniFilter-96 GF/C filter plates (pre-soaked in 1 mg/mL BSA for 2 hours). The bound activity was counted in a Top-Count using Microscint-20. Saturation experiments were conducted with twelve concentrations of [$^3$H]CP 55,940 ranging from 0.01 to 8 nM. Competition experiments were conducted with 0.5 nM [$^3$H]CP 55,940 and five concentrations (0.01 nM to 10 µM) of displacing ligands. The addition of 10 µM unlabeled CP 55,940 (Tocris, Ellisville, Mo.) was used to assess nonspecific binding.

HEK293 cells stably expressing rat $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 20 µg/well for rat $CB_2$) into wells of a deep well plate containing [$^3$H]CP 55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 45 min incubation at 30° C., binding reaction was terminated by the addition of 300 µl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP 55,940 ranging from 0.01 to 8 nM. Competition experiments were conducted with 0.5 nM [$^3$H] CP 55,940 and five concentrations of displacing ligands selected from the range of 0.01 nM to 10 µM. The addition of 10 µM unlabeled CP 55,940 (Tocris, Ellisville, Mo.) was used to assess nonspecific binding.

Compounds tested with the above assay have equilibrium dissociation constants ($K_i$) of less than about 1,000 nM, for example, less than about 400 nM, or less than about 200 nM, or less than about 100 nM.

HEK293 human $CB_1$ membranes were purchased from Perkin Elmer. Binding was initiated by the addition of membranes (8-12 µg per well) into wells (Scienceware 96-well DeepWell plate, VWR, West Chester, Pa.) containing [$^3$H]CP 55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 µL. After incubation (30° C. for 90 minutes), binding was terminated by the addition of 300 µL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP 55,940 and five concentrations (1 nM to 10 µM) of displacing ligands. The addition of 10 µM unlabeled CP 55,940 (Tocris, Ellisville, Mo.) was used to assess nonspecific binding. Compounds tested exhibit about 10×-1000× weaker binding affinity for $CB_1$ receptors than for $CB_2$. These results show that the compounds tested preferably bind to $CB_2$ receptors, therefore are selective ligands for the $CB_2$ receptor.

$CB_2$ and $CB_1$ Cyclase Functional Assays:

The cyclase functional assays were performed using the HitHunter™ cAMP assay kit from DiscoveRx (Fremont, Calif.) according to vendor's protocol. Briefly, HEK cells expressing $CB_2$ or $CB_1$ receptors (rat or human) were detached using cell dissociation buffer (Invitrogen, Carlsbad, Calif.), dispersed and placed in suspension at 10,000 cells per well in 96 well plates prior to the assay. Cell suspensions were incubated at 37° C. for 20 min with variable concentrations of test ligands and or 10 µM CP 55,940-positive control in the presence of a fixed concentration of forskolin (18 µM for rat $CB_2$ and 37 µM for rat $CB_1$) in Dulbescco's phosphate-buffered saline (Invitrogen, Carlsbad, Calif.) supplemented with bovine serum albumin (0.01% final concentration). The reactions were terminated by the addition of lysis buffer and the luminescence was detected following the procedure according to the manufacturer's instructions. $EC_{50}$ values were calculated using sigmoidal dose-response curve fitting from Prism (GraphPad). Compounds tested are more potent at activating $CB_2$ vs. $CB_1$ receptors in the described cyclase assays (Table 1).

TABLE 1

| Example | human $CB_2$ ($K_i$, nM) | rat $CB_2$ ($K_i$, nM) | rat $CB_2$ cyclase ($EC_{50}$, nM) | $rCB_1$ cyclase ($EC_{50}$, nM) |
|---|---|---|---|---|
| 1 | 115 | 15 | 2.26 | 9331 |
| 2 | 15 | 3.0 | 0.64 | 3237 |
| 3 | 7.4 | 4.5 | 0.09 | 1020 |
| 4 | 0.7 | 0.6 | 0.40 | 395 |
| 5 | 0.7 | 1.4 | 0.15 | 612 |
| 6 | 30 | 14 | 0.40 | 4499 |
| 7 | 33 | 19 | 0.38 | 4698 |
| 8 | 47 | 17 | 0.35 | 3681 |
| 12 | 208 | 28 | 2.07 | 10793 |
| 15 | 1000 | 83 | 6.26 | 13029 |
| 17 | 53 | 15 | 2.75 | >27000 |
| 18 | 20 | 6 | 1.02 | >27000 |
| 19 | 5 | 5 | 0.41 | 3390 |
| 20 | 209 | 51 | 0.47 | 7984 |
| 21 | 13 | 10 | 0.21 | 6217 |
| 22 | 3.0 | 0.5 | 0.07 | 3231 |
| 23 | 0.5 | 0.3 | 0.14 | 941 |
| 24 | 4.6 | 3.4 | 0.09 | 1991 |
| 26 | 206 | 70 | 2.18 | 11242 |
| 30 | 141 | 29 | 4.98 | 12084 |
| 31 | 92 | 84 | 3.58 | 10723 |
| 33 | 7.4 | 2.8 | 0.18 | 1172 |
| 34 | 25 | 13 | 0.30 | 4087 |
| 35 | 14 | 6.5 | 6.31 | 9485 |
| 36 | 6.0 | 2.9 | 1.47 | 6561 |
| 37 | 26 | 9.0 | 0.50 | 7549 |
| 38 | 5.5 | 2.5 | 0.33 | 1996 |
| 39 | 3.7 | 1.7 | | >27000 |
| 40 | 0.4 | 0.3 | | |
| 41 | 45 | 14 | 4.49 | 5695 |

TABLE 1-continued

| Example | human CB$_2$ (K$_i$, nM) | rat CB$_2$ (K$_i$, nM) | rat CB$_2$ cyclase (EC$_{50}$, nM) | rCB$_1$ cyclase (EC$_{50}$, nM) |
|---|---|---|---|---|
| 43 | 62 | 3.3 | 2.09 | 6563 |
| 44 | 4.6 | 2.0 | 0.39 | 4729 |
| 45 | 8.2 | 8.6 | 0.83 | 5011 |
| 46 | 102 | 21 | 7.32 | 5418 |
| 47 | 107 | 24 | | |
| 48 | 16 | 3.0 | 0.39 | 8647 |
| 49 | 24 | 12 | 0.45 | 7761 |
| 50 | 1.3 | 0.5 | 1.21 | 1865 |
| 51 | 1.3 | 0.9 | 0.34 | 1322 |
| 53 | 3.0 | 3.6 | 0.12 | 1133 |
| 54 | 2.0 | 1.5 | 0.15 | 362 |
| 55 | 36 | 8.1 | | |
| 56 | 11 | 5.1 | 0.76 | 3051 |
| 57 | 289 | 15 | | |
| 58 | 34 | 10 | 0.18 | 2583 |
| 59 | 43 | 9.4 | 0.13 | 2270 |
| 63 | 25 | 6.6 | 2.15 | >27000 |
| 65 | 1.8 | 0.8 | | >27000 |
| 66 | 21 | 5.1 | 0.37 | 5054 |
| 67 | 115 | 13 | | >27000 |
| 69 | 3.6 | 0.9 | 0.14 | 1605 |
| 70 | 12 | 8.1 | | >27000 |
| 71 | 5.4 | 4.1 | | >27000 |
| 72 | 0.9 | 0.3 | | >27000 |
| 73 | 1.8 | 0.5 | | 2321 |
| 74 | 34 | 6.6 | | |
| 75 | 1.2 | 2.5 | | |
| 76 | 20 | 5.2 | | |
| 77 | 85 | 64 | | |
| 78 | 22 | 4.6 | | |
| 79 | 0.3 | 0.5 | | |
| 80 | 4.4 | 4.8 | | >27000 |
| 81 | 1.1 | 0.5 | | |
| 82 | 4.9 | 1.7 | | |
| 83 | 0.5 | 1.2 | | |
| 84 | 3.3 | 2.4 | | | ii) In Vivo Data Animals

Adult male Sprague-Dawley rats (250-300 g body weight, Charles River Laboratories, Portage, Mich.) are used. Animal handling and experimental protocols are approved by the Institutional Animal Care and Use Committee (IACUC) at Abbott Laboratories. For all surgical procedures, animals are maintained under isoflurane anesthesia (4-5% to induce, 1-3% to maintain), and the incision sites are sterilized using a 10% povidone-iodine solution prior to and after surgeries.

Incision Model of Postoperative Pain

A skin incision model of postoperative pain can be produced using the procedures as described in Brennan et al., 1996, Pain, 64, 493. All rats are anesthetized with isofluorane delivered via a nose cone. Right hind paw incision is performed following sterilization procedures. The plantar aspect of the left hind paw is placed through a hole in a sterile plastic drape. A 1-cm longitudinal incision is made through the skin and fascia of the plantar aspect of the hind paw, starting 0.5 cm from the proximal edge of the heel and extending towards the toes, the plantar muscle is elevated and incised longitudinally leaving the muscle origin and insertion points intact. The skin is then closed with two mattress sutures (5-0 nylon). After surgery, animals are then allowed to recover for 2 hours, at which time tactile allodynia is assessed as described below. To evaluate the anti-nociceptive effects, animals are i.p. administered vehicle or test compound 90 minutes following skin incision and tactile allodynia is assessed 30 minutes after compound administration.

Tactile allodynia is measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53,55. Rats are placed into inverted individual plastic cage (20×12.5×20 cm) on top of a suspended wire mesh grid, and acclimated to the test chambers for 20 minutes. The von Frey filaments are applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses includes an abrupt withdrawal of the hind paw from the stimulus, or flinching behavior immediately following removal of the stimulus. A 50% withdrawal threshold is determined using an up-down procedure (Dixon, W. J., 1980, Efficient analysis of experimental observations, Ann. Rev. Pharmacol. Toxicol. 20, 441).

Spinal Nerve Ligation Model of Neuropathic Pain

A model of spinal nerve ligation-induced (SNL model) neuropathic pain as originally described by Kim and Chung (Kim, S. H. and J. M. Chung, 1992, Pain 50, 355) was used to test the compounds of the present application The left L5 and L6 spinal nerves of the rat were isolated adjacent to the vertebral column and tightly ligated with a 5-0 silk suture distal to the DRG, and care was taken to avoid injury of the L4 spinal nerve. Sham rats underwent the same procedure, but without nerve ligation. All animals were allowed to recover for at least one week and not more than three weeks prior to assessment of tactile allodynia.

Tactile allodynia was measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53, 55. Rats were placed into inverted individual plastic containers (20×12.5×20 cm) on top of a suspended wire mesh grid, and acclimated to the test chambers for 20 minutes. The von Frey filaments were presented perpendicularly to the plantar surface of the selected hind paw, and then held in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol., 20, 441). Only rats with a baseline threshold score of less that 4.25 g were used in this study, and animals demonstrating motor deficit were excluded. Tactile allodynia thresholds was also assessed in several control groups, including naive, sham-operated, and saline infused animals as well as in the contralateral paws of nerve-injured rats. Compounds tested showed a statistically significant change in paw withdrawal latency versus a saline vehicle at less than about 300 micromoles/kg, for example, at less than about 100 micromoles/kg.

Capsaicin-Induced Secondary Mechanical Hypersensitivity:

Rats were allowed to acclimate to the study room for 1 hour. They were then briefly restrained, and capsaicin was administered at 10 μg in 10 μL of vehicle (10% ethanol and 2-hydroxypropyl cyclodextrin) by intraplantar injection into the center of the right hind paw. Secondary mechanical hyperalgesia was measured at the heel away from the site of injection at 180 min following capsaicin (Joshi et al 2006, Neuroscience 143, 587-596). Compounds were administered (i.p. or p.o.) 30 min before testing (150 min post-capsaicin).

Tactile allodynia was measured as described above. Compounds tested showed a statistically significant change in paw withdrawal latency versus a saline vehicle at less than about 300 micromoles/kg, for example, at less than about 100 micromoles/kg.

Sodium Iodoacetate-Induced Knee Joint Osteoarthritic Pain Model

Unilateral knee joint osteoarthritis was induced in the rats by a single intra-articular (i.a.) injection of sodium iodoacetate (3 mg in 0.05 mL sterile isotonic saline) into the right knee joint cavity under light isoflurane anesthesia using a 26G needle. The dose of the sodium iodoacetate (3 mg/i.a.injection) was selected based on results obtained from preliminary studies wherein an optimal pain behavior was observed at this dose. Pain behavioral assessment of hind limb grip force was conducted by recording the maximum compressive force exerted on the hind limb strain gauge setup, in a commercially available grip force measurement system (Columbus Instruments, Columbus, Ohio). The grip force data was converted to a maximum hindlimb cumulative compressive force (CF-max) (gram force)/kg body weight for each animal. The analgesic effects of test compounds were determined 20 days following the i.a. injection of sodium iodoacetate. The vehicle control group for each compound being tested was assigned 0% whereas the age matched nave group was assigned as being 100% (normal). The % effect for each dose group was then expressed as % return to normalcy compared to the nave group. Compounds were administered either orally (p.o.) or intraperitoneally (i.p.). The assessment of the analgesic effects of test compounds is typically made anytime between about 1 hour and about 5 hours following oral administration. The assessment of the analgesic effects of test compounds is typically made anytime between about 0.5 hour and about 2 hours following i.p. administration. Selection of the preferred time points for measuring the analgesic effects of test compounds was based upon consideration of the individual pharmacokinetic characteristics of test compounds in the rat. Time points that were known or expected to provide higher plasma concentrations of test compounds were preferred over those that were known or expected to provide lower concentrations. The assessment of the analgesic effects of test compounds can be made following a single dose or following repeated dosing of test compounds wherein the frequency of dosing is 1 to 2 times daily. The duration of such repeated daily dosing may last for any time greater than one day. A typical duration of repeated daily dosing is about 5 days to about 12 days.

Compounds tested showed a statistically significant change in hind limb grip force strength versus a saline vehicle at less than about 300 μmoles/kg in the iodoacetate-induced model of osteoarthritic pain following a single dose, for example, at less than about 50 micromoles/kg in the iodoacetate-induced model of osteoarthritic pain following a single dose. Compounds tested also showed a statistically significant change in hind limb grip force strength versus a saline vehicle at less than about 30 μmoles/kg in the iodoacetate-induced model of osteoarthritic pain following repeated daily administration for 5 to 12 days, for example, at less than about 5 micromoles/kg in the iodoacetate-induced model of osteoarthritic pain following repeated daily administration for 5 to 12 days.

Chronic Constriction Injury Model of Neuropathic Pain

A model of chronic constriction injury-induced (CCI) neuropathic pain was produced in rats by following the method of Bennett and Xie (Pain, 1988, 33:87). Following sterilization and anesthetic procedures, a 1.5 cm incision was made dorsal to the pelvis, and the biceps femoris and gluteous superficialis (right side) were separated. The right common sciatic nerve was exposed/isolated, and loosely ligated by 4 ligatures of chromic gut (5-0) with <1 mm spacing using hemostats and forceps. The wound was sutured (layer of muscle closed with 6.0 absorbable sutures, and the skin closed with wound clips or tissue glue. The animals were allowed to recover on a warming plate and were returned to their home cages (soft bedding) when able to walk on their own. Loose ligation of the sciatic nerve in rats will lead to the development of neuropathic pain within two weeks. Compounds were tested in the animals two or three weeks post-surgery.

In tactile stimulation experiments, tactile allodynia was measured using calibrated von Frey filaments (Stoelting, Wood Dale, Ill.) as previously described. Rats were placed into inverted individual plastic containers (20×12.5×20 cm) on top of a suspended wire mesh grid, and acclimated to the test chambers for 20 min. The von Frey filaments with different bending forces (starting with the lowest first and then progressively increasing) were presented perpendicularly to the plantar surface of the selected hind paw, and then hold in this position for approximately 8 sec with enough force to cause a slight bend in the filament. Positive responses included an abrupt withdrawal of the hind paw from the stimulus, or flinching behavior immediately following removal of the stimulus. Compounds tested in the CCI model of neuropathic pain showed a statistically significant change in paw withdrawal latency versus a saline vehicle at less than about 300 micromoles/kg, for example, at less than about 100 micromoles/kg.

d. METHODS OF USING THE COMPOUNDS

One embodiment provides methods for treating pain (for example, osteoarthritic pain, inflammatory pain, neuropathic pain, nociceptive pain, cancer pain, lower back pain, post-operative pain, eye pain) in a mammal (including human) in need of such treatment. The methods comprise administering to the mammal therapeutically effective amount of one or more compounds as described herein, or pharmaceutically acceptable salts or solvates thereof, alone or in combination with one or more pharmaceutically acceptable carrier(s). The method further comprises administration of compounds of the invention as a single dose. The method also comprises repeated or chronic administration of compounds of the invention over a period of days, weeks, months, or longer. In certain embodiments, the method comprises administering to the mammal a therapeutically effective amount of any of the compounds as described herein, or a pharmaceutically acceptable salt thereof, in combination with one or more nonsteroidal anti-inflammatory drug (NSAID), or other analgesics (for example, acetaminophen), or combinations thereof.

Another embodiment provides methods for treating disorders selected from the group consisting of inflammatory disorders, immune disorders, neurological disorders, cancers of the immune system, respiratory disorders, and cardiovascular disorders in a mammal in need of such treatment. The method comprises administering to the mammal therapeutically effective amount of one or more compound described herein or pharmaceutically acceptable salts or solvates thereof, alone or in combination with one or more pharmaceutically acceptable carrier(s).

Yet another embodiment relates to methods for providing neuroprotection in a mammal in need of such treatment. These methods comprise administering to the mammal therapeutically effective amounts of one or more compounds described herein or pharmaceutically acceptable salts or solvates thereof, alone or in combination with one or more pharmaceutically acceptable carrier(s).

Another embodiment provides method for increasing the therapeutic effectiveness or potency of the present compounds by repeated or chronic administration over a period of days, weeks, or months.

In addition to the data contained herein, several lines of evidence support the assertion that $CB_2$ receptors play a role in analgesia. HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabiniod ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260).

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators may be useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system.—Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands may be clinically useful for the treatment of neuroinflammation.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators may provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators may possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators may represent a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators may represent a unique approach for the treatment of liver fibrosis.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators may have utility as antitussive agents for the treatment of pulmonary inflammation, chronic cough, and a variety of airway inflammatory diseases including but not limited to asthma, chronic obstructive pulmonary disease, and pulmonary fibrosis.

There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators may be useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor may be clinically useful for the treatment of atheroscelorsis.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators may have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators may have utility for the treatment or prophylaxis of cardiovascular disease and the development of myocardial infarction.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of compounds of the invention may be required to achieve the desired therapeutic response. "Repeated or chronic administration" refers to the administration of compounds daily (i.e., every day) or intermittently (i.e., not every day) over a period of days, weeks, months, or longer. In particular, the treatment of chronic painful conditions may necessitate such repeated or chronic administration of the compounds. Compounds administered may become more effective upon repeated or chronic administration such that the therapeutically effective doses on repeated or chronic administration may be lower than the therapeutically effective dose from a single administration.

Present compounds can also be administered as a pharmaceutical composition comprising the compounds of interest in combination with one or more pharmaceutically acceptable carriers. The phrase "therapeutically effective amount" of the compound means a sufficient amount of the compound to treat disorders, at a reasonable benefit/risk ratio applicable to any medical treatment. It will be understood, however, that the total daily usage of the compounds and compositions will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Compounds described herein may be administered alone, or in combination with one or more other compounds of the invention, or in combination (i.e. co-administered) with one or more additional pharmaceutical agents. For example, one or more compounds, or pharmaceutically acceptable salts or solvates thereof, may be administered in combination with one or more analgesic (e.g. acetaminophen, opioid such as, but not limited to, morphine), or with one or more nonsteroidal anti-inflammatory drug (NSAID), or combinations thereof. Non limiting examples of NSAID include, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds of the invention and one or more additional pharmaceutical agents; as well as administration of the compounds of the invention and each additional pharmaceutical agent, in its own separate pharmaceutical dosage formulation. For example, a compound of the invention and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, compounds of the invention and one or more additional pharmaceutical agents may be administered at essentially the same time (e.g., concurrently) or at separately staggered times (e.g., sequentially).

The total daily dose of the compounds of this invention administered to a human or other animal range from about 0.01 mg/kg body weight to about 100 mg/kg body weight. More preferable doses can be in the range of from about 0.03 mg/kg body weight to about 30 mg/kg body weight. If desired, the effective daily dose can be divided into multiple doses for purposes of administration. Consequently, single dose compositions may contain such amounts or submultiples thereof to make up the daily dose. It is understood that the effective daily dose may vary with the duration of the treatment.

e. PHARMACEUTICAL COMPOSITIONS

Further provided herein are pharmaceutical compositions that comprise present compounds or pharmaceutically acceptable salts or solvates thereof, formulated together with one or more pharmaceutically acceptable carriers.

Another aspect provides pharmaceutical compositions comprising one or more compounds described herein, or pharmaceutically acceptable salts or solvates thereof, and one or more pharmaceutically acceptable carriers, alone or in combination with one or more analgesics (e.g. acetaminophen), or in combination with one or more nonsteroidal anti-inflammatory drug (NSAID), or a combination thereof.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

The present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound(s) may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated herein are compounds of the invention formed by synthetic means or formed by in vivo biotransformation of a prodrug.

The compounds can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. GENERAL SYNTHESIS

Compounds described herein when prepared by synthetic processes or by metabolic processes are encompassed within the scope of this application. Preparation of the compounds by metabolic processes includes those occurring in the human or animal body (in vivo) or processes occurring in vitro.

The compounds may be prepared by a variety of processes well known for the preparation of compounds of this class. For example, the compounds of the invention wherein the groups $A^1$, $X^1$, $R^2$, $R^3$, $R^4$, $R^x$, and z have the meanings as set forth in the summary section unless otherwise noted, can be synthesized as shown in Schemes 1-5.

Abbreviations which have been used in the descriptions of the Schemes and the Examples that follow are: dppf for 1,1'-bis(diphenylphosphino)ferrocene; DMF for N,N-dimethylformamide, DMSO for dimethyl sulfoxide, EtOAc for ethyl acetate, $Et_3N$ for triethylamine, MeOH for methanol, and THF for tetrahydrofuran.

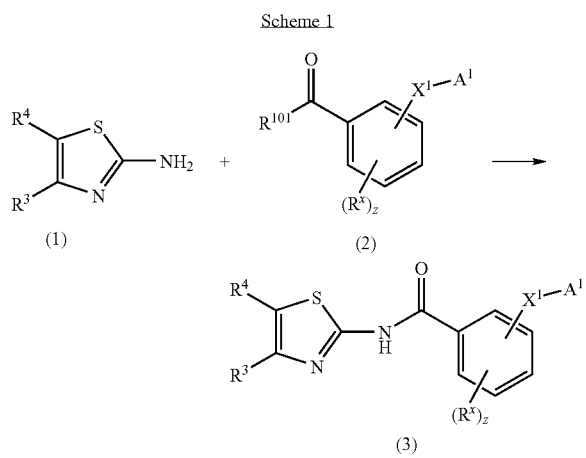

Scheme 1

As shown in Scheme 1, compounds of formula (1) containing an amine group when treated with compounds of formula (2), wherein $R^{101}$ is chloro or —OH under coupling conditions known to one skilled in the art, will provide compounds of formula (3). Typical conditions for the reaction of compounds of formula (2) wherein $R^{101}$ is chloro and compounds of formula (1) include but are not limited to stirring an equimolar mixture of the compounds in solvents such as chloroform, dichloromethane or THF in the presence of a base such as but not limited to diisopropylethylamine at 0-30° C. for 8-24 hours. Acid coupling conditions of compounds of formula (2), wherein $R^{101}$ is —OH and compounds of formula (1), include stirring an equimolar mixture of the compounds with a coupling reagent such as but not limited to bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU) along with a coupling auxiliary such as but not limited to 1-hydroxy-7-azabenzotriazole (HOAT) or 1-hydroxybenzotriazole hydrate (HOBT) in the presence or absence of a base such as but not limited to N-methyl morpholine, diisopropylethylamine in solvents such as but not limited to THF, N,N-dimethylacetamide, N,N-dimethylformamide, pyridine and chloroform. Typical reactions can be carried out between 0-65° C. or may be carried out in a microwave reactor to facilitate the coupling.

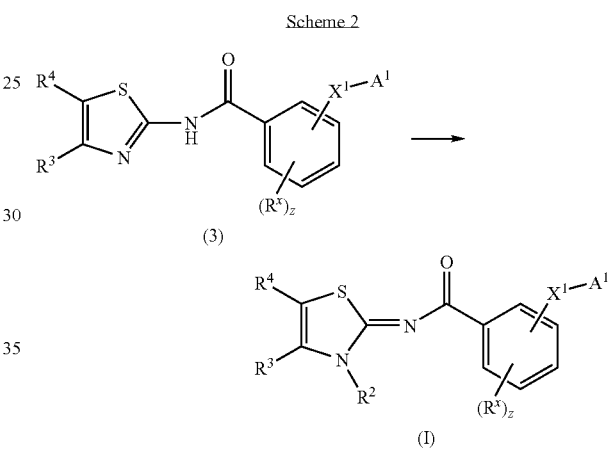

Scheme 2

As shown in Scheme 2, compounds of formula (3) may be converted into compounds of formula (I). Typical conditions include, but are not limited to, the treatment of compounds of formula (3) with sodium hydride in DMF at 0° C., followed by the addition of reagents such as $R^2$—Y, wherein Y is chloro, bromo, iodo, mesyl or triflate. Alternatively, other bases such as potassium hydroxide or potassium tert-butoxide in a mixture of THF and DMF, followed by treatment with $R^2$—Y will also provide compounds of formula (I). Compounds (3) can also be converted to compounds (I) using phase transfer conditions, for example, by refluxing of compound (3) with compounds of formula $R^2$—Y in toluene in the presence of a base like potassium carbonate and phase transfer agents like tetrabutylammonium iodide, tetrabutylammonium hydrogensulfate, tetraethylammonium iodide and the like.

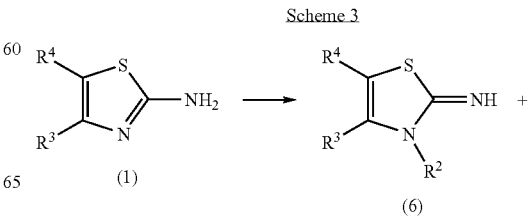

Scheme 3

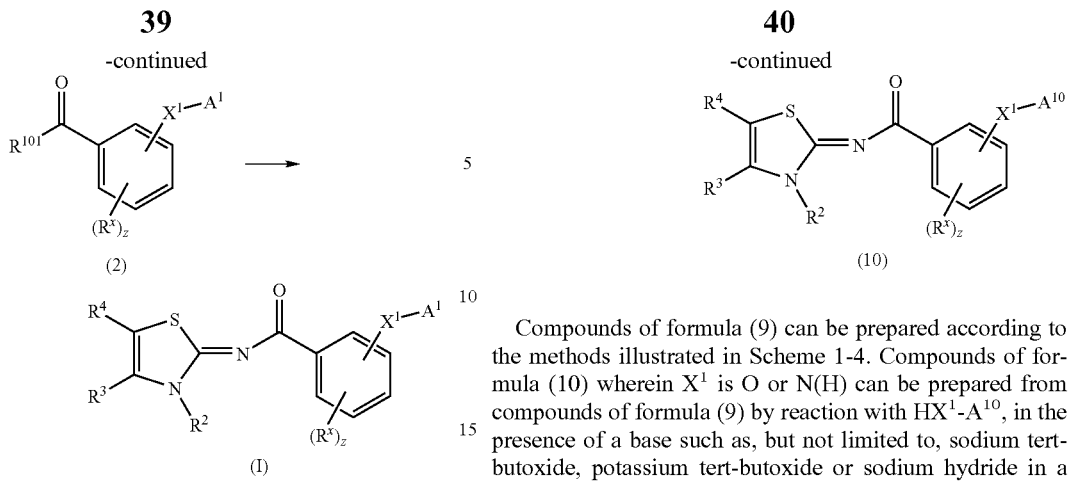

(2)

(I)

Alternatively, compounds of formula (I) may also be prepared according to the methods outlined in Scheme 3. Compounds of formula (I) when treated with sodium hydride in DMF at 0° C., followed by the addition of reagents such as $R^2$—Y, wherein $R^2$ is as defined in formula (I) and Y is chloro, bromo, iodo, tosyl, mesyl or triflate will provide compounds of formula (6). Alternatively, compounds of formula (1) may be heated neat or in the presence of a minimal amount of solvent to facilitate mixing with compounds of formula $R^2$—Y to obtain compounds of formula (6). Compounds of formula (6) may be isolated as a salt or a free base. The treatment of compounds of formula (6) with compounds of formula (2) wherein $R^{101}$ is chloro or —OH, under coupling conditions as outlined in Scheme 1 generate compounds of formula (I).

Scheme 4

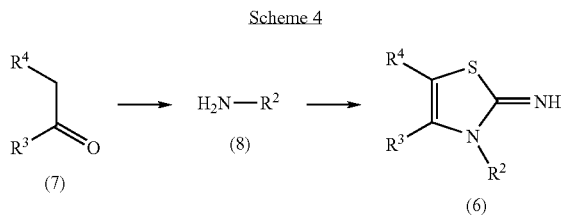

Compounds of formula (6) may be prepared according to the sequence outlined in Scheme 4. Carbonyl compounds (7) can be reacted at room temperature with amino compounds (8) in solvents such as, but not limited to, acetonitrile, tetrahydrofuran, or methylene chloride for 1-24 hours in the presence of a dehydrating agent such as, but not limited to, 4 Å molecular sieves, followed by the addition of potassium thiocyanate and iodine with heating at about 50° C. for about 4-24 hours to provide the compounds (6).

Scheme 5

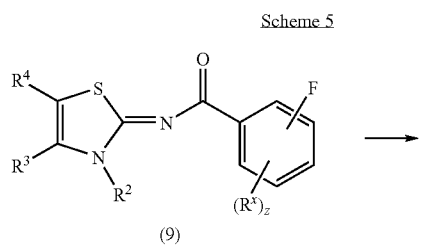

(10)

Compounds of formula (9) can be prepared according to the methods illustrated in Scheme 1-4. Compounds of formula (10) wherein $X^1$ is O or N(H) can be prepared from compounds of formula (9) by reaction with $HX^1$-$A^{10}$, in the presence of a base such as, but not limited to, sodium tert-butoxide, potassium tert-butoxide or sodium hydride in a solvent such as, but not limited to, tetrahydrofuran or N,N-dimethylformamide; wherein $A^{10}$ is $A^1$, or a derivative of $A^1$ that contains a suitable protecting group attached to a functional group present in $A^1$. For groups $A^{10}$ that contain a protecting group, such groups may be removed using chemical techniques that are well-known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Following removal of any protecting group, molecules can be further transformed to compounds of the invention using standard chemical techniques well-known to those skilled in the art such as alkylation, acylation, reductive amination, sulfonylation, oxidation, reduction and the like.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

g. EXAMPLES

Example 1

2-[(2R)-azetidin-2-ylmethoxy]-N-[(2Z)-5-tert-butyl-3-[(2R)-tetrahydrofuran-2-ylmethyl]-1,3-thiazol-2(3H)-ylidene]-5-(trifluoromethyl)benzamide

Example 1A

N-[(2Z)-5-tert-butyl-3-[(2R)-tetrahydrofuran-2-ylmethyl]-1,3-thiazol-2(3H)-ylidene]-2-fluoro-5-(trifluoromethyl)benzamide To Example 22A (3.0 g, 8.15 mmol) and triethylamine (3.41 mL, 24.44 mmol) in $CH_2Cl_2$ (30 mL) was added 2-fluoro-5-(trifluoromethyl)benzoyl chloride (1.481 mL, 9.78 mmol) dropwise. The mixture was stirred at room temperature for 2h. Water and $CH_2Cl_2$ (100 mL/100 mL) were added and the organic layer was washed with brine and concentrated. Purification by flash chromatography (silica gel, EtOAc/hexane in 10-50% gradient) afforded 2.9 g (83%) of the title compound. $^1$H NMR (300 MHz, DMSO-$d_6$) δ ppm 1.33 (s, 9 H), 1.60-2.01 (m, 4 H), 3.60-3.71 (m, 1 H), 3.74-3.87 (m, 1 H), 4.18-4.40 (m, 3 H), 7.35 (s, 1 H), 7.47-7.59 (m, 1 H), 7.88-7.97 (m, 1 H), 8.31 (dd, J=6.74, 2.78 Hz, 1 H); MS (ESI) m/z 431 (M+H)$^+$.

Example 1B tert-butyl (2R)-2-{[2-{[(2Z)-5-tert-butyl-3-[(2R)-tetrahydrofuran-2-ylmethyl]-1,3-thiazol-2(3H)-ylidene]carbamoyl}-4-(trifluoromethyl)phenoxy]methyl}azetidine-1-carboxylate Example 1A (430 mg, 1.0 mmol) in THF (10 mL), sodium tert-butoxide (192 mg, 2.0 mmol) and (R)-tert-butyl 2-(hydroxymethyl)azetidine-1-carboxylate (374 mg, 2.0 mmol) were reacted for 1 hour at room temperature. The reaction was quenched with saturated aqueous $NH_4Cl$ and extracted by EtOAc (3×10 mL). The combined organic layer was washed with brine and concentrated. Purification by flash chromatography (silica gel, EtOAc/hexane in 5-40% gradient) afforded 484 mg (81%) of the title compound. $^1$H NMR (300 MHz, CDCl$_3$) δ ppm 1.33-1.37 (m, 9 H), 1.40 (s, 9 H), 1.59-2.40 (m, 6 H), 3.68-3.92 (m, 5 H), 4.08-4.31 (m, 2 H), 4.39-4.56 (m, 3 H), 6.86 (s, 1 H), 7.10 (d, J=8.33 Hz, 1 H), 7.58 (dd, J=8.72, 2.78 Hz, 1 H), 8.15 (d, J=2.38 Hz, 1 H); MS (ESI) m/z 598 (M+H)$^+$.

Example 1C

2-[(2R)-azetidin-2-ylmethoxy]-N-[(2Z)-5-tert-butyl-3-[(2R)-tetrahydrofuran-2-ylmethyl]-1,3-thiazol-2(3H)-ylidene]-5-(trifluoromethyl)benzamide The mixture of Example 1B (472 mg, 0.79 mmol) and 2,2,2-trifluoroacetic acid (608 μL, 7.9 mmol) in $CH_2Cl_2$ (10 mL) was stirred at room temperature overnight. Saturated aqueous $Na_2CO_3$ (20 mL) and $CH_2Cl_2$ (20 mL) were added. The organic layer was washed with brine and concentrated. Purification by gradient flash chromatography (silica gel, 5-30% solvent A in EtOAc, solvent A: MeOH (10):Et$_3$N (1)) afforded 330.5 mg (84%) of the title compound. $^1$H NMR (300 MHz, DMSO-$d_6$) δ ppm 1.32 (s, 9 H), 1.56-2.00 (m, 4 H), 2.03-2.34 (m, 2 H), 3.23-3.35 (m, 2 H), 3.59-3.71 (m, 2 H), 3.74-3.83 (m, 2 H), 4.03-4.34 (m, 5 H), 7.27 (s, 1 H), 7.32 (d, J=8.81 Hz, 1 H), 7.75 (dd, J=8.98, 2.20 Hz, 1 H), 7.98 (d, J=2.37 Hz, 1 H); MS (ESI) m/z 498 (M+H)$^+$.

Example 2

2-[(2S)-azetidin-2-ylmethoxy]-N-[(2Z)-5-tert-butyl-3-[(2R)-tetrahydrofuran-2-ylmethyl]-1,3-thiazol-2(3H)-ylidene]-5-(trifluoromethyl)benzamide

Example 2A tert-butyl (2S)-2-{[2-{[(2Z)-5-tert-butyl-3-[(2R)-tetrahydrofuran-2-ylmethyl]-1,3-thiazol-2(3H)-ylidene]carbamoyl}-4-(trifluoromethyl)phenoxy]methyl}azetidine-1-carboxylate The mixture of (S)-tert-butyl 2-(hydroxymethyl)azetidine-1-carboxylate (374 mg, 2.0 mmol) and sodium tert-butoxide (192 mg, 2.0 mmol) in THF (10 mL) was stirred at ambient temperature for 10 minutes, then Example 1A (430 mg, 1.0 mmol) was added. The mixture was stirred for another 1 hour and monitored by LC/MS. The reaction was quenched with saturated aqueous $NH_4Cl$ and extracted by EtOAc (3×10 mL). The combined organic layer was washed with brine and concentrated. Purification by flash chromatography (silica gel, 5-30% solvent A in EtOAc, solvent A: MeOH (10):Et$_3$N (1)) afforded 538 mg (90%) of the title compound. $^1$H NMR (300 MHz, DMSO-$d_6$) δ ppm 1.29-1.32 (m, 9 H), 1.37 (s, 9 H), 1.51-2.31 (m, 6 H), 3.42-3.85 (m, 5 H), 4.06-4.30 (m, 3 H), 4.42-4.45 (m, 2 H), 4.70-4.74 (m , 1 H), 7.20-7.37 (m, 2 H), 7.74 (dd, J=8.92, 2.18 Hz, 1 H), 7.99 (d, J=2.38 Hz, 1 H); MS (ESI) m/z 598 (M+H)$^+$.

Example 2B

2-[(2S)-azetidin-2-ylmethoxy]-N-[(2Z)-5-tert-butyl-3-[(2R)-tetrahydrofuran-2-ylmethyl]-1,3-thiazol-2(3H)-ylidene]-5-(trifluoromethyl)benzamide The mixture of Example 2A (478 mg, 0.8 mmol) and 2,2,2-trifluoroacetic acid (616 μL, 8.0 mmol) in $CH_2Cl_2$ (10 mL) was stirred at ambient temperature overnight. Saturated aqueous $Na_2CO_3$ (20 mL) was added followed by $CH_2Cl_2$ (30 mL). The organic layer was washed with brine and concentrated. Purification by gradient flash chromatography (silica gel, 5-30% (Et$_3$N:MeOH, 1:10)/EtOAc) afforded 340 mg (85%) of the title compound. $^1$H NMR (300 MHz, DMSO-d$_6$) δ ppm 1.32 (s, 9 H), 1.55-1.98 (m, 4 H), 2.04-2.34 (m, 2 H), 3.25-3.51 (m, 1 H), 3.59-3.87 (m, 4 H), 4.01-4.39 (m, 6 H), 7.26 (s, 1 H), 7.32 (d, J=8.73 Hz, 1 H), 7.74 (dd, J=8.73, 2.78 Hz, 1 H), 7.98 (d, J=2.38 Hz, 1 H); MS (ESI) m/z 498 (M+H)$^+$.

Example 3

N-[(2Z)-5-tert-butyl-3-[(2R)-tetrahydrofuran-2-ylmethyl]-1,3-thiazol-2(3H)-ylidene]-2-{[(2S)-1-methylazetidin-2-yl]methoxy}-5-(trifluoromethyl)benzamide To Example 2B (200 mg, 0.4 mmol) and sodium acetate (33 mg, 0.4 mmol) in MeOH (6 mL) was added formaldehyde (48.3 mg, 1.6 mmol) and sodium triacetoxyborohydride (341 mg, 1.6 mmol). The mixture was stirred at room temperature for 2 hours. The reaction was quenched with saturated NaHCO$_3$ and extracted by CH$_2$Cl$_2$ (10 mL×2). The combined organic layer was washed with brine and concentrated. Purification by flash chromatography (silica gel, EtOAc/MeOH/Et$_3$N (90:10:0.5) afforded 187 mg (91%) of the title compound. $^1$H NMR (300 MHz, DMSO-d$_6$) δ ppm 1.32 (s, 9 H), 1.56-2.02 (m, 6 H), 2.21 (s, 3 H), 2.65-2.80 (m, 1 H), 3.11-3.25 (m, 2 H), 3.58-3.85 (m, 2 H), 3.97-4.37 (m, 5 H), 7.16-7.33 (m, 2 H), 7.73 (dd, J=8.73, 2.38 Hz, 1 H), 7.93 (d, J=2.38 Hz, 1 H); MS (ESI) m/z 512 (M+H)$^+$.

Example 4

N-[(2Z)-5-tert-butyl-3-[(2R)-tetrahydrofuran-2-ylmethyl]-1,3-thiazol-2(3H)-ylidene]-2-[2 S)-piperidin-2-ylmethoxy]-5-(trifluoromethyl)benzamide Example 4A tert-butyl (2S)-2-{[2-{[(2Z)-5-tert-butyl-3-[(2R)-tetrahydrofuran-2-ylmethyl]-1,3-thiazol-2(3H)-ylidene]carbamoyl}-4-(trifluoromethyl)phenoxy]methyl}piperidine-1-carboxylate The title compound was made from Example 1A and (S)-tert-butyl 2-(hydroxymethyl)piperidine-1-carboxylate in 83% yield using the method of Example 1B. $^1$H NMR (300 MHz, CDCl$_3$) δ ppm 1.36 (s, 9 H), 1.43 (m, 9H), 1.52-1.70 (m, 6 H) 1.73-1.94 (m, 2 H), 1.96-2.13 (m, 2 H), 2.80-2.95 (m, 1 H), 3.71-3.91 (m, 2 H), 3.96-4.30 (m, 5H), 4.34-4.46 (m, 1 H), 4.57 (dd, J=8.48, 4.75 Hz, 1 H), 6.85-6.90 (m, 1 H), 7.26 (s, 1 H), 7.59 (dd, J=8.99, 2.20 Hz, 1 H), 8.12 (d, J=2.03 Hz, 1 H); MS (ESI) m/z 626 (M+H)$^+$.

Example 4B

N-[(2Z)-5-tert-butyl-3-[(2R)-tetrahydrofuran-2-ylmethyl]-1,3-thiazol-2(3H)-ylidene]-2-[(25)-piperidin-2-ylmethoxy]-5-(trifluoromethyl)benzamide The title compound was made from Example 4A in 91% yield using the method of Example 1C. $^1$H NMR (300 MHz, DMSO-d$_6$) δ ppm 1.01-1.39 (m, 3 H), 1.33 (s, 9 H), 1.45-2.01 (m, 8 H), 2.56 (d, J=2.78 Hz, 1 H), 2.80-2.90 (m, 1 H), 2.96 (d, J=11.50 Hz, 1 H), 3.61-3.70 (m, 1 H), 3.74-3.92 (m, 2 H), 4.04-4.13 (m, 1 H), 4.17-4.33 (m, 3 H), 7.25-7.33 (m, 2 H), 7.74 (dd, J=8.72, 2.38 Hz, 1 H), 8.02 (d, J=2.38 Hz, 1 H); MS (ESI) m/z 526 (M+H)$^+$.

Example 5

N-[(2Z)-5-tert-butyl-3-[(2R)-tetrahydrofuran-2-ylmethyl]-1,3-thiazol-2(3H)-ylidene]-2-{[2S)-1-methylpiperidin-2-yl]methoxy}-5-(trifluoromethyl)benzamide The title compound was made from Example 4B in 90% yield using the method described in Example 3. $^1$H NMR (300 MHz, DMSO-d$_6$) δ ppm 1.10-1.30 (m, 2 H), 1.32 (s, 9 H), 1.36-2.08 (m, 9 H), 2.17-2.30 (m, 4 H), 2.67-2.78 (m, 1 H), 3.59-3.72 (m, 1 H), 3.74-3.83 (m, 1 H), 3.93 (dd, J=9.91, 5.95 Hz, 1 H), 4.16-4.33 (m, 4 H), 7.23-7.33 (m, 2H), 7.73 (dd, J=8.92, 2.58 Hz, 1 H), 7.94 (d, J=2.38 Hz, 1 H); MS (ESI) m/z 540(M+H)$^+$.

Example 6

N-[(2Z)-5-tert-butyl-3-[(2R)-tetrahydro furan-2-ylmethyl]-1,3-thiazol-2(3H)-ylidene]-2-[(2R)-piperidin-2-ylmethoxy]-5-(trifluoromethyl)benzamide Example 6A tert-butyl (2R)-2-{[2-{[(2Z)-5-tert-butyl 3-[(2R)-tetrahydrofuran-2-ylmethyl]-1,3-thiazol-2(3H)-ylidene]carbamoyl}-4-(trifluoromethyl)phenoxy]methyl}piperidine-1-carboxylate The title compound was made from Example 1A and (R)-tert-butyl 2-(hydroxymethyl)piperidine-1-carboxylate in 90% yield using the method of Example 1B. $^1$H NMR (300 MHz, CDCl$_3$) δ ppm 1.36 (s, 9 H), 1.40-1.45 (m, 9 H), 1.50-1.66 (m, 6 H) 1.73-1.90 (m, 2 H), 1.92-2.10 (m, 2 H), 2.80-2.95 (m, 1 H), 3.71-3.91 (m, 2 H), 3.96-4.30 (m, 5 H), 4.34-4.46 (m, 1 H), 4.57 (dd, J=8.48, 4.75 Hz, 1 H), 6.85-6.90 (m, 1 H), 7.23 (s, 1 H), 7.59 (dd, J=8.99, 2.20 Hz, 1 H), 8.12 (d, J=2.03 Hz, 1 H); MS (ESI) m/z 626 (M+H)$^+$.

Example 6B

N-[(2Z)-5-tert-butyl-3-[(2R)-tetrahydrofuran-2-ylmethyl]-1,3-thiazol-2(3H)-ylidene]-2-[(2R)-piperidin-2-ylmethoxy]-5-(trifluoromethyl)benzamide The title compound was made from Example 6A in 93% yield using the method of Example 1C. $^1$H NMR (300 MHz, DMSO-d$_6$) δ ppm 0.99-1.30 (m, 3 H), 1.32 (s, 9 H), 1.44-2.00 (m, 7 H), 2.33 (s, 1 H), 2.52-2.61 (m, 1H), 2.78-2.90 (m, 1 H), 2.95 (d, J=11.90 Hz, 1 H), 3.60-3.70 (m, 1 H), 3.73-3.91 (m, 2 H), 4.07 (dd, J=9.52, 4.76 Hz, 1 H), 4.18-4.34 (m, 3 H), 7.25-7.33 (m, 2 H), 7.74 (dd, J=8.92, 2.58 Hz, 1 H), 8.01 (d, J=2.38 Hz, 1 H); MS (ESI) m/z 526 (M+H)$^+$.

Example 7

N-[(2Z)-5-tert-butyl-3-[(2R)-tetrahydrofuran-2-ylmethyl]-1,3-thiazol-2(3H)-ylidene]-2-{[(2R)-1-methylpiperidin-2-yl]methoxy}-5-(trifluoromethyl)benzamide The title compound was made from Example 6B in 90% yield using the method of Example 3. $^1$H NMR (300 MHz, DMSO-d$_6$) δ ppm 1.15-1.32 (m, 2 H), 1.32 (s, 9 H), 1.37-2.07 (m, 9 H), 2.17-2.32 (m, 4 H), 2.73 (dd, J=7.34, 3.77 Hz, 1 H), 3.66 (t, J=7.34 Hz, 1 H), 3.71-3.85 (m, 1 H), 3.93 (dd, J=10.11, 5.75 Hz, 1 H), 4.13-4.34 (m, 4 H), 7.20-7.38 (m, 2H), 7.73 (dd, J=8.92, 2.58 Hz, 1 H), 7.94 (d, J=2.38 Hz, 1 H); MS (ESI) m/z 540 (M+H)$^+$.

Example 8

N-[(2Z)-5-tert-butyl-3-[(2R)-tetrahydrofuran-2-ylmethyl]-1,3-thiazol-2(3H)-ylidene]-2-{[(2R)-1-methylazetidin-2-yl]methoxy}-5-(trifluoromethyl)benzamide The title compound was made from Example 1C in 88% yield using the method of Example 3. $^1$H NMR (300 MHz, DMSO-d$_6$) δ ppm 1.32 (s, 9 H) 1.53-2.05 (m, 7 H), 2.21 (s, 3 H), 2.65-2.78 (m, 1 H), 3.16-3.30 (m, 2 H), 3.59-3.72 (m, 1 H), 3.72-3.85 (m, 1 H), 3.98-4.35 (m, 5 H), 7.20-7.32 (m, 2 H), 7.73 (dd, J=8.73, 2.38 Hz, 1 H); MS (ESI) m/z 512 (M+H)$^+$.

Example 9

2-(azetidin-3-ylmethoxy)-N-[(2Z)-5-tert-butyl-3-[(2R)-tetrahydro furan-2-ylmethyl]-1,3-thiazol-2(3H)-ylidene]-5-(trifluoromethyl)benzamide Example 9A tert-butyl 3-{[2-{[(2Z)-5-tert-butyl-3-[(2R)-tetrahydrofuran-2-ylmethyl]-1,3-thiazol-2(3H)-ylidene]carbamoyl}-4-(trifluoromethyl)phenoxy]methyl}azetidine-1-carboxylate The title compound was made from Example 1A and tert-butyl 3-(hydroxymethyl)azetidine-1-carboxylate in 92% yield using the method of Example 1B. $^1$H NMR (300 MHz, CDCl$_3$) δ ppm 1.36 (s, 9 H), 1.43 (s, 9 H), 1.62-1.73 (m, 1 H), 1.76-1.95 (m, 2 H), 2.01-2.11 (m, 1 H), 2.98-3.13 (m, 1 H), 3.74-3.88 (m, 4 H), 4.03-4.32 (m, 6H), 4.41 (dd, J=13.48, 2.78 Hz, 1 H), 6.88 (s, 1 H), 7.03 (d, J=8.33 Hz, 1 H), 7.60 (dd, J=8.72, 2.38 Hz, 1 H), 8.17 (d, J=2.38 Hz, 1 H); MS (ESI) m/z 598 (M+H)$^+$.

Example 9B 2-(azetidin-3-ylmethoxy)-N-[(2Z)-5-tert-butyl-3-[(2R)-tetrahydrofuran-2-ylmethyl]-1,3-thiazol-2(3H)-ylidene]-5-(trifluoromethyl)benzamide The title compound was made from Example 9A in 94% yield using the method of Example 1C. $^1$H NMR (300 MHz, DMSO-d$_6$) δ ppm 1.32 (s, 9 H), 1.58-1.72 (m, J=12.89, 5.76 Hz, 1 H), 1.75-2.00 (m, 4 H), 2.96-3.10 (m, J=5.76 Hz, 1 H), 3.50 (dd, J=8.31, 5.59 Hz, 2 H), 3.59-3.71 (m, 2 H) 3.71-3.84 (m, 2 H), 4.18-4.35 (m, 5 H), 7.29 (s, 1 H) 7.32 (d, J=8.82 Hz, 1 H), 7.78 (dd, J=8.65, 2.20 Hz, 1 H), 8.11 (d, J=2.03 Hz, 1 H); MS (ESI) m/z 498 (M+H)$^+$.

Example 10

N-[(2Z)-5-tert-butyl-3-[(2R)-tetrahydrofuran-2-ylmethyl]-1,3-thiazol-2(3H)-ylidene]-2-[(3R)-piperidin-3-ylmethoxy]-5-(trifluoromethyl)benzamide Example 10A tert-butyl (3R)-3-{[2-{[(2Z)-5-tert-butyl-3-[(2R)-tetrahydrofuran-2-ylmethyl]-1,3-thiazol-2(3H)-ylidene]carbamoyl}-4-(trifluoromethyl)phenoxy]methyl}piperidine-1-carboxylate The title compound was made from Example 1A and (R)-tert-butyl 3-(hydroxymethyl)piperidine-1-carboxylate (Ennova MedChem Group) in 75% yield using the method of Example 1B. $^1$H NMR (300 MHz, DMSO-d$_6$) δ ppm 0.89-1.30 (m, 4 H), 1.21-1.44 (m, 18 H), 1.55-1.96 (m, 6 H), 2.59-2.84 (m, 2 H), 3.55-4.09 (m, 6 H), 4.15-4.33 (m, 2 H), 7.21-7.32 (m, 2 H), 7.74 (dd, J=8.72, 2.38 Hz, 1 H), 7.98 (s, 1 H); MS (ESI) m/z 626 (M+H)$^+$.

Example 10B

N-[(2Z)-5-tert-butyl-3-[(2R)-tetrahydro furan-2-ylmethyl]-1,3-thiazol-2(3H)-ylidene]-2-[(3R)-piperidin-3-ylmethoxy]-5-(trifluoromethyl)benzamide The title compound was made from Example 10A in 95% yield using the method of Example 1C. $^1$H NMR (300 MHz, DMSO-d$_6$) δ ppm 1.11-1.53 (m, 2 H), 1.33 (s, 9 H), 1.56-1.71 (m, 2 H), 1.74-2.11 (m, 6 H), 2.43-2.66 (m, 2 H), 2.87-2.99 (m, 1 H), 3.17 (m, 1H), 3.60-3.69 (m, 1 H), 3.73-3.83 (m, 1 H), 3.89-4.10 (m, 2 H), 4.11-4.36 (m, 3 H), 7.19-7.33 (m, 2 H), 7.75 (dd, J=8.72, 2.38 Hz, 1 H), 8.03 (d, J=2.38 Hz, 1 H); MS (ESI) m/z 526 (M+H)$^+$.

Example 11

N-[(2Z)-5-tert-butyl-3-[(2R)-tetrahydrofuran-2-ylmethyl]-1,3-thiazol-2(3H)-ylidene]-2-{[(3R)-1-methylpiperidin-3-yl]methoxy}-5-(trifluoromethyl)benzamide The title compound was made from Example 10B in 91% yield using the method of Example 3. $^1$H NMR (300 MHz, DMSO-d$_6$) δ ppm 0.84-1.20 (m, 2 H), 1.32 (s, 9 H) 1.38-2.04 (m, 10 H), 2.10 (s, 3 H), 2.70-2.84 (m, 1 H), 3.56-3.70 (m, 1 H), 3.72-3.84 (m, 1 H), 3.86-4.08 (m, 2 H), 4.13-4.37 (m, 3 H), 7.20-7.34 (m, 2 H), 7.72 (dd, J=8.65, 1.86 Hz, 1H), 7.94 (d, J=2.03 Hz, 1 H); MS (ESI) m/z 540 (M+H)$^+$.

Example 12

N-[(2Z)-5-tert-butyl-3-[(2R)-tetrahydrofuran-2-ylmethyl]-1,3-thiazol-2(3H)-ylidene]-2-[(1-methylazetidin-3-yl)methoxy]-5-(trifluoromethyl)benzamide The title compound was made from Example 9B in 91% yield using the method of Example 3. $^1$H NMR (300 MHz, DMSO-d$_6$) δ ppm 1.32 (s, 9 H), 1.54-1.72 (m, 1H), 1.73-1.96 (m, 3 H), 2.17 (s, 3 H), 2.69-2.83 (m, 1 H), 3.01 (t, J=6.35 Hz, 2 H), 3.26 (t, J=7.14 Hz, 2 H), 3.59-3.70 (m, 1 H), 3.74-3.85 (m, 1 H), 4.15-4.34 (m, 5 H) 7.22-7.33 (m, 2 H), 7.74 (dd, J=8.72, 1.98 Hz, 1 H), 7.95 (d, J=2.38 Hz, 1 H); MS (ESI) m/z 512 (M+H)$^+$.

Example 13

N-[(2Z)-5-tert-butyl-3-[(2R)-tetrahydrofuran-2-ylmethyl]-1,3-thiazol-2(3H)-ylidene]-2-[(3S)-piperidin-3-ylmethoxy]-5-(trifluoromethyl)benzamide

Example 13A tert-butyl (3S)-3-{[2-{[(2Z)-5-tert-butyl-3-[(2R)-tetrahydrofuran-2-ylmethyl]-1,3-thiazol-2(3H)-ylidene]carbamoyl}-4-(trifluoromethyl)phenoxy]methyl}piperidine-1-carboxylate The title compound was made from Example 1A and (S)-tert-butyl 3-(hydroxymethyl)piperidine-1-carboxylate in 70% yield using the method of Example 1B. $^1$H NMR (300 MHz, CDCl$_3$) δ ppm 1.36 (s, 9 H), 1.38-1.48 (m, 9 H), 1.51-2.17 (m, 9 H), 2.71-2.91 (m, 2 H), 3.72-4.32 (m, 8 H), 4.42 (dd, J=13.56, 2.71 Hz, 1 H), 6.87 (s, 1 H), 6.99 (d, J=8.82 Hz, 1 H), 7.58 (dd, J=8.65, 1.86 Hz, 1 H), 8.16 (s, 1 H); MS (ESI) m/z 626 (M+H)$^+$.

Example 13B

N-[(2Z)-5-tert-butyl-3-[(2R)-tetrahydrofuran-2-ylmethyl]-1,3-thiazol-2(3H)-ylidene]-2-[(3S)-piperidin-3-ylmethoxy]-5-(trifluoromethyl)benzamide The title compound was made from Example 13A in 93% yield using the method of Example 1C. $^1$H NMR (300 MHz, DMSO-d$_6$) δ ppm 1.05-1.46 (m, 2 H), 1.32 (s, 9 H), 1.52-1.70 (m, 2 H), 1.75-1.97 (m, 7 H), 2.26-2.44 (m, 1 H), 2.78-2.94 (m, 1 H), 3.09 (dd, J=11.70, 2.97 Hz, 1 H), 3.59-3.70 (m, 1 H), 3.72-3.84 (m, 1 H), 3.87-4.06 (m, 2 H), 4.16-4.33 (m, 3 H), 7.21-7.30 (m, 2 H), 7.73 (dd, J=8.73, 2.38 Hz, 1 H), 7.98 (d, J=2.38 Hz, 1 H); MS (ESI) m/z 526 (M+H)$^+$.

Example 14

N-[(2Z)-5-tert-butyl-3-[(2R)-tetrahydrofuran-2-ylmethyl]-1,3-thiazol-2(3H)-ylidene]-2-{[(3S)-1-methylpiperidin-3-yl]methoxy}-5-(trifluoromethyl)benzamide The title compound was made from Example 13B in 75% yield using the method of Example 3. $^1$H NMR (300 MHz, DMSO-d$_6$) δ ppm 0.85-1.14 (m, 1 H), 1.32 (s, 9 H), 1.39-2.04 (m, 10 H), 2.10 (s, 3 H), 2.55-2.66 (m, 1 H), 2.68-2.86 (m, 1 H), 3.57-3.70 (m, 1 H), 3.72-3.84 (m, 1 H), 3.86-4.06 (m, 2 H), 4.11-4.33 (m, 3 H), 7.20-7.32 (m, 2 H), 7.73 (dd, J=8.72, 2.38 Hz, 1 H), 7.94 (d, J=1.98 Hz, 1 H); MS (ESI) m/z 540 (M+H)$^+$.

Example 15

N-[(2Z)-5-tert-butyl-3-[(2R)-tetrahydrofuran-2-ylmethyl]-1,3-thiazol-2(3H)-ylidene]-2-[(1-methylpiperidin-4-yl)methoxy]-5-(trifluoromethyl)benzamide The title compound was made from Example 16B in 89% yield using the method of Example 3. $^1$H NMR (300 MHz, DMSO-d$_6$) δ ppm 1.18-1.41 (m, 11 H), 1.54-2.01 (m, 9H), 2.13 (s, 3 H), 2.75 (d, J=10.85 Hz, 2 H), 3.66 (t, J=7.46 Hz, 1 H), 3.71-3.86 (m, 1 H), 3.95 (d, J=6.10 Hz, 2 H), 4.13-4.35 (m, 3 H), 7.17-7.38 (m, 2 H), 7.72 (dd, J=8.65, 1.86 Hz, 1 H), 7.97 (d, J=2.71 Hz, 1 H); MS (ESI) m/z 540 (M+H)$^+$.

Example 16

N-[(2Z)-5-tert-butyl-3-[(2R)-tetrahydrofuran-2-ylmethyl]-1,3-thiazol-2(3H)-ylidene]-2-(piperidin-4-ylmethoxy)-5-(trifluoromethyl)benzamide

Example 16A tert-butyl 4-{[2-{[(2Z)-5-tert-butyl-3-[(2R)-tetrahydrofuran-2-ylmethyl]-1,3-thiazol-2(3H)-ylidene]carbamoyl}-4-(trifluoromethyl)phenoxy]methyl}piperidine-1-carboxylate The title compound was made from Example 1A and tert-butyl 4-(hydroxymethyl)piperidine-1-carboxylate in 71% yield using the method of Example 1B. $^1$H NMR (300 MHz, CDCl$_3$) δ ppm 1.15-1.32 (m, 2 H), 1.36 (s, 9 H), 1.45 (s, 9 H), 1.61-1.96 (m, 5 H), 1.99-2.14 (m, 2 H), 2.74 (t, J=12.49 Hz, 2 H), 3.73-3.97 (m, 4 H), 4.06-4.32 (m, 4 H), 4.42 (dd, J=13.48, 2.78 Hz, 1 H), 6.86 (s, 1 H) 6.99 (d, J=8.72 Hz, 1 H), 7.58 (dd, J=8.73, 2.38 Hz, 1 H), 8.17 (d, J=2.38 Hz, 1 H); MS (ESI) m/z 626 (M+H)$^+$.

Example 16B

N-[(2Z)-5-tert-butyl-3-[(2R)-tetrahydrofuran-2-ylmethyl]-1,3-thiazol-2(3H)-ylidene]-2-(piperidin-4-ylmethoxy)-5-(trifluoromethyl)benzamide The title compound was made from Example 16A in 95% yield using the method of Example 1C. $^1$H NMR (300 MHz, DMSO-d$_6$) δ ppm 1.08-1.26 (m, 2 H), 1.32 (s, 9 H), 1.56-1.99 (m, 10 H), 2.98 (d, J=11.87 Hz, 2 H), 3.58-3.83 (m, 1 H), 3.93 (d, J=6.78 Hz, 2 H), 4.17-4.34 (m, 3 H), 4.36-4.51 (m, 1 H), 7.21-7.31 (m, 2 H), 7.72 (dd, J=8.82, 2.37 Hz, 1H), 7.97 (d, J=2.37 Hz, 1 H); MS (ESI) m/z 526 (M+H)$^+$.

Example 17

N-[(2Z)-5-tert-butyl-3-[(2R)-tetrahydrofuran-2-ylmethyl]-1,3-thiazol-2(3H)-ylidene]-2-[(1-methyl-1H-imidazol-2-yl)methoxy]-5-(trifluoromethyl)benzamide A solution of (1-methyl-1H-imidazol-2-yl)methanol (109 mg, 0.94 mmol) in THF (5 mL) was treated with a 1 M KOtBu/THF (0.95 mL, 0.944 mmol) and stirred for 15 min. A solution of Example 1A (190 mg, 0.47 mmol) was added to the reaction mixture and stirred for 6 hours. The reaction mixture was quenched with saturated NH$_4$Cl solution, concentrated in vacuo and partitioned between EtOAc and brine, dried (MgSO$_4$), filtered, and concentrated. The residue was purified by using an Analogix® Intelliflash280™ (SiO$_2$, 0-60% ethyl acetate in hexanes) to afford the title compound (120 mg, 33% yield). $^1$H NMR (300 MHz, DMSO-d$_6$) δ ppm 1.31 (s, 9 H), 1.50-1.66 (m, 1 H), 1.68-1.96 (m, 3 H), 3.55-3.84 (m, 5 H), 4.05-4.32 (m, 3 H), 5.29 (s, 2 H), 6.86 (s, 1 H), 7.20 (s, 1 H), 7.26 (s, 1 H), 7.52 (d, J=8.8 Hz, 1 H), 7.79 (dd, J=9.0, 2.2 Hz, 1 H), 8.01 (d, J=2.4 Hz, 1 H). MS (DCI/NH$_3$) m/z 523 (M+H)$^+$. Anal. calcd for C$_{25}$H$_{29}$F$_3$N$_4$O$_3$S: C, 57.46; H, 5.59; N, 10.72. Found: C, 56.96; H, 5.57; N, 10.46.

Example 18

N-[(2Z)-5-tert-butyl-3-[(2R)-tetrahydrofuran-2-ylmethyl]-1,3-thiazol-2(3H)-ylidene]-2-(pyridin-2-ylmethoxy)-5-(trifluoromethyl)benzamide The title compound was prepared from Example 1A and pyridin-2-ylmethanol according to the procedure of Example 17. $^1$H NMR (300 MHz, DMSO-d$_6$) δ ppm 1.33 (s, 9H), 1.52-1.66 (m, 1 H), 1.67-1.95 (m, 3 H), 3.55-3.67 (m, 1 H), 3.69-3.85 (m, 1 H), 4.13-4.21 (m, 2 H), 4.21-4.31 (m, 1 H), 5.35 (s, 2 H), 7.23-7.29 (m, 1 H), 7.29-7.41 (m, 2 H), 7.64 (d, J=7.8 Hz, 1 H), 7.74 (dd, J=9.0, 2.2 Hz, 1 H), 7.80-7.90 (m, 1 H), 8.04 (d, J=2.4 Hz, 1 H), 8.58 (d, J=4.1 Hz, 1 H). MS (DCI/NH$_3$) m/z 520 (M+H)$^+$. Anal. calcd for C$_{26}$H$_{28}$F$_3$N$_3$O$_3$S: C, 60.10; H, 5.43; N, 8.09. Found: C, 60.10; H, 5.44; N, 7.87.

Example 19

N-[(2Z)-5-tert-butyl-3-[(2R)-tetrahydrofuran-2-ylmethyl]-1,3-thiazol-2(3H)-ylidene]-2-(pyrazin-2-ylmethoxy)-5-(trifluoromethyl)benzamide The title compound was prepared from Example 1A and pyrazin-2-ylmethanol according to the procedure of Example 17. $^1$H NMR (300 MHz, DMSO-d$_6$) δ ppm 1.26-1.40 (m, 9 H), 1.50-1.66 (m, 1 H), 1.67-1.95 (m, 3 H), 3.53-3.69 (m, 1 H), 3.69-3.84 (m, 1 H), 4.04-4.41 (m, 3 H), 5.45 (s, 2 H), 7.21-7.33 (m, 1 H), 7.43 (d, J=8.7 Hz, 1 H), 7.79 (dd, J=8.9, 2.2 Hz, 1 H), 8.10 (d, J=2.4 Hz, 1 H), 8.57-8.75 (m, 2 H), 8.98 (s, 1 H). MS (DCI/NH$_3$) m/z 521 (M+H)$^+$. Anal. calcd for C$_{25}$H$_{27}$F$_3$N$_4$O$_3$S: C, 57.68; H, 5.23; N, 10.76. Found: C, 57.72; H, 5.17; N, 10.45.

Example 20

N-[(2Z)-5-tert-butyl-3-[(2R)-tetrahydrofuran-2-ylmethyl]-1,3-thiazol-2(3H)-ylidene]-2-[(1-oxidopyridin-2-yl)methoxy]-5-(trifluoromethyl)benzamide The title compound was prepared from Example 1A and pyridin-2-ylmethanol N-oxide according to the procedure of Example 17. $^1$H NMR (300 MHz, DMSO-d$_6$) δ ppm 1.34 (s, 9 H), 1.49-1.69 (m, 1 H), 1.67-1.97 (m, 3 H), 3.55-3.67 (m, 1 H), 3.69-3.84 (m, 1 H), 4.13-4.37 (m, 3 H), 5.41 (s, 2 H), 7.28 (s, 1 H), 7.32-7.50 (m, 3 H), 7.70-7.86 (m, 2H), 8.13 (d, J=2.4 Hz, 1 H), 8.29-8.44 (m, 1 H). MS (DCI/NH$_3$) m/z 535 (M+H)$^+$. Anal. calcd for C$_{26}$H$_{28}$F$_3$N$_3$O$_4$S: C, 57.34; H, 5.37; N, 7.72. Found: C, 57.44; H, 5.28; N, 7.50.

Example 21

N-[(2Z)-5-tert-butyl-3-[(2R)-tetrahydrofuran-2-ylmethyl]-1,3-thiazol-2(3H)-ylidene]-2-(pyridin-3-ylmethoxy)-5-(trifluoromethyl)benzamide The title compound was prepared from Example 1A and pyridin-3-ylmethanol according to the procedure of Example 17. $^1$H NMR (300 MHz, DMSO-d$_6$) δ ppm 1.32 (s, 9H), 1.47-1.67 (m, 1 H), 1.67-1.95 (m, 3 H), 3.53-3.88 (m, 2 H), 4.05-4.33 (m, 3 H), 5.35 (s, 2 H), 7.26 (s, 1 H), 7.32-7.52 (m, 2 H), 7.78 (dd, J=8.8, 2.0 Hz, 1 H), 7.84-7.98 (m, 1H), 8.03 (d, J=2.4 Hz, 1 H), 8.54 (dd, J=4.7, 1.7 Hz, 1 H), 8.74 (d, J=1.7 Hz, 1 H). MS (DCI/NH$_3$) m/z 520 (M+H)$^+$. Anal. calcd for C$_{26}$H$_{28}$F$_3$N$_3$O$_3$S: C, 60.10; H, 5.43; N, 8.09. Found: C, 60.15; H, 5.40; N, 7.70

Example 22

N-[(2Z)-5-tert-butyl-3-[(2R)-tetrahydrofuran-2-ylmethyl]-1,3-thiazol-2(3H)-ylidene]-2-[(2R)-tetrahydrofuran-2-ylmethoxy]-5-(trifluoromethyl)benzamide Example 22A (R)-5-tert-butyl-3-((tetrahydrofuran-2-yl)methyl) thiazol-2(3H)-imine hydroiodide To a solution of 3,3-dimethylbutanal (9.90 g, 99 mmol) in acetonitrile (60 mL) were added molecular sieves (8 g) and (R)-(tetrahydrofuran-2-yl)methanamine (10 g, 99 mmol). The reaction mixture was stirred at room temperature for 24 hours and then filtered through celite. To the filtrate was added potassium thiocyanate (12.78 g, 131 mmol). The temperature was adjusted to 50° C. and the mixture was stirred until the solids were dissolved. Then, iodine (25.09 g, 99 mmol) was added to the mixture and stirred at 50° C. for 24 hours. The reaction mixture was cooled, and to the mixture was added sodium meta-bisulfite 20% (100 mL) and stirred for 30 min. The organic layers were separated and the aqueous layer was washed with dichloromethane (3×40 mL). The combined organic extracts were dried with sodium sulfate, filtered and concentrated to obtain the crude product as a yellow solid. The residue was taken into dichloromethane (20 mL) and ethyl acetate (80 mL), the mixture was warmed to 40° C., sonicated, and cooled to between 0-10° C. The solid was collected and washed with cold ethyl acetate to obtain the title compound (18.2 g, 50%). $^1$H NMR (300 MHz, DMSO-d$_6$) δ ppm 1.27 (s, 9 H) 1.48-1.61 (m, 1 H) 1.78-1.93 (m, 2 H) 1.94-2.07 (m, 1 H) 3.62-3.71 (m, 1 H) 3.76-3.84 (m, 1 H) 3.92-4.08 (m, 2 H) 4.11-4.20 (m, 1 H) 7.19 (s, 1 H) 9.39 (s, 2 H); MS (DCI/NH$_3$) m/z 241 (M+H)$^+$.

Example 22B

N-[(2Z)-5-tert-butyl-3-[(2R)-tetrahydrofuran-2-ylmethyl]-1,3-thiazol-2(3H)-ylidene]-2-fluoro-5-(trifluoromethyl)benzamide To a solution of Example 22A (6 g, 24.96 mmol) in dichloromethane (50 mL) in a 250 ml, round bottom flask was added triethylamine (8.70 mL, 62.4 mmol), followed by addition of 2-fluoro-5-(trifluoromethyl)benzoyl chloride (3.78 mL, 24.96 mmol) dropwise and the reaction mixture was stirred for 2 hours at room temperature. The reaction was washed with water and the organic layer was dried with sodium sulfate, filtered and concentrated in vacuo. The residue was purified by Analogix® Intelliflash280™ (SiO$_2$, 0-30% hexanes in ethyl acetate) to afford the title compound as a viscous liquid (7.14 g, 66.4% yield). $^1$H NMR (300 MHz, DMSO-d$_6$) δ ppm 1.33 (s, 9 H) 1.62-1.72 (m, 1 H) 1.78-1.88 (m, 2 H) 1.89-1.99 (m, 1 H) 3.62-3.70 (m, 1 H) 3.75-3.83 (m, 1 H) 4.22-4.29 (m, 2 H) 4.29-4.37 (m, 1 H) 7.34 (s, 1 H) 7.48-7.57 (m, 1 H) 7.86-7.97 (m, 1 H) 8.31 (dd, J=6.78, 2.37 Hz, 1 H); MS (DCI/NH$_3$) m/z 431 (M+H)$^+$.

Example 22C

N-[(2Z)-5-tert-butyl-3-[2R)-tetrahydrofuran-2-ylmethyl]-1,3-thiazol-2(3H)-ylidene]-2-[(2R)-tetrahydrofuran-2-ylmethoxy]-5-(trifluoromethyl)benzamide In a 50 mL round-bottomed flask, (R)-(tetrahydrofuran-2-yl)methanol (176 mg, 1.74 mmol) was dissolved in tetrahydrofuran (8 ml). Sodium t-butoxide (176 mg, 1.83 mmol) was added and stirred at room temperature for 20 min before Example 22B (375 mg, 0.87 mmol) in tetrahydrofuran (5 mL) was added and stirred for 2 hours. The reaction was quenched with saturated ammonium chloride solution and extracted with ethyl acetate (3×20 ml). The organics were combined, washed with brine, dried with sodium sulfate, filtered, and concentrated in vacuo. The residue was purified by Analogix® Intelliflash280™ (SiO$_2$, 0-30% hexanes in ethyl acetate) to afford the title compound (210 mg, 47% yield). $^1$H NMR (300 MHz, DMSO-d$_6$) δ ppm 1.32 (s, 9 H) 1.59-1.68 (m, 1 H) 1.75-2.00 (m, 7 H) 3.60-3.69 (m, 2 H) 3.70-3.82 (m, 2 H) 4.04-4.10 (m, 2 H) 4.11-4.24 (m, 3 H) 4.25-4.32 (m, 1 H) 7.25 (s, 1 H) 7.28 (d, J=8.82 Hz, 1 H) 7.73 (dd, J=8.65, 1.87 Hz, 1 H) 7.94 (d, J=2.37 Hz, 1H); MS (DCI/NH$_3$) m/z 513 (M+H)$^+$. Anal. calcd C$_{25}$H$_{31}$F$_3$N$_2$O$_4$S: C, 58.58; H, 6.1; N, 5.47. Found: C, 58.34; H, 6.22; N, 5.28.

Example 23

N-[(2Z)-5-tert-butyl-3-[(2R)-tetrahydrofuran-2-ylmethyl]-1,3-thiazol-2(3H)-ylidene]-2-[(2S)-tetrahydrofuran-2-ylmethoxy]-5-(trifluoromethyl)benzamide The title compound was prepared and isolated as described in Example 22C, substituting (S)— tetrahydrofuran-2-yl) methanol for (R)-(tetrahydrofuran-2-yl)methanol in 39% yield. $^1$H NMR (300 MHz, DMSO-d$_6$) δ ppm 1.32 (s, 9 H) 1.57-1.68 (m, 1 H) 1.75-2.01 (m, 7 H) 3.61-3.68 (m, 2 H) 3.71-3.80 (m, 2 H) 4.03-4.11 (m, 2 H) 4.15-4.30 (m, 4H) 7.25 (s, 1 H) 7.28 (d, J=8.72 Hz, 1 H) 7.73 (dd, J=8.73, 2.38 Hz, 1 H) 7.94 (d, J=2.38 Hz, 1 H); MS (DCI/NH$_3$) m/z 513 (M+H)$^+$. Anal. calcd C$_{25}$H$_{31}$F$_3$N$_2$O$_4$S: C, 58.58; H, 6.1; N, 5.47. Found: C, 58.43; H, 6.23; N, 5.30.

Example 24

N-[(2Z)-5-tert-butyl-3-[(2R)-tetrahydrofuran-2-ylmethyl]-1,3-thiazol-2(3H)-ylidene]-2-{[(2S)-1-methylpyrrolidin-2-yl]methoxy}-5-(trifluoromethyl)benzamide The title compound was prepared as described in Example 22C, substituting (S)-(1-methylpyrrolidin-2-yl)methanol for (R)-(tetrahydrofuran-2-yl)methanol and the residue was purified by Analogix® Intelliflash280™ (SiO$_2$; gradient elution over 25 min with solvents A:B (100:0 to 90:10); solvent A=CH$_2$Cl$_2$; solvent B=7M NH$_3$/MeOH (1):CH$_2$Cl$_2$ (9)). $^1$H NMR (300 MHz, DMSO-d$_6$) δ ppm 1.32 (s, 9 H) 1.55-1.69 (m, 4 H) 1.78-1.83 (m, 2 H) 1.85-1.95 (m, 2 H) 2.17 (q, J=8.70 Hz, 1 H) 2.33 (s, 3 H) 2.58-2.61 (m, 1 H) 2.88-2.97 (m, 1 H) 3.61-3.69 (m, 1 H) 3.74-3.82 (m, 1 H) 3.93-4.01 (m, 1 H) 4.03-4.07 (m, 1 H) 4.17-4.22 (m, 2 H) 4.22-4.32 (m, 1 H) 7.25 (s, 1 H) 7.28 (d, J=8.82 Hz, 1 H) 7.72 (dd, J=8.82, 2.03 Hz, 1 H) 7.92 (d, J=2.37 Hz, 1 H); MS (DCI/NH$_3$) m/z 526 (M+H)$^+$. Anal. calcd C$_{25}$H$_{32}$F$_3$N$_3$O$_3$S.0.1 EtOAc: C, 58.79; H, 6.39; N, 8.10. Found: C, 59.15; H, 6.79; N, 8.01.

Example 25

N-[(2Z)-5-tert-butyl-3-[(2R)-tetrahydrofuran-2-ylmethyl]-1,3-thiazol-2(3H)-ylidene]-2-[(2R)-pyrrolidin-2-ylmethoxy]-5-(trifluoromethyl)benzamide

Example 25A tert-butyl (2R)-2-{[2-{[(2Z)-5-tert-butyl-3-[(2R)-tetrahydrofuran-2-ylmethyl]-1,3-thiazol-2(3H)-ylidene]carbamoyl}-4-(trifluoromethyl)phenoxy]methyl}pyrrolidine-1-carboxylate The title compound was prepared and isolated as described in Example 22C, substituting (R)-tert-butyl 2-(hydroxymethyl)pyrrolidine-1-carboxylate for (R)-(tetrahydrofuran-2-yl)methanol in 40% yield. $^1$H NMR (300 MHz, DMSO-d$_6$) δ ppm 1.32 (s, 9 H) 1.39 (s, 9 H) 1.59-1.73 (m, 2 H) 1.76-1.85 (m, 2 H) 1.89-1.99 (m, 4 H) 3.16-3.27 (m, 2 H) 3.60-3.69 (m, 1 H) 3.74-3.82 (m, 1 H) 3.97-4.11 (m, 2 H) 4.15-4.30 (m, 4 H) 7.26 (s, 1 H) 7.30-7.33 (m, 1 H) 7.72 (dd, J=8.82, 2.03 Hz, 1 H) 7.91-7.94 (m, 1 H); MS (DCI/NH$_3$) m/z 612 (M+H)$^+$.

Example 25B

N-[(2Z)-5-tert-butyl-3-[(2R)-tetrahydrofuran-2-ylmethyl]-1,3-thiazol-2(3H)-ylidene]-2-[(2R)-pyrrolidin-2-ylmethoxy]-5-(trifluoromethyl)benzamide To a solution of Example 25A (440 mg, 0.72 mmol) in dichloromethane (1 mL) was added trifluoroacetic acid (0.5 mL) and stirred at room temperature for 2 hours. The reaction was concentrated, taken up in dichloromethane and washed with saturated sodium bicarbonate solution. The aqueous layer was washed with dichloromethane. The combined organic layers were dried over sodium sulfate, and concentrated in vacuo. The residue was purified by preparative HPLC on a Waters Symmetry C8 column (25 mm×100 mm, 7 gm particle size) using a gradient of 10-100% acetonitrile (A) and 10 mM ammonium acetate in water (B), at a flow rate of 2.0 mL/min (0-0.1 min 10% A, 0.1-2.6 min 10-100% A, 2.6-2.9 min 100% A, 2.9-3.0 min 100-10% A. 0.5 min post-nm delay) to obtain the title compound (350 mg , 95%). $^1$H NMR (300 MHz, DMSO-d$_6$) δ ppm 1.33 (s, 9 H) 1.39-1.53 (m, 1 H) 1.57-1.69 (m, 1 H) 1.76-1.95 (m, 5 H) 2.40-2.46 (m, 1 H) 2.63-2.74 (m, 2 H) 2.80-2.89 (m, 2 H) 3.58-3.69 (m, 1 H) 3.75-3.82 (m, 1 H) 3.95-4.09 (m, 2 H) 4.18-4.31 (m, 3 H) 7.24-7.29 (m, 2 H) 7.74 (dd, J=8.92, 2.58 Hz, 1 H) 7.99 (d, J=2.38 Hz, 1 H); MS (DCI/NH$_3$) m/z 512 (M+H)$^+$.

Example 26

N-[(2Z)-5-tert-butyl-3-[(2R)-tetrahydrofuran-2-ylmethyl]-1,3-thiazol-2(3H)-ylidene]-2-{[(2R)-1-methylpyrrolidin-2-yl]methoxy}-5-(trifluoromethyl)benzamide To a solution of Example 25B (250 mg, 0.489 mmol) in dichloromethane (2 mL) was added formaldehyde (147 mg, 1.466 mmol), acetic acid (29.3 mg, 0.489 mmol), and sodium triacetoxyhydroborate (311 mg, 1.466 mmol). The mixture was stirred at room temperature for 2 hours. The reaction was quenched with saturated aqueous sodium bicarbonate and extracted by dichloromethane (3×10 mL). The combined organic layers were concentrated under reduced pressure, and the residue was purified by Analogix® Intelliflash280™ (SiO$_2$; gradient elution over 25 min with solvents A:B (100:0 to 90:10); solvent A=CH$_2$Cl$_2$; solvent B=7M NH$_3$/MeOH (1):CH$_2$Cl$_2$ (9)) to afford the title compound as a yellow oil (190 mg, 0.361 mmol, 74.0% yield). $^1$H NMR (300 MHz, DMSO-d$_6$) δ ppm 1.32 (s, 9 H) 1.53-1.68 (m, 4 H) 1.76-1.85 (m, 2 H) 1.85-1.96 (m, 2 H) 2.12-2.21 (m, 1 H) 2.32 (s, 3 H) 2.56-2.60 (m, 1 H) 2.88-2.96 (m, 1 H) 3.60-3.69 (m, 1 H) 3.74-3.82 (m, 1 H) 3.93-4.00 (m, 1H) 4.02-4.09 (m, 1 H) 4.18-4.22 (m, 2 H) 4.23-4.32 (m, 1 H) 7.25 (s, 1 H) 7.28 (d, J=8.72 Hz, 1 H) 7.73 (dd, J=8.72, 2.38 Hz, 1 H) 7.92 (d, J=2.38 Hz, 1 H); MS (DCI/NH$_3$) m/z 526 (M+H)$^+$. Anal. calcd C$_{26}$H$_{34}$F$_3$N$_3$O$_3$S 0.5H2O: C, 58.41; H, 6.60; N, 7.86; Found: C, 58.38; H, 6.84; N, 7.68.

Example 27

N-[(2Z)-5-tert-butyl-3-[(2R)-tetrahydrofuran-2-ylmethyl]-1,3-thiazol-2(3H)-ylidene]-2-[2-(1-methylpyrrolidin-2-yl)ethoxy]-5-(trifluoromethyl)benzamide The title compound was prepared as described in Example 22C, substituting 2-(1-methylpyrrolidin-2-yl)ethanol for (R)-(tetrahydrofuran-2-yl)methanol and the residue was purified by Analogix® Intelliflash280™ (SiO$_2$; gradient elution over 25 min with solvents A:B (100:0 to 90:10); solvent A=CH$_2$Cl$_2$; solvent B=7M NH$_3$/MeOH (1):CH$_2$Cl$_2$ (9)) in 64% yield. $^1$H NMR (300 MHz, DMSO-d$_6$) δ ppm 1.33 (s, 9 H) 1.44-1.53 (m, 1 H) 1.54-1.66 (m, 4 H) 1.78-1.92 (m, 4 H) 1.98-2.06 (m, 2 H) 2.12-2.20 (m, 4 H) 2.87-2.95 (m, 1H) 3.60-3.69 (m, 1 H) 3.74-3.82 (m, 1 H) 4.10-4.15 (m, 2 H) 4.18-4.20 (m, 2 H) 4.24-4.33 (m, 1 H) 7.24-7.28 (m, 2 H) 7.72 (dd, J=8.48, 2.03 Hz, 1 H) 7.90 (d, J=2.37 Hz, 1 H); MS (DCI/NH$_3$) m/z 540 (M+H)$^+$. Anal. calcd C$_{27}$H$_{36}$F$_3$N$_3$O$_3$S 0.2H2O: C, 59.69; H, 6.75; N, 7.73. Found: C, 59.66; H, 6.68; N, 6.59.

Example 28

N-[(2Z)-5-tert-butyl-3-[(2R)-tetrahydrofuran-2-ylmethyl]-1,3-thiazol-2(3H)-ylidene]-2-[(3R)-pyrrolidin-3-ylmethoxy]-5-(trifluoromethyl)benzamide Example 28A tert-but (3R)-3-{[2-{[(2Z)-5-tert-butyl-3-[(2R)-tetrahydrofuran-2-ylmethyl]-1,3-thiazol-2(3H)-ylidene]carbamoyl}-4-(trifluoromethyl)phenoxy]methyl}pyrrolidine-1-carboxylate The title compound was prepared and isolated as described in Example 22C, substituting ((R)-tert-butyl 3-(hydroxymethyl)pyrrolidine-1-carboxylate for (R)-(tetrahydrofuran-2-yl)methanol in 67% yield. $^1$H NMR (300 MHz, DMSO-d$_6$) δ ppm 1.32 (s, 9 H) 1.38-1.39 (m, 9 H) 1.57-1.68 (m, 1 H) 1.74-1.84 (m, 3 H) 1.86-1.97 (m, 2 H) 3.08-3.10 (m, 1 H) 3.16-3.27 (m, 2 H) 3.37-3.48 (m, 1 H) 3.61-3.68 (m, 1 H) 3.74-3.82 (m, 1 H) 4.02-4.17 (m, 2 H) 4.19-4.23 (m, 2 H) 4.25-4.30 (m, 2 H) 7.24-7.27 (m, 1 H) 7.29 (d, J=8.82 Hz, 1 H) 7.74 (dd, J=8.82, 2.03 Hz, 1 H) 7.98-8.01 (m, 1 H); MS (DCI/NH$_3$) m/z 612 (M+H)$^+$.

Example 28B N-[(2Z)-5-tert-butyl-3-[(2R)-tetrahydrofuran-2-ylmethyl]-1,3-thiazol-2(3H)-ylidene]-2-[(3R)-pyrrolidin-3-ylmethoxy]-5-(trifluoromethyl)benzamide The title compound was prepared and isolated as described in Example 25B, substituting Example 28A for Example 25A in 87% yield. $^1$H NMR (300 MHz, DMSO-d$_6$) δ ppm 1.33 (s, 9 H) 1.61-1.73 (m, 1 H) 1.78-1.95 (m, 5 H) 2.05-2.19 (m, 1 H) 2.71-2.83 (m, 1 H) 3.02-3.15 (m, 1 H) 3.17-3.26 (m, 3 H) 3.62-3.69 (m, 1 H) 3.74-3.83 (m, 1 H) 4.10-4.15 (m, 1 H) 4.17-4.33 (m, 4 H) 7.29 (d, J=8.73 Hz, 1 H) 7.34 (s, 1 H) 7.82 (dd, J=8.72, 2.38 Hz, 1 H) 8.23 (d, J=2.38 Hz, 1 H); MS (DCI/NH$_3$) m/z 512 (M+H)$^+$.

Example 29

N-[(2Z)-5-tert-butyl-3-[(2R)-tetrahydrofuran-2-ylmethyl]-1,3-thiazol-2(3H)-ylidene]-2-[(3S)-pyrrolidin-3-ylmethoxy]-5-(trifluoromethyl)benzamide Example 29A tert-but (3S)-3-{[2-{[(2Z)-5-tert-butyl-3-[(2R)-tetrahydrofuran-2-ylmethyl]-1,3-thiazol-2(3H)-ylidene]carbamoyl}-4-(trifluoromethyl)phenoxy]methyl}pyrrolidine-1-carboxylate The title compound was prepared and isolated as described in Example 22C, substituting ((S)-tert-butyl 3-(hydroxymethyl)pyrrolidine-1-carboxylate for (R)-(tetrahydrofuran-2-yl)methanol in 78% yield. $^1$H NMR (300 MHz, DMSO-d$_6$) δ ppm 1.32 (s, 9 H) 1.36-1.39 (m, 9 H) 1.57-1.71 (m, 2 H) 1.76-1.97 (m, 4 H) 3.08-3.11 (m, 1 H) 3.17-3.28 (m, 2 H) 3.35-3.46 (m, 1 H) 3.61-3.68 (m, 1 H) 3.74-3.82 (m, 1 H) 4.02-4.19 (m, 5 H) 4.24-4.32 (m, 1 H) 7.25-7.27 (m, 1 H) 7.29 (d, J=8.82 Hz, 1 H) 7.74 (dd, J=8.82, 2.03 Hz, 1 H) 7.98-8.00 (m, 1 H); MS (DCI/NH$_3$) m/z 612 (M+H)$^+$.

Example 29B

N-[(2Z)-5-tert-butyl-3-[(2R)-tetrahydrofuran-2-ylmethyl]-1,3-thiazol-2(3H)-ylidene]-2-[3S)-pyrrolidin-3-ylmethoxy]-5-(trifluoromethyl)benzamide The title compound was prepared and isolated as described in Example 25B, substituting Example 29A for Example 25A in 89% yield. $^1$H NMR (300 MHz, DMSO-d$_6$) δ ppm 1.30-1.34 (m, 9 H) 1.62-1.72 (m, 1 H) 1.76-1.97 (m, 5 H) 2.16-2.27 (m, 1 H) 2.66-2.82 (m, 2 H), 3.17-3.26 (m, 1 H) 3.27-3.40 (m, 2 H) 3.64-3.72 (m, 1 H) 3.73-3.81 (m, 1 H) 4.02-4.32 (m, 4 H) 7.24-7.35 (m, 2 H) 7.69-7.85 (m, 1 H) 7.85-8.27 (m, 1 H); MS (DCI/NH$_3$) m/z 512 (M+H)$^+$.

Example 30

N-[(2Z)-5-tert-butyl-3-[(2R)-tetrahydrofuran-2-ylmethyl]-1,3-thiazol-2(3H)-ylidene]-2-{[(3R)-1-methylpyrrolidin-3-yl]methoxy}-5-(trifluoromethyl)benzamide The title compound was prepared and isolated as described in Example 26, substituting Example 28B for Example 25B in 91% yield. $^1$H NMR (300 MHz, DMSO-d$_6$) δ ppm 1.32 (s, 9 H) 1.44-1.57 (m, 1 H) 1.58-1.68 (m, 1 H) 1.78-1.93 (m, 4 H) 2.21 (s, 3 H) 2.26-2.42 (m, 3 H) 3.61-3.69 (m, 1 H) 3.74-3.82 (m, 1 H) 3.96-4.00 (m, 2 H) 4.18-4.23 (m, 2 H) 4.23-4.32 (m, 1 H) 7.24-7.30 (m, 2 H) 7.73 (dd, J=8.82, 2.37 Hz, 1 H) 7.94 (d, J=2.03 Hz, 1 H); MS (DCI/NH$_3$) m/z 526 (M+H)$^+$. Anal.

calcd C$_{26}$H$_{34}$F$_3$N$_3$O$_3$S 1.0H$_2$O: C, 57.44; H, 6.67; N, 7.73; Found: C, 57.35; H, 6.31; N, 7.65.

Example 31

N-[(2Z)-5-tert-butyl-3-[(2R)-tetrahydrofuran-2-ylmethyl]-1,3-thiazol-2(3H)-ylidene]-2-{[(3 S)-1-methylpyrrolidin-3-yl]methoxy}-5-(trifluoromethyl)benzamide The title compound was prepared and isolated as described in Example 26, substituting Example 29B for Example 25B in 86% yield. $^1$H NMR (300 MHz, DMSO-d$_6$) δ ppm 1.35 (s, 9 H) 1.61-1.72 (m, 1 H) 1.78-1.88 (m, 4 H) 1.91-1.99 (m, 1 H) 2.16-2.26 (m, 1 H) 2.69 (s, 3 H) 2.70-2.81 (m, 2 H) 2.87-2.94 (m, 2 H) 3.64-3.71 (m, 1 H) 3.77-3.84 (m, 1 H) 4.14-4.16 (m, 2 H) 4.24-4.32 (m, 3 H) 7.24-7.27 (m, 2 H) 7.74-7.77 (m, 1H) 8.21-8.23 (m, 1 H); MS (DCI/NH$_3$) m/z 526 (M+H)$^+$.

Example 32

2-[(4-benzylmorpholin-2-yl)methoxy]-N-[(2Z)-5-tert-butyl-3-[(2S)-tetrahydrofuran-2-ylmethyl]-1,3-thiazol-2(3H)-ylidene]-5-(trifluoromethyl)benzamide Example 32A (4-benzylmorpholin-2-yl)methanol To a solution of 4-benzylmorpholine-2-carboxylic acid (5 g, 22.6 mmol) and triethylamine (3.35 mL, 24 mmol) in THF (100 mL) at −10° C. in a flask equipped with a condenser was added ethyl carbonochloridate (2.5 g, 23 mmol) dropwise and the mixture was stirred at −10° C. to −5° C. for 20 min. Sodium borohydride (2.27 g, 60 mmol) was added followed by methanol (25 mL) from the top of the condenser at such rate to maintain the temperature between 0-5° C. The reaction mixture was allowed to warm to room temperature, acidified to pH 5 with the addition of 10% aqueous citric acid, and concentrated under reduced pressure. The residue was dissolved in EtOAc, washed with water, brine, and dried with MgSO$_4$. Purification of the residue by column chromatography (SiO$_2$, eluted with EtOAc) afforded 3 g of the title compound. MS (DCI/NH$_3$) m/z 208 (M+H)$^+$.

Example 32B

N-[(2Z)-5-tert-butyl-3-[(2S)-tetrahydrofuran-2-ylmethyl]-1,3-thiazol-2(3H)-ylidene]-2-fluoro-5-(trifluoromethyl)benzamide The title compound was prepared as described in Example 1A substituting (S)-5-tert-butyl-3-(2-(tetrahydrofuran-2-yl)ethyl)thiazol-2(3H)-imine (prepared as described in WO2009067613) for Example 22A. MS (DCI/NH$_3$) m/z 431 (M+H)$^+$.

Example 32C

2-[(4-benzylmorpholin-2-yl)methoxy]-N-[(2Z)-5-tert-butyl-3-[(2S)-tetrahydrofuran-2-ylmethyl]-1,3-thiazol-2(3H)-ylidene]-5-(trifluoromethyl)benzamide To a solution of Example 32B (103 mg, 0.24 mmol) and Example 32A (50 mg, 0.24 mmol) in anhydrous THF (10 mL) at room temperature was added 1N potassium tert-butoxide (0.24 mL, 0.24 mmol) and the mixture was stirred at ambient temperature for 1 hour. The mixture was concentrated under reduced pressure. The residue was dissolved in EtOAc, washed with water, saturated sodium bicarbonate, brine, and dried with MgSO$_4$. Purification of the residue by chromatography (SiO$_2$, eluted with EtOAc-MeOH 9:1) afforded 130 mg of the title compound. $^1$H NMR (300 MHz, DMSO-d$_6$) δ ppm 1.30-1.37 (m, 9 H), 1.57-1.69 (m, 1 H), 1.75-2.14 (m, 4 H), 2.57-2.67 (m, 1 H), 2.84 (d, J=11.2 Hz, 1 H), 3.45 (s, 2 H), 3.48-3.59 (m, 1 H), 3.66 (t, J=7.5 Hz, 1 H), 3.73-3.84 (m, 3 H), 3.96-4.35 (m, 7H), 7.17-7.33 (m, 6 H), 7.72 (dd, J=9.0, 2.2 Hz, 1 H), 7.94 (s, 1 H); MS (DCI/NH$_3$) m/z 618 (M+H)$^+$.

Example 33

2-{[(2R)-2-amino-3-hydroxypropyl]oxy}-N-[(2Z)-5-tert-butyl-3-[(2S)-tetrahydrofuran-2-ylmethyl]-1,3-thiazol-2(3H)-ylidene]-5-(trifluoromethyl)benzamide Example 33A tert-butyl (1R)-2-{[tert-butyl(dimethyl)silyl]oxy}-1-{[2-({[(2Z)-5-tert-butyl-3-[(2S)-tetrahydrofuran-2-ylmethyl]-1,3-thiazol-2(3H)-ylidene]amino}carbonyl)-4-(trifluoromethyl)phenoxy]methyl}ethylcarbamate A mixture of Example 32B (87 mg, 0.2 mmol), (R)-tert-butyl 2-{[tert-butyl(dimethyl)silyl]oxy}-1-(hydroxymethyl)ethylcarbamate (62 mg, 0.2 mmol) and 1N potassium tert-butoxide in THF (0.2 mL, 0.2 mmol) in THF (10 mL) was stirred at room temperature for 1 hour. The mixture was concentrated under reduced pressure and the residue was partitioned between EtOAc and water. The organic layer was washed with brine, dried with MgSO$_4$ and concentrated under reduced pressure to afford 100 mg of the title compound. MS (DCI/NH$_3$) m/z 716 (M+H)$^+$.

Example 33B

2-{[(2R)-2-amino-3-hydroxypropyl]oxy}-N-[(2Z)-5-tert-butyl-3-[(2S)-tetrahydrofuran-2-ylmethyl]-1,3-thiazol-2(3H)-ylidene]-5-(trifluoromethyl)benzamide A solution of Example 33A (100 mg, 0.14 mmol) in CH$_2$Cl$_2$ (5 mL) at 0° C. was treated with trifluoroacetic acid (0.1 mL, 1.1 mmol). The mixture was allowed to warm to room temperature and stirred for 3 hours. The mixture was concentrated under reduced pressure, diluted with saturated NaHCO$_3$ and extracted with EtOAc. The organic layer was washed with brine, dried with MgSO$_4$ and concentrated under reduced pressure. Purification by chromatography (SiO$_2$, eluted with CH$_2$Cl$_2$-MeOH 6:1) afforded 26 mg of the title compound. $^1$H NMR (300 MHz, DMSO-d$_6$) δ ppm 1.33 (s, 9 H), 1.58-1.73 (m, 1 H), 1.75-2.04 (m, 3 H), 2.25-2.43 (m, 1 H), 3.08 (q, J=5.6 Hz, 1 H), 3.36-3.53 (m, 3 H), 3.59-3.69 (m, 1 H), 3.74-3.86 (m, 1 H), 3.94-4.01 (m, 1 H), 4.05-4.12 (m, 1 H), 4.19-4.36 (m, 3H), 4.68 (t, J=5.2 Hz, 1 H), 7.24-7.34 (m, 2 H), 7.76 (dd, J=8.9, 2.2 Hz, 1 H), 8.07 (d, J=2.4 Hz, 1 H); MS (DCI/NH$_3$) m/z 502 (M+H)$^+$. Anal calculated for C$_{23}$H$_{30}$F$_3$N$_3$O$_4$S.0.5H$_2$O: C, 54.11, H, 6.12; N, 8.23. Found: C, 54.15; H, 6.23; N, 7.77.

Example 34

N-[(2Z)-5-tert-butyl-3-[(2S)-tetrahydrofuran-2-ylmethyl]-1,3-thiazol-2(3H)-ylidene]-2-[(1,4-dimethylpiperazin-2-yl)methoxy]-5-(trifluoromethyl)benzamide A mixture of Example 32B (108 mg, 0.25 mmol) and (1,4-dimethylpiperazin-2-yl)methanol (72 mg, 0.5 mmol)

were processed using method described in Example 32B to afford the title compound. $^1$H NMR (500 MHz, pyridine-d$_5$) δ ppm 1.17-1.26 (m, 9 H), 1.50-1.72 (m, 3 H), 1.86 (dd, J=12.5, 6.1 Hz, 1 H), 2.25 (s, 3 H), 2.31-2.55 (m, 7 H), 2.62 (d, J=10.1 Hz, 1 H), 2.74 (d, J=11.3 Hz, 1 H), 3.19 (d, J=10.7 Hz, 1 H), 3.65 (q, J=7.2 Hz, 1 H), 3.82 (q, J=6.9 Hz, 1 H), 4.16-4.38 (m, 3 H), 4.43-4.56 (m, 2 H), 7.20 (s, 1 H), 7.27 (d, J=8.5 Hz, 1 H), 7.71-7.80 (m, 1 H), 8.55 (s, 1 H); MS (DCI/NH$_3$) m/z 555 (M+H)$^+$.

Example 35

N-[(2Z)-5-tert-butyl-3-[(2R)-tetrahydrofuran-2-ylmethyl]-1,3-thiazol-2(3H)-ylidene]-2-{2-[methyl(phenyl)amino]ethoxy}-5-(trifluoromethyl)benzamide The title compound prepared as described in Example 1B substituting 2-(methyl(phenyl)amino)ethanol for (R)-tert-butyl 2-(hydroxymethyl)azetidine-1-carboxylate. $^1$H NMR (300 MHz, DMSO-d$_6$) δ ppm 1.34 (s, 9 H), 1.53-1.69 (m, 1 H), 1.72-1.95 (m, 3H), 2.90 (s, 3 H), 3.59-3.82 (m, 4 H), 4.12-4.32 (m, 5 H), 6.58 (t, J=7.29 Hz, 1 H), 6.73 (d, J=7.80 Hz, 2 H), 7.06-7.13 (m, 2 H), 7.23-7.28 (m, 2 H), 7.71 (dd, J=8.82, 2.37 Hz, 1 H), 7.92 (d, J=2.37 Hz, 1 H); MS (DCI/NH$_3$) m/z 562 [M+H]$^+$.

Example 36

2-(benzyloxy)-N-[(2Z)-5-tert-butyl-3-[(2R)-tetrahydrofuran-2-ylmethyl]-1,3-thiazol-2(3H)-ylidene]-5-(trifluoromethyl)benzamide The title compound was prepared as described in example 2A substituting (S)-tert-butyl 2-(hydroxymethyl)azetidine-1-carboxylate with benzyl alcohol. $^1$H NMR (300 MHz, DMSO-D6) δ ppm 1.27-1.38 (m, 9 H), 1.47-1.66 (m, 1 H), 1.66-1.90 (m, 3 H), 3.52-3.84 (m, 2 H), 4.10-4.31 (m, 3 H), 5.23-5.39 (m, 2 H), 7.19-7.45 (m, 5 H), 7.44-7.59 (m, 2 H), 7.73 (dd, J=8.8, 2.0 Hz, 1 H), 7.87-8.07 (m, 1 H). MS (DCI/NH$_3$) m/z 519 (M+H)$^+$. Anal. calcd for C$_{27}$H$_{29}$F$_3$N$_2$O$_3$S: C, 62.53; H, 5.64; N, 5.40. Found: C, 65.52; H, 5.12; N, 3.49.

Example 37

N-[(2Z)-5-tert-butyl-3-[(2R)-tetrahydrofuran-2-ylmethyl]-1,3-thiazol-2(3H)-ylidene]-2-(1,3-oxazol-5-ylmethoxy)-5-(trifluoromethyl)benzamide The title compound was prepared as described in example 2A substituting (5)-tert-butyl 2-(hydroxymethyl)azetidine-1-carboxylate with oxazol-5-ylmethanol. $^1$H NMR (300 MHz, CDCl$_3$) δ ppm 1.29-1.41 (m, 9 H), 1.60-2.14 (m, 4 H), 3.66-3.97 (m, 2 H), 4.09-4.32 (m, 2 H), 4.37 (dd, J=13.2, 2.7 Hz, 1 H), 5.27 (s, 2 H), 6.79-6.96 (m, 1 H), 7.07-7.21 (m, 2 H), 7.54-7.67 (m, 1 H), 7.84-7.96 (m, 1 H), 8.26 (d, J=2.0 Hz, 1 H). MS (DCI/NH$_3$) m/z 510 (M+H)$^+$. Anal. calcd for C$_{24}$H$_{26}$F$_3$N$_3$O$_4$S: C, 56.57; H, 5.14; N, 8.25. Found: C, 56.54; H, 5.06; N, 8.11

Example 38

N-[(2Z)-5-tert-butyl-3-[(2R)-tetrahydrofuran-2-ylmethyl]-1,3-thiazol-2(3H)-ylidene]-2-(1,3-thiazol-2-ylmethoxy)-5-(trifluoromethyl)benzamide The title compound was prepared as described in example 2A substituting (5)-tert-butyl 2-(hydroxymethyl)azetidine-1-carboxylate with thiazol-2-ylmethanol. $^1$H NMR (300 MHz, DMSO-d$_6$) δ ppm 1.25-1.40 (m, 9 H), 1.48-1.67 (m, 1 H), 1.67-1.93 (m, 3 H), 3.56-3.87 (m, 2 H), 4.08-4.33 (m, 3 H), 5.60 (s, 2 H), 7.25 (s, 1 H), 7.42 (d, J=8.8 Hz, 1 H), 7.66-7.93 (m, 3 H), 8.01 (d, J=2.0 Hz, 1 H). MS (DCI/NH$_3$) m/z 526 (M+H)$^+$.

Example 39

2-(2-tert-butylhydrazino)-N-[(2Z)-5-tert-butyl-3-[(2R)-tetrahydrofuran-2-ylmethyl]-1,3-thiazol-2(3H)-ylidene]-5-(trifluoromethyl)benzamide A mixture of Example 1A (300 mg, 0.7 mmol), tert-butylhydrazine hydrochloride (261 mg, 2.1 mmol) and potassium carbonate (385 mg, 2.8 mmol) in DMF (15 mL) was stirred at 40° C. for 24 hours. The mixture was poured into water and extracted with ethyl acetate. The acetate extract was washed with water, brine, dried with MgSO$_4$, and concentrated under reduced pressure. Purification by chromatography (SiO$_2$) afforded 70 mg of the title compound. $^1$H NMR (300 MHz, DMSO-d$_6$) δ ppm 1.08 (s, 9 H), 1.30-1.35 (m, 9H), 1.63-2.04 (m, 4 H), 3.68 (t, J=6.7 Hz, 1 H), 3.76-3.88 (m, 1 H), 4.18-4.39 (m, 3 H), 4.62 (s, 1 H), 7.28-7.32 (m, 1 H), 7.46-7.60 (m, 2 H), 8.51 (d, J=1.6 Hz, 1 H), 9.90 (s, 1 H). MS (DCI/NH$_3$) m/z 499 (M+H)$^+$. Anal. calculated for C$_{24}$H$_{33}$F$_3$N$_4$O$_2$S: C, 57.81H, 6.67 N, 11.24. Found: C, 58.22H, 6.72 N, 10.98.

Example 40 tert-butyl 2-[2-({[(2Z)-5-tert-butyl-3-[(2R)-tetrahydrofuran-2-ylmethyl]-1,3-thiazol-2(3H)-ylidene]amino}carbonyl)-4-(trifluoromethyl)phenyl]hydrazinecarboxylate A mixture of Example 1A (203 mg, 0.47 mmol), tert-butyl hydrazinecarboxylate (187 mg, 1.42 mmol) and potassium carbonate (196 mg, 1.42 mmol) in dioxane (15 mL) was warmed to reflux for 24 hours. The mixture was concentrated under reduced pressure and extracted with ethyl acetate. The acetate extract was washed with water, brine, dried with MgSO$_4$ and concentrated under reduced pressure. The residue was purified by chromatography (SiO$_2$) to afford 40 mg of the title compound. $^1$H NMR (300 MHz, DMSO-d$_6$) δ ppm 1.31-1.47 (m, 18 H), 1.64-2.04 (m, 4 H), 3.66 (t, J=7.1 Hz, 1 H), 3.75-3.89 (m, 1 H), 4.23-4.40 (m, 3 H), 6.12 (s, 1 H), 6.99 (d, J=9.1 Hz, 1 H), 7.36 (s, 1 H), 7.65 (dd, J=8.9, 1.8 Hz, 1 H), 8.43 (d, J=2.0 Hz, 1 H), 10.11 (s, 1 H). MS (DCI/NH$_3$) m/z 543 (M+H)$^+$.

Example 41

N-[(2Z)-5-tert-butyl-3-(2-methoxyethyl)-1,3-thiazol-2(3H)-ylidene]-2-(pyrazin-2-ylmethoxy)-5-(trifluoromethyl)benzamide Example 41A (Z)-N-(5-tert-butyl-3-(2-methoxyethyl)thiazol-2(3H)-ylidene)-2-fluoro-5-(trifluoromethyl)benzamide The title compound was prepared as described in Example 1A substituting 5-tert-butyl-3-(2-methoxyethyl)-1,3-thiazol-2(3H)-imine hydrobromide (prepared as described in WO 2009067613) for Example 22A. MS (DCI/NH$_3$) m/z 405 (M+H)$^+$.

Example 41B

N-[(2Z)-5-tert-butyl-3-(2-methoxyethyl)-1,3-thiazol-2(3H)-ylidene]-2-(pyrazin-2-ylmethoxy)-5-(trifluoromethyl)benzamide The title compound was prepared as described in Example 2A substituting Example 41A for Example 1A, and substituting (S)-tert-butyl 2-(hydroxymethyl)azetidine-1-carboxylate with pyrazin-2-ylmethanol. $^1$H NMR (300 MHz, DMSO-$d_6$) δ ppm 1.26-1.40 (m, 9 H), 3.18-3.26 (m, 3 H), 3.66 (t, J=5.6 Hz, 2 H), 4.30 (t, J=5.6 Hz, 2 H), 5.45 (s, 2 H), 7.28 (s, 1 H), 7.43 (d, J=8.7 Hz, 1 H), 7.79 (dd, J=8.7, 2.4 Hz, 1 H), 8.09 (d, J=2.4 Hz, 1 H), 8.54-8.75 (m, 2 H), 8.98 (s, 1 H). MS (DCI/NH$_3$) m/z 495 (M+H)$^+$. Anal. calcd for $C_{23}H_{25}F_3N_4O_3S$: C, 55.86; H, 5.10; N, 11.33. Found: C, 55.80; H, 5.00; N, 11.38

Example 42

N-[(2Z)-5-tert-butyl-3-(2-methoxyethyl)-1,3-thiazol-2(3H)-ylidene]-2-(pyridin-2-ylmethoxy)-5-(trifluoromethyl)benzamide The title compound was prepared as described in Example 2A substituting (5)-tert-butyl 2-(hydroxymethyl)azetidine-1-carboxylate with pyridin-2-ylmethanol and Example 1A with Example 41A. $^1$H NMR (300 MHz, DMSO-$d_6$) δ ppm 1.27-1.39 (m, 9 H), 3.22 (s, 3H), 3.67 (t, J=5.4 Hz, 2 H), 4.29 (t, J=5.4 Hz, 2 H), 5.35 (s, 2 H), 7.27 (s, 1 H), 7.29-7.41 (m, 2 H), 7.64 (d, J=7.8 Hz, 1 H), 7.75 (dd, J=8.6, 1.9 Hz, 1 H), 7.79-7.90 (m, 1 H), 8.03 (d, J=2.0 Hz, 1 H), 8.58 (d, J=5.8 Hz, 1 H). MS (DCI/NH$_3$) m/z 494 (M+H)$^+$. Anal. calcd for $C_{24}H_{26}F_3N_3O_3S$: C, 58.41; H, 5.31; N, 8.51. Found: C, 57.81; H, 4.93; N, 8.31.

Example 43

N-[(2Z)-5-tert-butyl-3-[(2R)-tetrahydrofuran-2-ylmethyl]-1,3-thiazol-2(3H)-ylidene]-2-{[(2S)-1-methyl-5-oxopyrrolidin-2-yl]methoxy}-5-(trifluoromethyl)benzamide To a solution of (S)-5-(hydroxymethyl)-1-methylpyrrolidin-2-one (108 mg, 0.84 mmol) (Williams, P. D. et al. *Journal of Medicinal Chemistry* 1991, 34, 887-900) in 5 mL of THF was added sodium tert-butoxide (100 mg, 1.05 mmol). The mixture was stirred at 22° C. for 20 minutes. The mixture was cooled to 5° C. and a solution of Example 1A (180 mg, 0.42 mmol) in 2 mL of THF was added. The mixture was stirred at 5° C. for 2 hours, then at 22° C. for 1 hour. The solvent was evaporated under reduced pressure. The residue was dissolved in methylene chloride, washed with water, dried over MgSO$_4$ and concentrated. The residue was purified by flash chromatography on SiO$_2$ using an Analogix® Intelliflash280™ (eluted with CH$_2$Cl$_2$:10% MeOH and 3N NH$_3$ in CH$_2$Cl$_2$: 0 to 100%) to afford the title compound; $^1$H NMR (300 MHz, CDCl$_3$) δ ppm 1.36 (s, 9 H), 1.58-1.73 (m, 1 H), 1.74-2.14 (m, 4 H), 2.14-2.42 (m, 2 H), 2.44-2.64 (m, 1 H), 2.91 (s, 3 H), 3.72-3.91 (m, 2 H), 3.93-4.03 (m, 1H), 4.07 (dd, J=12.0, 4.8 Hz, 1 H), 4.14-4.32 (m, 3 H), 4.39 (dd, J=13.3, 2.6 Hz, 1 H), 6.88 (s, 1 H), 6.99 (d, J=8.7 Hz, 1 H), 7.60 (dd, J=8.7, 2.4 Hz, 1 H), 8.11 (d, J=2.4 Hz, 1 H); MS (ESI) m/z 540 (M+H)$^+$.

Example 44

N-[(2Z)-5-tert-butyl-3-[(2R)-tetrahydrofuran-2-ylmethyl]-1,3-thiazol-2(3H)-ylidene]-2-[(2S)-pyrrolidin-2-ylmethoxy]-5-(trifluoromethyl)benzamide

Example 44A

(Z)-2-(((S)-1-benzylpyrrolidin-2-yl)methoxy)-N-(5-tert-butyl-34(R)-tetrahydrofuran-2-yl)methyl)thiazol-2(3H)-ylidene)-5-(trifluoromethyl)benzamide The title compound was prepared and isolated as described in Example 22C, substituting (S)-(−)-1-benzyl-2-pyrrolidinemethanol for (R)-(tetrahydrofuran-2-yl)methanol. $^1$H NMR (300 MHz, DMSO-D6) δ ppm 1.28 (s, 9 H) 1.55-1.68 (m, 3 H) 1.72-1.83 (m, 2H) 1.84-1.98 (m, 2 H) 2.13-2.29 (m, 2 H) 2.72-2.80 (m, 1 H) 2.92-3.03 (m, 1 H) 3.59-3.68 (m, 1 H) 3.73-3.81 (m, 1 H) 3.99-4.07 (m, 2 H) 4.09-4.26 (m, 5 H) 7.19-7.24 (m, 6H) 7.27-7.34 (m, 1 H) 7.71 (dd, J=8.92, 2.58 Hz, 1 H) 7.89 (d, J=2.38 Hz, 1 H); MS (DCI/NH$_3$) m/z 602 (M+H)$^+$.

Example 44B

N-[(2Z)-5-tert-butyl-3-[(2R)-tetrahydrofuran-2-ylmethyl]-1,3-thiazol-2(3H)-ylidene]-2-[(2S)-pyrrolidin-2-ylmethoxy]-5-(trifluoromethyl)benzamide In a 50 mL round-bottomed flask, a mixture of Example 44A (1.30 g, 2.160 mmol) in MeOH (10 mL) and palladium hydroxide on carbon (1.0 g) was stirred under a balloon filled with H2 for 72 hours. The reaction mixture was filtered and the filtrate concentrated. The residue was purified by Analogix® Intelliflash280™ (5102, 0-10% (7 M ammonia in methanol) in CH$_2$Cl$_2$ over 25 min) to obtain the title compound (0.76 g, 1.486 mmol, 68.8% yield). $^1$H NMR (300 MHz, DMSO-$d_6$) δ ppm 1.32 (s, 9 H) 1.45-1.62 (m, 1 H) 1.59-1.71 (m, 3 H) 1.76-1.86 (m, 3 H) 1.86-1.96 (m, 1 H) 2.74-2.89 (m, 2 H) 3.36-3.46 (m, 1 H) 3.61-3.69 (m, 1 H) 3.74-3.82 (m, 1 H) 3.97 (d, J=6.10 Hz, 2 H) 4.19-4.31 (m, 3 H) 7.26 (s, 1 H) 7.28 (d, J=8.82 Hz, 1 H) 7.73 (dd, J=8.48, 2.03 Hz, 1 H) 7.98 (d, J=2.37 Hz, 1 H); MS (DCI/NH$_3$) m/z 512 (M+H)$^+$. Anal. calcd $C_{25}H_{32}F_3N_3O_3S$.0.26 CH$_2$Cl$_2$: C, 56.85; H, 6.14; N, 7.87; Found: C, 57.08; H, 5.74; N, 7.89.

Example 45

N-[(2Z)-5-tert-butyl-3-[(2R)-tetrahydrofuran-2-ylmethyl]-1,3-thiazol-2(3H)-ylidene]-2-{[(2S)-1-ethylpyrrolidin-2-yl]methoxy}-5-(trifluoromethyl)benzamide To a solution of Example 44B (100 mg, 0.195 mmol) in CH$_2$Cl$_2$ (3 ml) was added acetaldehyde (25.8 mg, 0.586 mmol), acetic acid (11.74 mg, 0.195 mmol) and sodium triacetoxyhydroborate (124 mg, 0.586 mmol) and the mixture was stirred for 2 hours. Saturated NaHCO$_3$ solution was added and the mixture was extracted with CH$_2$Cl$_2$ (3×5 mL). The organics were combined, dried, concentrated, and the residue was purified by preparative HPLC on a Waters Symmetry C8 column (25 mm×100 mm, 7 µm particle size) using a gradient of 10-100% acetonitrile (A) and 10 mM ammonium acetate in water (B), at a flow rate of 2.0 mL/min (0-0.1 min 10% A, 0.1-2.6 min 10-100% A, 2.6-2.9 min 100% A, 2.9-3.0 min 100-10% A. 0.5 min post-run delay) to obtain the title compound (41 mg, 39%). $^1$H NMR (300 MHz, DMSO-d$_6$) δ ppm 0.95 (t, J=7.14 Hz, 3 H) 1.32 (s, 9 H) 1.57-1.71 (m, 4 H) 1.75-1.83 (m, 2 H) 1.84-1.89 (m, 1 H) 1.90-1.95 (m, 1 H) 2.11-2.23 (m, 1 H) 2.24-2.33 (m, 1 H) 2.75-2.82 (m, 1 H) 2.89-3.05 (m, 2 H) 3.59-3.70 (m, 1 H) 3.74-3.82 (m, 1H) 3.88-3.97 (m, 1 H) 3.98-4.05 (m, 1 H) 4.17-4.22 (m, 2 H) 4.23-4.32 (m, 1 H) 7.24-7.30 (m, 2 H) 7.72 (dd, J=8.72, 2.78 Hz, 1 H) 7.91 (d, J=2.38 Hz, 1 H); MS (DCI/NH$_3$) m/z 540 (M+H)$^+$.

Example 46

N-[(2Z)-5-tert-butyl-3-[(2R)-tetrahydrofuran-2-ylmethyl]-1,3-thiazol-2(3H)-ylidene]-2-{[(2S)-1-isopropylpyrrolidin-2-yl]methoxy}-5-(trifluoromethyl) benzamide The title compound was prepared and isolated as described in Example 45, substituting acetone for acetaldehyde. $^1$H NMR (300 MHz, DMSO-d$_6$) δ ppm 0.91 (d, J=6.35 Hz, 3 H) 0.99 (d, J=6.35 Hz, 3 H) 1.32 (s, 9 H) 1.59-1.74 (m, 4 H) 1.74-1.86 (m, 2 H) 1.89-1.94 (m, 2 H) 2.76-2.83 (m, 1 H) 2.97 (dt, J=12.79, 6.49 Hz, 1 H) 3.06-3.18 (m, 2 H) 3.60-3.68 (m, 1 H) 3.73-3.82 (m, 2 H) 3.90-3.95 (m, 1 H) 4.16-4.22 (m, 2 H) 4.22-4.32 (m, 1 H) 7.23-7.29 (m, 2 H) 7.71 (dd, J=8.72, 2.78 Hz, 1 H) 7.90 (d, J=2.38 Hz, 1 H); MS (DCI/NH$_3$) m/z 554 (M+H)$^+$. Anal. calcd C$_{28}$H$_{38}$F$_3$N$_3$O$_3$S.2H2O.1 HOAc: C, 56.20; H, 7.16; N, 6.78; Found: C, 56.44; H, 6.87; N, 6.62.

Example 47

2-{[(2S)-1-acetylpyrrolidin-2-yl]methoxy}-N-[(2Z)-5-tert-but 1-3[(2R)-tetrahydrofuran-2-ylmethyl]-1,3-thiazol-2(3H)-ylidene]-5-(trifluoromethyl)benzamide To a solution of Example 44B (70 mg, 0.137 mmol) and triethylamine (0.038 ml, 0.274 mmol) in CH$_2$Cl$_2$ (3 mL) was added acetyl chloride drop-wise (16.11 mg, 0.205 mmol) and the mixture was stirred for 2 hours. Saturated NaHCO$_3$ was added and the mixture was extracted with CH$_2$Cl$_2$ (3×5 mL). The organics were combined, dried, concentrated, and the residue was purified by preparative HPLC on a Waters Symmetry C8 column (25 mm×100 mm, 7 μm particle size) using a gradient of 10-100% acetonitrile (A) and 10 mM ammonium acetate in water (B), at a flow rate of 2.0 mL/min (0-0.1 min 10% A, 0.1-2.6 min 10-100% A, 2.6-2.9 min 100% A, 2.9-3.0 min 100-10% A. 0.5 min post-run delay) to obtain the title compound in 77% yield. $^1$H NMR (300 MHz, DMSO-d$_6$) δ ppm 1.32 (s, 9 H) 1.57-1.69 (m, 1 H) 1.75-1.84 (m, 3 H) 1.84-1.93 (m, 2 H) 1.94 (s, 3 H) 1.96-2.03 (m, 2 H) 3.35-3.47 (m, 2 H) 3.60-3.69 (m, 1 H) 3.74-3.82 (m, 1 H) 3.98-4.08 (m, 1 H) 4.17-4.30 (m, 5 H) 7.26 (s, 1 H) 7.28-7.37 (m, 1 H) 7.69-7.77 (m, 1 H) 7.88-7.94 (m, 1 H); MS (DCI/NH$_3$) m/z 554 (M+H)$^+$. Anal. calcd C$_{27}$H$_{34}$F$_3$N$_3$O$_4$S.0.5H2O: C, 57.64; H, 6.27; N, 7.47; Found: C, 57.70; H, 6.27; N, 7.47.

Example 48

N-[(2Z)-5-tert-butyl-3-[(2R)-tetrahydrofuran-2-ylmethyl]-1,3-thiazol-2(3H)-ylidene]-2-{[(2S)-1-(methylsulfonyl)pyrrolidin-2-yl]methoxy}-5-(trifluoromethyl)benzamide To a solution of Example 44B (70 mg, 0.137 mmol), triethylamine (0.038 ml, 0.274 mmol) in CH$_2$Cl$_2$ (3 ml) was added dropwise methanesulfonyl chloride (23.51 mg, 0.205 mmol) and the mixture was stirred for 2 hours. Saturated NaHCO$_3$ solution was added and the mixture was extracted with CH$_2$Cl$_2$ (3×5 mL). The organics were combined, dried, concentrated, and the residue was purified by preparative HPLC on a Waters Symmetry C8 column (25 mm×100 mm, 7 μm particle size) using a gradient of 10-100% acetonitrile (A) and 10 mM ammonium acetate in water (B), at a flow rate of 2.0 mL/min (0-0.1 min 10% A, 0.1-2.6 min 10-100% A, 2.6-2.9 min 100% A, 2.9-3.0 min 100-10% A. 0.5 min post-run delay) to obtain the title compound in 77% yield. $^1$H NMR (300 MHz, DMSO-d$_6$) δ ppm 1.32 (s, 9 H) 1.57-1.69 (m, 1 H) 1.76-1.86 (m, 3 H) 1.89-2.01 (m, 4 H) 2.94 (s, 3 H) 3.25 (t, J=6.44 Hz, 2 H) 3.61-3.69 (m, 1 H) 3.74-3.82 (m, 1 H) 3.97-4.06 (m, 2 H) 4.15-4.30 (m, 4 H) 7.27 (s, 1 H) 7.29 (d, J=8.82 Hz, 1 H) 7.74 (dd, J=8.82, 2.03 Hz, 1 H) 7.95 (d, J=2.37 Hz, 1 H); MS (DCI/NH$_3$) m/z 590 (M+H)$^+$.

Example 49

N-[(2Z)-5-tert-butyl-3-[(2R)-tetrahydrofuran-2-ylmethyl]-1,3-thiazol-2(3H)-ylidene]-2-[(2R)-1-methyl-1-oxido rrolidin-2-yl]methoxy]-5-(trifluoromethyl) benzamide A solution of Example 24 (130 mg, 0.247 mmol) in anhydrous CH$_2$Cl$_2$ (5 mL) was treated with phthalic anhydride (36 mg, 0.247 mmol) and then urea-hydrogen peroxide complex (23 mg, 0.247 mmol). The reaction mixture was stirred at room temperature for 4 hours and then extracted between saturated K$_2$CO$_3$ and CH$_2$Cl$_2$. The organic layer was washed with brine, dried (MgSO$_4$) and concentrated. The residue was purified by using an Analogix® Intelliflash280™ (SiO$_2$, 0-10% MeOH in dichloromethane) to afford the title compound (120 mg, 90% yield). $^1$H NMR (300 MHz, DMSO-d$_6$) δ ppm 1.24-1.37 (m, 9H), 1.52-2.14 (m, 7 H), 3.09 (s, 3 H), 3.12-3.27 (m, 2 H), 3.44-3.72 (m, 2 H), 3.71-3.91 (m, 2 H), 4.08-4.24 (m, 3 H), 4.23-4.40 (m, 1 H), 4.81 (dd, J=10.7, 8.3 Hz, 1 H), 7.26 (s, 1H), 7.36 (d, J=8.7 Hz, 1 H), 7.76 (dd, J=8.7, 2.4 Hz, 1 H), 7.98 (d, J=2.4 Hz, 1 H). MS (APCI/NH$_3$) m/z 542 (M+H)$^+$. Anal. calcd for C$_{26}$H$_{34}$F$_3$N$_3$O$_4$S: C, 57.66; H, 6.33; N, 7.76. Found: 55.13; H, 6.64; N, 7.23

Example 50

N-[(2Z)-5-tert-butyl-3-[(2R)-tetrahydrofuran-2-ylmethyl]-1,3-thiazol-2(3H)-ylidene]-2-(3-hydroxy-3-methylbutoxy)-5-(trifluoromethyl)benzamide The title compound was prepared as described in Example 1B substituting 3-methylbutane-1,3-diol for (R)-tert-butyl 2-(hydroxymethyl)azetidine-1-carboxylate. $^1$H NMR (300 MHz, DMSO-d$_6$) δ ppm 1.15 (s, 6 H) 1.32 (s, 9 H) 1.53-1.72 (m, 1 H) 1.74-1.99 (m, 5H) 3.58-3.72 (m, 1 H) 3.74-3.85 (m, 1 H) 4.11-4.37 (m, 5 H) 4.47 (s, 1 H) 7.24-7.35 (m, 2 H) 7.75 (dd, J=8.72, 2.38 Hz, 1 H) 8.01 (d, J=2.38 Hz, 1 H);); MS (DCI/NH$_3$) m/z 515 [M+H]$^+$.

Example 51

N-[(2Z)-5-tert-butyl-3-[(2R)-tetrahydrofuran-2-ylmethyl]-1,3-thiazol-2(3H)-ylidene]-2-{[(2S)-1-methylpyrrolidin-2-yl]methoxy}-5-(trifluoromethyl)benzenecarbothioamide To a solution of Example 24 (300 mg, 0.571 mmol) in toluene (6 mL) at ambient temperature was added Lawesson's Reagent (231 mg, 0.571 mmol). This mixture was warmed to 95° C. and allowed to stir for 4 hours. The mixture was then cooled to ambient temperature, concentrated under reduced pressure. The residue was dissolved in EtOAc (20 mL) and washed with NaHCO₃ solution. The organics were combined, dried, concentrated, and the residue was purified by Analogix® Intelliflash280™ (SiO₂, 0-10% (7 M ammonia in methanol) in CH₂Cl₂ over 25 min) to obtain the title compound in 87% yield. $^1$H NMR (300 MHz, DMSO-d₆) δ ppm 1.37 (s, 9 H) 1.47-1.63 (m, 4 H) 1.73-1.89 (m, 4 H) 2.10 (q, J=8.59 Hz, 1 H) 2.19 (s, 3 H) 2.38-2.47 (m, 1 H) 2.81-2.90 (m, 1 H) 3.59-3.67 (m, 1 H) 3.71-3.81 (m, 1 H) 3.96 (ddd, J=14.67, 9.41, 5.76 Hz, 2 H) 4.27-4.34 (m, 3 H) 7.23 (d, J=8.82 Hz, 1 H) 7.55-7.59 (m, 2 H) 7.63 (dd, J=8.82, 2.03 Hz, 1 H); MS (DCI/NH₃) m/z 542 (M+H)⁺.

Example 52

N-[(2Z)-3-(2-methoxyethyl)-5-methyl-1,3-thiazol-2 (3H)-ylidene]-2- {[(2S)-1-methylpyrrolidin-2-yl] methoxy}-5-(trifluoromethyl)benzamide Example 52A N-[(2Z)-3-(2-methoxyethyl)-5-methyl-1,3-thiazol-2 (3H)-ylidene]-2-fluoro-5-(trifluoromethyl)benzamide The title compound was prepared as described in Example 1A substituting 3-(2-methoxyethyl)-5-methylthiazol-2(3H)-imine hydrobromide (prepared as described in WO 2009067613) for Example 22A. MS (DCI/NH₃) m/z 363 (M+H)⁺.

Example 52B

N-[(2Z)-3-(2-methoxyethyl)-5-methyl-1,3-thiazol-2 (3H)-ylidene]-2-{[(2S)-1-methylpyrrolidin-2-yl] methoxy}-5-(trifluoromethyl)benzamide The title compound was prepared as described in Example 22C (example 24 refers to example 22C), substituting Example 22B with Example 52A and substituting (R)-(tetrahydrofuran-2-yl)methanol with (S)-(1-methylpyrrolidin-2-yl)methanol. $^1$H NMR (300 MHz, DMSO-d₆) δ ppm 1.49-1.75 (m, 3 H), 1.84-1.99 (m, 1 H), 2.10-2.24 (m, 1 H), 2.28 (s, 3 H), 2.33 (s, 3 H), 2.54-2.68 (m, 1 H), 2.83-3.03 (m, 1 H), 3.26 (s, 3 H), 3.68 (t, J=5.2 Hz, 2 H), 3.91-4.11 (m, 2 H), 4.32 (t, J=5.4 Hz, 2 H), 7.20-7.36 (m, 2 H), 7.73 (dd, J=8.5, 2.6 Hz, 1 H), 7.92 (d, J=2.4 Hz, 1 H). MS (APCI/NH₃) m/z 458 (M+H)⁺. Anal. calcd for C₂₁H₂₆F₃N₃O₃S: C, 54.28; H, 5.81; N, 9.04. Found: C, 53.96; H, 5.62; N, 8.90.

Example 53

N-[(2Z)-5-tert-butyl-3-[(2R)-tetrahydrofuran-2-ylmethyl]-1,3-thiazol-2(3H)-ylidene]-2-{[(2S,4S)-4-fluoro-1-methylpyrrolidin-2-yl]methoxy}-5-(trifluoromethyl)benzamide Example 53A (2S,4S)-tert-butyl 4-fluoro-2-(hydroxymethyl)pyrrolidine-1-carboxylate A solution of (2S,4S)-1-(tert-butoxycarbonyl)-4-fluoropyrrolidine-2-carboxylic acid (500 mg, 2.14 mmol) in THF (15 mL) was treated with a 1N solution of BH₃-THF complex (4.29 mL, 4.29 mmol). The mixture was stirred at ambient temperature for 12 hours then quenched with MeOH and concentrated under reduced pressure. The residue was purified by column chromatography using an Analogix® Intelliflash280™ (SiO₂, 0-100% ethyl acetate in hexanes) to afford the title compound (425 mg, 90%). MS (DCI/NH₃) m/z 220 (M+H)⁺.

Example 53B tert-butyl (2S,4S)-2-{[2-({[(2Z)-5-tert-butyl-3-[(2R)-tetrahydrofuran-2-ylmethyl]-1,3-thiazol-2(3H)-ylidene]amino}carbonyl)-4-(trifluoromethyl)phenoxy]methyl}-4-fluoropyrrolidine-1-carboxylate The title compound was prepared as described in Example 1B substituting Example 53A for (R)-tert-butyl 2-(hydroxymethyl)azetidine-1-carboxylate. MS (DCI/NH₃) m/z 630 (M+H)⁺.

Example 53C

N-[(2Z)-5-tert-butyl-3-[(2R)-tetrahydrofuran-2-ylmethyl]-1,3-thiazol-2(3H)-ylidene]-2-{[(2S,4S)-4-fluoropyrrolidin-2-yl]methoxy}-5-(trifluoromethyl) benzamide The title compound was prepared using the procedure as described in Example 1C substituting Example 53B for Example 1B. MS (DCI/NH₃) m/z 530 (M+H)⁺.

Example 53D

N-[(2Z)-5-tert-butyl-3-[(2R)-tetrahydrofuran-2-ylmethyl]-1,3-thiazol-2(3H)-ylidene]-2-{[(2S,4S)-4-fluoro-1-methylpyrrolidin-2-yl]methoxy}-5-(trifluoromethyl)benzamide The title compound was prepared as described in Example 3, substituting Example 53C for Example 2B. $^1$H NMR (400 MHz, CDCl₃) δ ppm 1.37 (s, 9 H) 1.62-1.71 (m, 1 H) 1.75-1.93 (m, 3 H) 1.98-2.11 (m, 1 H) 2.34-2.57 (m, 2 H) 2.49 (s, 3 H) 2.78-2.98 (m, 1H) 3.23-3.41 (m, 1 H) 3.69-3.93 (m, 2 H) 4.02 (dd, J=9.05, 6.90 Hz, 1 H) 4.12-4.20 (m, 1H) 4.21-4.33 (m, 2 H) 4.41 (dd, J=13.66, 2.92 Hz, 1 H) 4.92-5.32 (m, 1 H) 6.86 (s, 1 H) 7.03 (d, J=8.90 Hz, 1 H) 7.59 (dd, J=8.59, 1.84 Hz, 1 H) 8.14 (d, J=2.45 Hz, 1 H); MS (DCI/NH₃) m/z 544 (M+H)⁺.

Example 54

N-[(2Z)-5-tert-butyl-3-[(2R)-tetrahydrofuran-2-ylmethyl]-1,3-thiazol-2(3H)-ylidene]-2-{[(2S,4R)-4-fluoro-1-methylpyrrolidin-2-yl]methoxy}-5-(trifluoromethyl)benzamide Example 54A (2S,4R)-tert-butyl 4-fluoro-2-(hydroxymethyl)pyrrolidine-1-carboxylate The title compound was prepared as described in Example 53A substituting (2S,4R)-1-(tert-butoxycarbonyl)-4-fluoropyrrolidine-2-carboxylic acid for (2S,4S)-1-(tert-butoxycarbonyl)-4-fluoropyrrolidine-2-carboxylic acid. MS (DCI/NH₃) m/z 220 (M+H)⁺.

Example 54B tert-but (2S,4R)-2-{[2-({[(2Z)-5-tert-butyl 3-[(2R)-tetrahydrofuran-2-ylmethyl]-1,3-thiazol-2(3H)-ylidene]amino}carbonyl)-4-(trifluoromethyl)phenoxy]methyl}-4-fluoropyrrolidine-1-carboxylate The title compound was prepared as described in Example 1B substituting Example 54A for (R)-tert-butyl 2-(hydroxymethyl)azetidine-1-carboxylate. MS (DCI/NH$_3$) m/z 630 (M+H)$^+$.

Example 54C

N-[(2Z)-5-tert-butyl-3-[(2R)-tetrahydrofuran-2-ylmethyl]-1,3-thiazol-2(3H)-ylidene]-2-{[(2S,4R)-4-fluoropyrrolidin-2-yl]methoxy}-5-(trifluoromethyl)benzamide The title compound was prepared as described in Example 1C, substituting Example 54B for Example 1B. MS (DCI/NH$_3$) m/z 530 (M+H)$^+$.

Example 54D

N-[(2Z)-5-tert-butyl-3-[(2R)-tetrahydrofuran-2-ylmethyl]-1,3-thiazol-2(3H)-ylidene]-2-{[(2S,4R)-4-fluoro-1-methylpyrrolidin-2-yl]methoxy}-5-(trifluoromethyl)benzamide The title compound was prepared as described in Example 3, substituting Example 54C for Example 2B. $^1$H NMR (400 MHz, CDCl$_3$) δ ppm 1.36 (s, 9 H) 1.61-1.72 (m, 1 H) 1.74-1.98 (m, 3 H) 1.99-2.10 (m, 1 H) 2.27-2.42 (m, 1 H) 2.50 (s, 3 H) 2.56-2.76 (m, 1H) 3.17 (dd, J=9.36, 5.98 Hz, 1 H) 3.42-3.59 (m, 1 H) 3.72-3.91 (m, 2 H) 3.99-4.07 (m, 1H) 4.08-4.21 (m, 2 H) 4.21-4.32 (m, 1 H) 4.42 (dd, J=13.66, 2.92 Hz, 1 H) 5.04-5.35 (m, 1 H) 6.87 (s, 1 H) 7.01 (d, J=8.59 Hz, 1 H) 7.58 (dd, J=8.59, 2.15 Hz, 1 H) 8.13 (d, J=2.15 Hz, 1 H); MS (DCI/NH$_3$) m/z 544 (M+H)$^+$.

Example 55

N-[(2Z)-5-tert-butyl-3-[(2R)-tetrahydrofuran-2-ylmethyl]-1,3-thiazol-2(3H)-ylidene]-2-({[(2S)-1-methylpyrrolidin-2-yl]methyl}amino)-5-(trifluoromethyl)benzamide

Example 55A tert-butyl (2S)-2-({[2-{[(2Z)-5-tert-butyl-3-[(2R)-tetrahydrofuran-2-ylmethyl]-1,3-thiazol-2(3H)-ylidene]amino}carbonyl)-4-(trifluoromethyl)phenyl]amino}methyl)pyrrolidine-1-carboxylate The product of Example 1A (450 mg, 1.05 mmol), (S)-tert-butyl 2-(aminomethyl)pyrrolidine-1-carboxylate (1 g, 5.0 mmol) and triethylamine (730 μL, 5.23 mmol) in tetrahydrofuran (1 mL) was heated at 120° C. in a microwave for 60 minutes. The mixture was diluted with water, and extracted with EtOAc. The organic extract was dried (Na$_2$SO$_4$), filtered and concentrated. Purification by flash chromatography (silica gel, EtOAc/hexane in 0-50% gradient) afforded 534 mg (84%) of the title compound. MS (ESI) m/z 610 (M+H)$^+$.

Example 55B (Z)—N-(5-tert-butyl-3-4(R)-tetrahydrofuran-2-yl)methyl)thiazol-2(3H)-ylidene)-2-((S)-pyrrolidin-2-ylmethylamino)-5-(trifluoromethyl)benzamide The title compound was prepared using the procedure as described in Example 1C substituting Example 55A for Example 1B. MS (DCI/NH$_3$) m/z 510 (M+H)$^+$.

Example 55C

N-[(2Z)-5-tert-butyl-3-[(2R)-tetrahydrofuran-2-ylmethyl]-1,3-thiazol-2(3H)-ylidene]-2-({[(2S)-1-methylpyrrolidin-2-yl]methyl}amino)-5-(trifluoromethyl)benzamide The title compound was prepared as described in Example 3 substituting Example 55B for Example 2B. $^1$H NMR (400 MHz, CDCl$_3$) δ ppm 1.36 (s, 9 H) 1.65-1.80 (m, 3 H) 1.78-1.94 (m, 3 H) 1.99-2.13 (m, 2 H) 2.27 (d, J=7.67 Hz, 1 H) 2.45 (s, 3 H) 2.50-2.62 (m, 1 H) 3.06-3.24 (m, 2 H) 3.46 (s, 1 H) 3.71-3.91 (m, 2 H) 4.19-4.36 (m, 2 H) 4.35-4.47 (m, 1 H) 6.72 (d, J=8.90 Hz, 1 H) 6.82 (s, 1 H) 7.47 (dd, J=8.75, 1.99 Hz, 1 H) 8.63 (s, 1H) 9.10 (s, 1 H); MS (DCI/NH$_3$) m/z 525 (M+H)$^+$.

Example 56

N-[(2Z)-5-tert-butyl-3-[(2R)-tetrahydrofuran-2-ylmethyl]-1,3-thiazol-2(3H)-ylidene]-2-(1H-pyrazol-5-ylmethoxy)-5-(trifluoromethyl)benzamide The title compound was prepared as described in Example 2A substituting (5)-tert-butyl 2-(hydroxymethyl)azetidine-1-carboxylate with (1H-pyrazol-5-yl)methanol. $^1$H NMR (300 MHz, DMSO-d$_6$) δ ppm 1.19-1.39 (m, 9 H), 1.38-1.59 (m, 1 H), 1.65-1.92 (m, 3 H), 3.52-3.82 (m, 2 H), 3.85-4.05 (m, 3 H), 4.42 (d, J=5.6 Hz, 2 H), 5.05-5.22 (m, 1 H), 6.40 (d, J=2.4 Hz, 1 H), 7.13-7.33 (m, 1 H), 7.73-7.87 (m, 2 H), 7.87-7.99 (m, 1 H), 8.03 (d, J=2.0 Hz, 1 H). MS (DCI/NH$_3$) m/z 509 (M+H)$^+$. Anal. calcd for C$_{24}$H$_{27}$F$_3$N$_4$O$_3$S: C, 56.68; H, 5.35; N, 11.02. Found: C, 56.68; H, 5.62; N, 10.68.

Example 57

N-[(2Z)-4-tert-butyl-3-[(2R)-tetrahydrofuran-2-ylmethyl]-1,3-thiazol-2(3H)-ylidene]-2-{[(2S)-1-methylpyrrolidin-2-yl]methoxy}-5-(trifluoromethyl)benzamide

Example 57A (R)-4-tert-butyl-3-((tetrahydrofuran-2-yl)methyl)thiazol-2(3H)-imine Commercially available 3,3-dimethylbutan-2-one (Aldrich) and (R)-(tetrahydrofuran-2-yl)methanamine (Aldrich)

were processed as described in Example 22A to afford the title compound. MS (ESI+) m/z 241 (M+H)+.

Example 57B (S)-2-((1-methylpyrrolidin-2-yl)methoxy)-5-(trifluoromethyl)benzonitrile To a solution of 2-fluoro-5-(trifluoromethyl)benzonitrile (8.0 g, 42.3 mmol, Aldrich) in tetrahydrofuran (50 mL) were added sodium hydride (1.9 g, 46.5 mmol) and (S)-(1-methylpyrrolidin-2-yl)methanol (5.5 mL, 46.5 mmol, Aldrich). After stirring at room temperature for 3 hours, the reaction mixture was quenched with saturated NaHCO$_3$ (30 mL). The aqueous layer was extracted with ethyl acetate (3×30 mL). The combined organic layers were washed with brine (50 mL), dried Na$_2$SO$_4$, filtered and concentrated under reduced pressure to afford 12.0 g (100%) of the title compound. LCMS (APCI+) m/z 285 (M+H)+.

Example 57C (S)-2-((1-methylpyrrolidin-2-yl)methoxy)-5-(trifluoromethyl)benzoic acid To a solution of Example 57B (12.0 g, 42 mmol) in ethanol (50 mL) was added 15 mL of water and then warmed to 40° C. Then sodium hydroxide (7.8 mL, 148 mmol) was added followed by hydrogen peroxide (7.3 mL, 127 mmol) in four portions, each one hour apart. The reaction mixture was heated at 40° C. for 4 additional hours. Sodium hydroxide (6.7 mL, 127 mmol) was added followed by 10 mL of water. After stirring at 80° C. for 12 hours, the reaction mixture was cooled, concentrated under reduced pressure, diluted with 100 mL of water, and extracted with diethyl ether (2×25 mL). The aqueous solution was neutralized to pH 7 with 6N aqueous HCl and concentrated under reduced pressure to dryness. The residue was suspended in dichloromethane (100 mL), the solution heated to 60° C. and filtered; this process was repeated 3 times. The combined filtrates were concentrated under reduced pressure and azeotroped with toluene to afford 10.2 g (80%) of the title compound. MS (ESI+) m/z 304 (M+H)+.

Example 57D

N-[(2Z)-4-tert-butyl-3-[(2R)-tetrahydrofuran-2-ylmethyl]-1,3-thiazol-2(3H)-ylidene]-2-{[(2S)-1-methylpyrrolidin-2-yl]methoxy}-5-(trifluoromethyl)benzamide To a solution of Example 57A (0.17 g, 0.7 mmol) in tetrahydrofuran (10 mL) were added Example 57C (0.21 g, 0.7 mmol), 1-hydroxy-benzotriazole hydrate (0.11 g, 0.7 mmol), N-(3-dimethylaminopropyl)-N'-ethylcarbodiimide hydrochloride (0.13 g, 0.7 mmol) and triethylamine (0.3 mL, 2.1 mmol). The reaction mixture was stirred at 80° C. for 2 hours and then quenched with saturated NaHCO$_3$ (10 mL). The aqueous layer was extracted with EtOAc (3×20 mL). The combined organic extracts were dried over anhydrous Na$_2$SO$_4$, filtered and concentrated. The residue was purified by column chromatography using an Analogix® Intelliflash 280™ (SiO$_2$, 5-100% of TEA/MeOH/EtOAc (0.1/1/10) in hexanes) to obtain the title compound. $^1$H NMR (300 MHz, DMSO-d$_6$) δ ppm 1.40 (s, 9 H), 1.55-1.72 (m, 3 H), 1.71-2.06 (m, 5 H), 2.10-2.23 (m, 1 H), 2.32 (s, 3 H), 2.54-2.66 (m, 1 H), 2.83-3.00 (m, 1 H), 3.49-3.64 (m, 1 H), 3.65-3.80 (m, 1 H), 3.90-4.09 (m, 2 H), 4.25-4.51 (m, 2 H), 4.51-4.69 (m, 1 H), 6.70 (s, 1 H), 7.29 (d, J=8.5 Hz, 1 H), 7.73 (dd, J=8.8, 2.7 Hz, 1H), 8.01 (d, J=2.0 Hz, 1 H); MS (ESI+) m/z 526 (M+H)+.

Example 58

N-[(2Z)-5-tert-butyl-3-[(2R)-tetrahydrofuran-2-ylmethyl]-1,3-thiazol-2(3H)-ylidene]-2-{2-[(2-hydroxyethyl)amino]ethoxy}-5-(trifluoromethyl)benzamide The title compound was prepared as described in Example 1B substituting 2-(oxazolidin-3-yl)ethanol for (R)-tert-butyl 2-(hydroxymethyl)azetidine-1-carboxylate. $^1$H NMR (300 MHz, DMSO-d$_6$) δ ppm 1.32 (s, 9 H), 1.57-1.72 (m, 1 H), 1.75-2.00 (m, 3 H), 2.64 (t, J=5.75 Hz, 2 H), 2.91 (t, J=5.75 Hz, 2 H), 3.44 (q, J=5.95 Hz, 2 H), 3.60-3.71 (m, 1H), 3.74-3.83 (m, 1 H), 4.13-4.35 (m, 6 H), 4.43 (t, J=5.35 Hz, 1 H), 7.27 (s, 1 H), 7.30 (d, J=8.73 Hz, 1 H), 7.75 (dd, J=8.72, 2.38 Hz, 1 H), 8.01 (d, J=2.38 Hz, 1 H); MS (DCI/NH$_3$) m/z 516 [M+H]+.

Example 59

N-[(2Z)-5-tert-butyl-3-[(2R)-tetrahydrofuran-2-ylmethyl]-1,3-thiazol-2(3H)-ylidene]-5-cyano-2-{[(2S)-1-methylpyrrolidin-2-yl]methoxy}benzamide

Example 59A methyl 5-cyano-2-fluorobenzoate

To a solution of 3-bromo-4-fluorobenzonitrile (20 g, 100 mmol) in MeOH (150 mL) was added to PdCl$_2$(dppf) (Heraeus) (0.732 g, 1.000 mmol) and triethylamine (27.9 mL, 200 mmol) in a 250 mL suresealed pressure bottle. The mixture was pressurized with carbon monoxide (60 psi), and stirred for 4 hours at 100° C. The mixture was cooled, concentrated, diluted with EtOAc and filtered. The filtrate was concentrated and purified by Analogix® Intelliflash280™ (SiO$_2$, 0-100% EtOAc in hexane over 25 minutes) to obtain the title compound (9.85 g, 55%). $^1$H NMR (300 MHz, DMSO-d$_6$) δ ppm 3.89 (s, 3 H) 7.62 (dd, J=10.68, 8.65 Hz, 1 H) 8.20 (ddd, J=8.73, 4.49, 2.37 Hz, 1 H) 8.35 (dd, J=6.61, 2.20 Hz, 1H); MS (DCI/NH$_3$) m/z 197 (M+NH$_4$)+.

Example 59B 5-cyano-2-fluorobenzoic acid

To a solution of Example 59A (535 mg, 2.99 mmol) in MeOH (4 ml) was added a solution of NaOH (576 mg, 14.40 mmol) in H$_2$O (4 mL) and the mixture was stirred for 2 hours then concentrated under reduced pressure. The residue was acidified with HCl (12 N) to pH 1, and extracted with EtOAc. The organic layers were combined, dried and concentrated to yield a white solid and carried on without further purification. MS (DCI/NH$_3$) m/z 183(M+NH$_4$)+.

Example 59C

N-[(2Z)-5-tert-butyl-3-[(2R)-tetrahydrofuran-2-ylmethyl]-1,3-thiazol-2(3H)-ylidene]-5-cyano-2-fluorobenzamide A solution of Example 59B (535 mg, 3.24 mmol) in thionyl chloride (3855 mg, 32.4 mmol) was heated at 90° C. for 2 hours. The solution was cooled, concentrated, diluted with toluene, and concentrated to afford 2-fluoro-5-cyanobenzoyl chloride which was used without purification. The title compound was prepared and isolated as described in Example 22B, substituting 2-fluoro-5-cyanobenzoyl chloride for 2-fluoro-5-(trifluoromethyl)benzoyl chloride, in 61% yield. $^1$H NMR (300 MHz, DMSO-$d_6$) δ ppm 1.33 (s, 9 H) 1.58-1.72 (m, 1H) 1.82 (qd, J=7.01, 6.74 Hz, 2 H) 1.90-1.97 (m, 1 H) 3.61-3.70 (m, 1 H) 3.74-3.83 (m, 1H) 4.24-4.35 (m, 3 H) 7.33 (s, 1 H) 7.52 (dd, J=10.71, 8.72 Hz, 1 H) 8.02-8.07 (m, 1 H) 8.40 (dd, J=6.94, 2.18 Hz, 1 H); MS (DCI/NH$_3$) m/z 388 (M+H)$^+$.

Example 59D

N-[(2Z)-5-tert-butyl-3-[(2R)-tetrahydrofuran-2-ylmethyl]-1,3-thiazol-2(3H)-ylidene]-5-cyano-2-{[(2S)-1-methylpyrrolidin-2-yl]methoxy}benzamide The title compound was prepared and isolated as described in Example 22C, substituting Example 59C for Example 22B and substituting (S)-(1-methylpyrrolidin-2-yl)methanol for (R)-(tetrahydrofuran-2-yl)methanol. $^1$H NMR (300 MHz, DMSO-$d_6$) δ ppm 1.32 (s, 9 H) 1.54-1.68 (m, 4 H) 1.75-1.85 (m, 2 H) 1.86-1.98 (m, 2 H) 2.16 (q, J=8.59 Hz, 1 H) 2.31 (s, 3 H) 2.56-2.60 (m, 1 H) 2.87-2.96 (m, 1 H) 3.61-3.69 (m, 1 H) 3.74-3.82 (m, 1 H) 3.95-4.09 (m, 2 H) 4.18-4.30 (m, 3 H) 7.23-7.29 (m, 2 H) 7.84 (dd, J=8.72, 2.38 Hz, 1 H) 7.98 (d, J=2.38 Hz, 1 H); MS (DCI/NH$_3$) m/z 483 (M+H)$^+$. Anal. calcd C$_{26}$H$_{34}$N$_4$O$_3$S: C, 64.7; H, 7.1; N, 11.61. Found: C, 64.33; H, 7.34; N, 11.50.

Example 60

N-[(2Z)-4,5-dimethyl-3-[(2R)-tetrahydrofuran-2-ylmethyl]-1,3-thiazol-2(3H)-ylidene]-2-{[(2S)-1-methylpyrrolidin-2-yl]methoxy}-5-(trifluoromethyl)benzamide

Example 60A (R)-(tetrahydrofuran-2-yl)methyl 4-methylbenzenesulfonate

The title compound was prepared from commercially available (R)-(tetrahydrofuran-2-yl)methanol (Fluka) according to the procedure as described in Agricultural and Biological Chemistry (1991), 55(6), 1685-6. MS (ESI$^+$) m/z 257(M+H)$^+$.

Example 60B

N-[(2Z)-4,5-dimethyl-3-[(2R)-tetrahydrofuran-2-ylmethyl]-1,3-thiazol-2(3H)-ylidene]-2-{[(2S)-1-methylpyrrolidin-2-yl]methoxy}-5-(trifluoromethyl)benzamide A mixture of 4,5-dimethylthiazol-2-amine (0.5 g, 3.9 mmol, Oakwood), Example 60A, and tetraethylammonium iodide (0.5 g, 1.9 mmol) in N,N,N-dimethylformamide (1 mL) was heated at 95° C. for 16 hours. The reaction mixture was cooled to room temperature and quenched with 1 M NaHCO$_3$ (10 mL). The aqueous layer was extracted with dichloromethane (3×20 mL). The combined organic extracts were dried over anhydrous Na$_2$SO$_4$, filtered and concentrated to obtain (R)-4,5-dimethyl-3-((tetrahydrofuran-2-yl)methyl)thiazol-2(3H)-imine, which was used without purification.

To a solution of (R)-4,5-dimethyl-3-((tetrahydrofuran-2-yl)methyl)thiazol-2(3H)-imine (5.0 g, 2.0 mmol) in tetrahydrofuran (10 mL) were added Example 57C (0.6 g, 2.0 mmol),1-hydroxy-benzotriazole hydrate (0.3 g, 2.0 mmol), N-(3-dimethylaminopropyl)-N'-ethylcarbodiimide hydrochloride (0.4 g, 2.0 mmol) and triethylamine (0.8 mL, 6.0 mmol). The reaction mixture was stirred at 80° C. for 2 hours and then quenched with saturated NaHCO$_3$ (10 mL). The aqueous layer was extracted with EtOAc (3×20 mL). The combined organic extracts were dried over anhydrous Na$_2$SO$_4$, filtered and concentrated. The residue was purified by column chromatography using an Analogix® Intelliflash 280™ (SiO$_2$, 5-100% of TEA/MeOH/EtOAc (0.1/1/10) in hexanes) to obtain the title compound. $^1$H NMR (400 MHz, DMSO-$d_6$) δ ppm 1.69-1.89 (m, 4 H), 2.15 (s, 4 H), 2.28-2.37 (m, 1 H), 2.38 (s, 3 H), 2.43 (s, 3 H), 2.49 (s, 3 H), 2.71-2.81 (m, 1 H), 3.04-3.13 (m, 1 H), 3.75-3.83 (m, 1H), 3.91-4.00 (m, 1 H), 4.11-4.29 (m, 3 H), 4.41-4.54 (m, 2 H), 7.44 (d, J=8.6 Hz, 1 H), 7.88 (dd, J=8.9, 2.5 Hz, 1 H), 8.13 (d, J=2.5 Hz, 1 H); MS (ESI$^+$) m/z 498 (M+H)$^+$

Example 61

N-[(2Z)-5-tert-butyl-4-methyl-3-[(2R)-tetrahydrofuran-2-ylmethyl]-1,3-thiazol-2(3H)-ylidene]-2-{[(2S)-1-methylpyrrolidin-2-yl]methoxy}-5-(trifluoromethyl)benzamide The title compound was prepared as described in Example 60 substituting 5-tert-butyl-4-methylthiazol-2-amine for 4,5-dimethylthiazol-2-amine. $^1$H NMR (400 MHz, DMSO-$d_6$) δ ppm 1.39 (s, 9 H), 1.53-1.72 (m, 4 H), 1.74-1.99 (m, 4 H), 2.18 (q, J=8.7 Hz, 1 H), 2.33 (s, 3 H), 2.42 (s, 3 H), 2.55-2.65 (m, 1 H), 2.88-2.97 (m, 1 H), 3.59-3.67 (m, 1H), 3.74-3.84 (m, 1 H), 3.94-4.01 (m, 1 H), 4.03-4.16 (m, 2 H), 4.22-4.31 (m, 1 H), 4.31-4.39 (m, 1 H), 7.28 (d, J=8.9 Hz, 1 H), 7.71 (dd, J=8.6, 2.5 Hz, 1 H), 7.95 (d, J=2.5 Hz, 1H); MS (ESI$^+$) m/z 540 (M+H)$^+$.

Example 62

N-[(2Z)-5-tert-butyl-3-[(2R)-tetrahydrofuran-2-ylmethyl]-1,3-thiazol-2(3H)-ylidene]-2-[(3S)-morpholin-3-ylmethoxy]-5-(trifluoromethyl)benzamide

Example 62A (S)-tert-butyl 3-(hydroxymethyl)morpholine-4-carboxylate

The title compound was prepared as described in Example 32A substituting (S)-4-(tert-butoxycarbonyl)morpholine-3-carboxylic acid for 4-benzylmorpholine-2-carboxylic acid. MS (DCI/NH$_3$) m/z 218 (M+H)$^+$.

Example 62B tert-butyl (3S)-3-{[2-({[2Z)-5-tert-butyl-3-[(2R)-tetrahydrofuran-2-ylmethyl]-1,3-thiazol-2(3H)-ylidene]amino}carbonyl)-4-(trifluoromethyl)phenoxy]methyl}morpholine-4-carboxylate To a solution of Example 1A (170 mg, 0.4 mmol) and Example 62A (94 mg, 0.43 mmol) in anhydrous THF (10 mL) at room temperature was added 1N potassium tert-butoxide (0.44 mL, 0.44 mmol) and the mixture was stirred at ambient temperature for 1 hour. The reaction mixture was acidified to pH 6 with the addition of acetic acid and concentrated under reduced pressure. The residue was dissolved in EtOAc, washed with water, saturated solution of sodium bicarbonate, brine, dried with MgSO$_4$, filtered, and concentrated Purification of the residue by chromatography (SiO$_2$, eluted with EtOAc-MeOH: 9:1) afforded 140 mg of the title compound. MS (DCI/NH$_3$) m/z 628 (M+H)$^+$.

Example 62C

N-[(2Z)-5-tert-butyl-3-[(2R)-tetrahydrofuran-2-ylmethyl]-1,3-thiazol-2(3H)-ylidene]-2-[(3S)-morpholin-3-ylmethoxy]-5-(trifluoromethyl)benzamide Example 62B (140 mg, 0.22 mmol) in anhydrous CH$_2$Cl$_2$ (10 mL) was treated with trifluoroacetic acid (0.09 mL, 1.12 mmol) for 2 hours at room temperature. The mixture was concentrated under reduced pressure. The residue was diluted with saturated solution of NaHCO$_3$ and extracted with EtOAc. The organic extract was washed with brine, dried with MgSO$_4$, filtered, and concentrated under reduced pressure. The residue was purified by chromatography (SiO$_2$, eluted with CH$_2$Cl$_2$-MeOH: 9:1) to afford 115 mg of the title compound. $^1$H NMR (300 MHz, DMSO-d$_6$) δ ppm 1.33 (s, 9 H), 1.57-1.70 (m, 1 H), 1.72-2.00 (m, 3 H), 2.69-2.88 (m, 2 H), 3.04-3.16 (m, 1 H), 3.21-3.45 (m, 3 H), 3.58-3.71 (m, 2 H), 3.74-3.90 (m, 2 H), 4.01 (dd, J=6.1, 2.2 Hz, 2 H), 4.17-4.34 (m, 3 H), 7.25-7.33 (m, 2 H), 7.76 (dd, J=8.9, 2.2 Hz, 1 H), 8.04 (d, J=2.4 Hz, 1 H). MS (DCI/NH$_3$) m/z 528 (M+H)$^+$. Anal. calculated for C$_{25}$H$_{32}$F$_3$N$_3$O$_4$S: C, 56.91 H, 6.11 N, 7.96. Found: C, 56.95 H, 6.11 N, 7.95.

Example 63

N-[(2Z)-5-tert-butyl-3-[(2R)-tetrahydro furan-2-ylmethyl]-1,3-thiazol-2(3H)-ylidene]-2-({2-[(tetrahydro-2H-pyran-2-yloxy)imino]propyl}oxy)-5-(trifluoromethyl)benzamide

Example 63A 1-hydroxypropan-2-one O-tetrahydro-2H-pyran-2-yl oxime

A mixture of 1-hydroxypropan-2-one (1 g, 13.5 mmol) and O-(tetrahydro-2H-pyran-2-yl)hydroxylamine (1.9 g, 16.2 mmol) in methanol (20 mL) and pyridine (7 mL) was treated with acetic acid (0.23 mL, 4 mmol) and stirred at room temperature for 12 hours. The mixture was then concentrated under reduced pressure. The residue was diluted with saturated sodium bicarbonate and extracted with ethyl acetate. The organic extract was concentrated and purified by chromatography (SiO$_2$, eluted with EtOAc-hexane-2:1) to afford 1.8 g of the title compound. MS (DCI/NH$_3$) m/z 174 (M+H)$^+$.

Example 63B

N-[(2Z)-5-tert-butyl-3-[(2R)-tetrahydrofuran-2-ylmethyl]-1,3-thiazol-2(3H)-ylidene]-2-({2-[(tetrahydro-2H-pyran-2-yloxy)imino]propyl}oxy)-5-(trifluoromethyl)benzamide To a solution of Example 1A (215 mg, 0.5 mmol) and Example 63A (120 mg, 0.69 mmol) in anhydrous THF (10 mL) at room temperature was added 1N potassium tert-butoxide (0.6 mL, 0.6 mmol) and the mixture was stirred 2 h. Acetic acid was added to pH 6 and the mixture was concentrated under reduced pressure. The residue was dissolved in EtOAc, washed with water, saturated solution of sodium bicarbonate, brine and dried with MgSO$_4$. Purification by chromatography (SiO$_2$, eluted with hexane-EtOAc 1:1) afforded 274 mg of the title compound. $^1$H NMR (300 MHz, DMSO-d$_6$) δ ppm 1.32 (s, 9 H), 1.46-2.03 (m, 13 H), 3.43-3.53 (m, 1 H), 3.61-3.85 (m, 3 H), 4.15-4.34 (m, 3 H), 4.73 (s, 2 H), 5.20 (d, J=3.6 Hz, 1 H), 7.21-7.36 (m, 2 H), 7.76 (dd, J=8.9, 2.2 Hz, 1 H), 8.00 (d, J=2.0 Hz, 1 H). MS (DCI/NH$_3$) m/z 584 (M+H)$^+$.

Example 64

N-[(2Z)-5-tert-butyl-3-[(2R)-tetrahydrofuran-2-ylmethyl]-1,3-thiazol-2(3H)-ylidene]-2-f {(2R)-3-hydroxy-2-[(trifluoroacetyl)amino]propyl}oxy)-5-(trifluoromethyl)benzamide The title compound was obtained as a side product of the procedure described in Example 69B. $^1$H NMR (300 MHz, DMSO-d$_6$) δ ppm 1.32 (s, 9 H), 1.61-1.90 (m, 4 H), 3.50-3.72 (m, 4 H), 4.13-4.43 (m, 6 H), 5.04 (t, J=5.8 Hz, 1 H), 7.24-7.39 (m, 2 H), 7.79 (dd, J=8.7, 2.4 Hz, 1 H), 8.10 (d, J=2.4 Hz, 1 H), 9.39 (d, J=6.3 Hz, 1 H). MS (DCI/NH$_3$) m/z 598 (M+H)$^+$.

Example 65

2-[(tert-butylamino)oxy]-N-[(2Z)-5-tert-butyl-3-[(2R)-tetrahydrofuran-2-ylmethyl]-1,3-thiazol-2(3H)-ylidene]-5-(trifluoromethyl)benzamide The title compound was prepared as described in Example 63B substituting N-tert-butylhydroxylamine hydrochloride for Example 63A. $^1$H NMR (300 MHz, DMSO-D$_6$) δ ppm 1.11 (s, 9 H), 1.28-1.35 (m, 9 H), 1.54-1.70 (m, 1 H), 1.72-2.01 (m, 3 H), 3.58-3.70 (m, 1 H), 3.73-3.86 (m, 1 H), 4.16-4.35 (m, 3 H), 7.26 (d, J=5.1 Hz, 2 H), 7.65-7.81 (m, 2H), 8.01 (d, J=2.4 Hz, 1 H). MS (DCI/NH$_3$) m/z 500 (M+H)$^+$. Anal. calculated for C$_{24}$H$_{32}$F$_3$N$_3$O$_3$S: C, 57.70 H, 6.46 N, 8.41. Found: C, 57.95 H, 6.66 N, 8.31.

Example 66

N-[(2Z)-5-tert-butyl-3-[(2R)-tetrahydrofuran-2-ylmethyl]-1,3-thiazol-2(3H)-ylidene]-2-[(2S)-morpholin-2-ylmethoxy]-5-(trifluoromethyl)benzamide

Example 66A

The title compound was prepared as described in Example 32A substituting (S)-4-(tert-butoxycarbonyl)morpholine-2-carboxylic acid for 4-benzylmorpholine-2-carboxylic acid. MS (DCI/NH$_3$) m/z 218 (M+H)$^+$.

Example 66B tert-butyl (2S)-2-{[2-({[(2Z)-5-tert-butyl-3-[(2R)-tetrahydrofuran-2-ylmethyl]-1,3-thiazol-2(3H)-ylidene]amino}carbonyl)-4-(trifluoromethyl)phenoxy]methyl}morpholine-4-carboxylate The title compound was prepared as described in Example 63B substituting Example 66A for Example 63A. MS (DCI/NH$_3$) m/z 628 (M+H)$^+$.

Example 66C

N-[(2Z)-5-tert-butyl-3-[(2R)-tetrahydrofuran-2-ylmethyl]-1,3-thiazol-2(3H)-ylidene]-2-[2S)-morpholin-2-ylmethoxy]-5-(trifluoromethyl)benzamide A solution of Example 66B (100 mg, 0.16 mmol) in anhydrous $CH_2Cl_2$ (10 mL) was treated with trifluoroacetic acid (0.06 mL, 0.8 mmol) and stirred for 2 hours at room temperature. The mixture was then concentrated under reduced pressure, the residue was treated with saturated solution of $NaHCO_3$ and extracted with EtOAc. The organic extract was washed with brine, dried with $MgSO_4$, filtered, and concentrated under reduced pressure. The residue was purified by chromatography ($SiO_2$, eluted with $CH_2Cl_2$-MeOH 9:1) to afford 60 mg of the title compound. $^1$H NMR (300 MHz, DMSO-$d_6$) δ ppm 1.29-1.37 (m, 9 H), 1.57-1.72 (m, J=7.5 Hz, 1 H), 1.75-1.93 (m, 3 H), 2.85-3.11 (m, 2 H), 3.61-3.71 (m, 2H), 3.73-3.85 (m, 2 H), 3.90-4.08 (m, 3 H), 4.12-4.38 (m, 6 H), 7.26-7.36 (m, 2 H), 7.78 (dd, J=8.6, 2.5 Hz, 1 H), 8.11 (d, J=2.4 Hz, 1 H). MS (DCI/$NH_3$) m/z 528 (M+H)$^+$. Anal. calculated for $C_{25}H_{32}F_3N_3O_4S.0.6H_2O$: C, 55.77 H, 6.22 N, 7.80. Found: C, 55.46 H, 6.34 N, 7.52.

Example 67

N-[(2Z)-5-tert-butyl-3-[(2R)-tetrahydro furan-2-ylmethyl]-1,3-thiazol-2(3H)-ylidene]-2-[(1-methyl-1H-imidazol-5-yl)methoxy]-5-(trifluoromethyl)benzamide The title compound was prepared as described in Example 2A, substituting (S)-tert-butyl 2-(hydroxymethyl)azetidine-1-carboxylate with (1-methyl-1H-imidazol-5-yl)methanol. $^1$H NMR (300 MHz, DMSO-$d_6$) δ ppm 1.31 (s, 9 H), 1.45-1.65 (m, 1 H), 1.67-1.93 (m, 3H), 3.54-3.70 (m, 4 H), 3.69-3.86 (m, 1 H), 4.03-4.30 (m, 3 H), 5.26 (s, 2 H), 7.04 (s, 1H), 7.24 (s, 1 H), 7.47 (d, J=8.5 Hz, 1 H), 7.64 (s, 1 H), 7.78 (dd, J=8.6, 1.9 Hz, 1 H), 8.01 (d, J=2.0 Hz, 1 H). MS (DCI/$NH_3$) m/z 523 (M+H)$^+$. Anal. calcd for $0.5H_2O.C_{24}H_{27}F_3N_4O_3S$: C, 56.48; H, 5.69; N, 10.54. Found: C, 56.16; H, 5.41; N, 10.54.

Example 68

N-[(2Z)-5-tert-butyl-3-[(2R)-tetrahydro furan-2-ylmethyl]-1,3-thiazol-2(3H)-ylidene]-2-[(1-methyl-1H-imidazol-4-yl)methoxy]-5-(trifluoromethyl)benzamide The title compound was prepared as described in example 2A substituting (5)-tert-butyl 2-(hydroxymethyl)azetidine-1-carboxylate with (1-methyl-1H-imidazol-4-yl)methanol. $^1$H NMR (300 MHz, DMSO-$d_6$) δ ppm 1.31 (s, 9 H), 1.52-1.69 (m, 1 H), 1.69-1.96 (m, 3H), 3.58-3.68 (m, 4 H), 3.70-3.83 (m, 1 H), 4.09-4.20 (m, 2 H), 4.19-4.33 (m, 1 H), 5.06 (s, 2 H), 7.13-7.29 (m, 2 H), 7.44-7.62 (m, 2 H), 7.73 (dd, J=8.8, 2.0 Hz, 1 H), 7.95 (d, J=2.0 Hz, 1 H). MS (DCI/$NH_3$) m/z 523 (M+H)$^+$. Anal. calcd for $0.5H_2O.C_{24}H_{27}F_3N_4O_3S$: C, 56.48; H, 5.69; N, 10.54. Found: C, 56.34; H, 5.36; N, 10.53.

Example 69

2-{[(2R)-2-amino-3-hydroxypropyl]oxy}-N-[(2Z)-5-tert-butyl-3-[(2R)-tetrahydrofuran-2-ylmethyl]-1,3-thiazol-2(3H)-ylidene]-5-(trifluoromethyl)benzamide

Example 69A tert-butyl (1R)-2-{[tert-butyl(dimethyl)silyl]oxy}-1-{[2-({[(2Z)-5-tert-butyl-3-[(2R)-tetrahydrofuran-2-ylmethyl]-1,3-thiazol-2(3H)-ylidene]amino}carbonyl)-4-(trifluoromethyl)phenoxy]methyl}ethylcarbamate The title compound was prepared as described in Example 63B, substituting (R)-tert-butyl 2-{[tert-butyl(dimethyl)silyl]oxy}-1-(hydroxymethyl)ethylcarbamate for Example 63A. MS (DCI/$NH_3$) m/z 716 (M+H)$^+$.

Example 69B

2-{[(2R)-2-amino-3-hydroxypropyl]oxy}-N-[(2Z)-5-tert-butyl-3-[(2R)-tetrahydrofuran-2-ylmethyl]-1,3-thiazol-2(3H)-ylidene]-5-(trifluoromethyl)benzamide A solution of Example 69A (500 mg, 0.7 mmol) in $CH_2Cl_2$ (10 mL) at 0° C. was treated with trifluoroacetic acid (0.27 mL, 3.5 mmol). The mixture was allowed to warm to room temperature and stirred for 3 hours. The mixture was concentrated under reduced pressure, diluted with saturated $NaHCO_3$ and extracted with EtOAc. The organic layer was washed with brine, dried with $MgSO_4$, filtered, and concentrated under reduced pressure. Purification by chromatography ($SiO_2$, eluted with $CH_2Cl_2$-MeOH: 6:1) afforded 260 mg of the title compound. $^1$H NMR (300 MHz, DMSO-$d_6$) δ ppm 1.33 (s, 9 H), 1.58-1.73 (m, 1H), 1.75-2.04 (m, 3 H), 2.25-2.43 (m, 1 H), 3.08 (q, J=5.6 Hz, 1 H), 3.36-3.53 (m, 3 H), 3.59-3.69 (m, 1 H), 3.74-3.86 (m, 1 H), 3.94-4.01 (m, 1 H), 4.05-4.12 (m, 1 H), 4.19-4.36 (m, 3 H), 4.68 (t, J=5.2 Hz, 1 H), 7.24-7.34 (m, 2 H), 7.76 (dd, J=8.9, 2.2 Hz, 1 H), 8.07 (d, J=2.4 Hz, 1 H); MS (DCI/$NH_3$) m/z 502 (M+H)$^+$. Anal calculated for $C_{23}H_{30}F_3N_3O_4S.0.75H_2O$: C, 53.63; H, 6.16; N, 8.16. Found: C, 53.40; H, 6.06; N, 8.16.

Example 70

N-[(2Z)-5-tert-butyl-3-[(2R)-tetrahydrofuran-2-ylmethyl]-1,3-thiazol-2(3H)-ylidene]-2-{[(2Z)-2-(hydroxyimino)-3,3-dimethylbutyl]oxy}-5-(trifluoromethyl)benzamide A solution of Example 72 (220 mg, 0.42 mmol) in pyridine (10 mL) was treated with hydroxylamine hydrochloride (32 mg, 0.46 mmol) at room temperature for 24 hours. The mixture was concentrated under reduced pressure and the residue was dissolved in ethyl acetate and washed with water and brine respectively. The ethyl acetate was removed under reduced pressure and the residue was purified by chromatography ($SiO_2$, hexane-EtOAc: 2:1) to afford the title compound and Example 71. $^1$H NMR (300 MHz, DMSO-$d_6$) δ ppm 1.11 (s, 9 H), 1.32 (s, 9 H), 1.56-1.67 (m, 1 H), 1.77-1.91 (m, 3 H), 3.58-3.83 (m, 2 H), 4.13-4.31 (m, 3 H), 4.93 (s, 2 H), 7.24 (s, 1 H), 7.34 (d, J=8.5 Hz, 1 H), 7.75 (dd, J=8.8, 2.0 Hz, 1 H), 7.90 (d, J=2.0 Hz, 1 H), 11.09 (s, 1 H). MS (DCI/$NH_3$) m/z 542 (M+H)$^+$. Anal calculated for $C_{26}H_{34}F_3N_3O_4S$: C, 57.66; H, 6.33; N, 7.76. Found: C, 57.54; H, 6.27; N, 7.52.

Example 71

N-[(2Z)-5-tert-butyl-3-[(2R)-tetrahydrofuran-2-ylmethyl]-1,3-thiazol-2(3H)-ylidene]-2-{[(2E)-2-(hydroxyimino)-3,3-dimethylbutyl]oxy}-5-(trifluoromethyl)benzamide The title compound was isolated as a second product of reaction described in Example 70. $^1$H NMR (300 MHz, DMSO-$d_6$) δ ppm 1.19-1.23 (m, 9 H), 1.31 (s, 9 H), 1.56-1.68 (m, 1 H), 1.70-1.89 (m, 3 H), 3.64 (d, J=8.1 Hz, 1 H), 3.69-3.83 (m, 1 H), 4.12-4.29 (m, 3 H), 4.67 (s, 2 H), 7.19-7.37 (m, 2 H), 7.73 (dd, J=8.6, 1.9 Hz, 1 H), 7.89 (d, J=2.0 Hz, 1 H), 11.00 (s, 1 H). MS (DCI/NH$_3$) m/z 542 (M+H)$^+$. Anal calculated for $C_{26}H_{34}F_3N_3O_4S$: C, 57.66; H, 6.33; N, 7.76. Found: C, 57.45; H, 6.51; N, 7.30.

Example 72

N-[(2Z)-5-tert-butyl-3-[(2R)-tetrahydrofuran-2-ylmethyl]-1,3-thiazol-2(3H)-ylidene]-2-(3,3-dimethyl-2-oxobutoxy)-5-(trifluoromethyl)benzamide A mixture of (R,Z)-N-(5-tert-butyl-3-((tetrahydrofuran-2-yl)methyl)thiazol-2(3H)-ylidene)-2-hydroxy-5-(trifluoromethyl)benzamide (isolated as a byproduct from Example 62B; MS (DCI/NH$_3$) m/z 429 (M+H)$^+$) (330 mg, 0.77 mmol), 1-bromo-3,3-dimethylbutan-2-one (165 mg, 0.92 mmol) and potassium carbonate (106 mg, 0.77 mmol) in acetone (20 mL) was warmed to reflux for 36 hours and then concentrated under reduced pressure. The residue was partitioned between ethyl acetate and water. The acetate layer was washed with brine, dried with MgSO$_4$, filtered, and concentrated under reduced pressure. The residue was purified by chromatography (SiO$_2$, eluted with hexane-EtOAc: 2:1) to afford 255 mg of the title product. $^1$H NMR (300 MHz, DMSO-$d_6$) δ ppm 1.15-1.20 (m, 9 H), 1.32 (s, 9 H), 1.59-1.70 (m, 1 H), 1.74-2.00 (m, 3 H), 3.61-3.69 (m, 1 H), 3.71-3.84 (m, 1 H), 4.14-4.37 (m, 3 H), 5.30 (s, 2 H), 6.99 (d, J=8.7 Hz, 1 H), 7.26 (s, 1 H), 7.69 (dd, J=8.9, 2.2 Hz, 1 H), 7.97 (d, J=2.8 Hz, 1 H). MS (DCI/NH$_3$) m/z 527 (M+H)$^+$. Anal calculated for $C_{26}H_{33}F_3N_2O_4S$: C, 59.30; H, 6.32; N, 5.32. Found: C, 59.27; H, 6.59; N, 5.34.

Example 73

N-[(2Z)-5-tert-butyl-3-[(2R)-tetrahydrofuran-2-ylmethyl]-1,3-thiazol-2(3H)-ylidene]-2-{[2-(hydroxyimino)propyl]oxy}-5-(trifluoromethyl)benzamide A solution of Example 63B (250 mg, 0.43 mmol) in methanol (10 mL) was treated with p-toluenesulfonic acid (81 mg, 0.43 mmol) at room temperature for 4 days. The mixture was concentrated under reduced pressure, diluted with saturated NaHCO$_3$, and extracted with ethyl acetate. The organic extract was washed with brine, dried with MgSO$_4$, filtered, and concentrated under reduced pressure. Purification by chromatography (SiO$_2$, eluted with hexane-EtOAc 1:1) afforded 180 mg of the title compound. $^1$H NMR (300 MHz, DMSO-$d_6$) δ ppm 1.30 (s, 9 H), 1.56-1.67 (m, 1 H), 1.77-1.91 (m, 6 H), 3.58-3.83 (m, 2 H), 4.13-4.31 (m, 3 H), 4.73 (s, 2 H), 7.24 (s, 1 H), 7.30 (d, J=8.5 Hz, 1 H), 7.75 (dd, J=8.8, 2.0 Hz, 1H), 8.00 (d, J=2.0 Hz, 1 H), 11.00 (s, 1 H). MS (DCI/NH$_3$) m/z 500 (M+H)$^+$. Anal calculated for $C_{23}H_{28}F_3N_3O_4S$.2.5H$_2$O: C, 50.99; H, 5.33; N, 7.39. Found: C, 50.73; H, 6.11; N, 7.72.

Example 74

N-[(2Z)-5-tert-butyl-3-[(2R)-tetrahydrofuran-2-ylmethyl]-1,3-thiazol-2(3H)-ylidene]-2-[2-methyl-2-(1H-pyrrol-1-yl)propoxy]-5-(trifluoromethyl)benzamide The title compound was prepared as described in Example 63B substituting 2-methyl-2-(1H-pyrrol-1-yl)propan-1-ol for Example 63A. Purification by chromatography (SiO$_2$, eluted with hexane-Et$_2$O: 2:1) afforded 190 mg of the title compound. $^1$H NMR (300 MHz, DMSO-$d_6$) δ ppm 1.34 (s, 9 H), 1.56-1.67 (m, 7 H), 1.75-1.92 (m, 3 H), 3.66 (t, J=7.5 Hz, 1 H), 3.73-3.83 (m, 1 H), 4.13 (s, 2 H), 4.18-4.31 (m, 3 H), 5.90 (t, J=2.2 Hz, 2 H), 6.97 (t, J=2.2 Hz, 2 H), 7.18 (d, J=8.7 Hz, 1 H), 7.27 (s, 1 H), 7.71 (dd, J=8.7, 2.4 Hz, 1 H), 7.99 (d, J=2.4 Hz, 1 H). MS (DCI/NH$_3$) m/z 550 (M+H)$^+$.

Example 75

2-[(acetylamino)oxy]-N-[(2Z)-5-tert-butyl-3-[(2R)-tetrahydrofuran-2-ylmethyl]-1,3-thiazol-2(3H)-ylidene]-5-(trifluoromethyl)benzamide To a mixture of Example 1A (150 mg, 0.35 mmol) and N-hydroxyacetamide (52.3 mg, 0.70 mmol) in THF (10 mL) was added sodium tert-butoxide (67.0 mg, 0.70 mmol). The mixture was stirred at room temperature for 6 hours. The reaction mixture was diluted with ether and washed with brine. The aqueous phase was extracted with ether (2×20 mL), dried over MgSO$_4$, and filtered. The mixture was concentrated under reduced pressure and the residue was purified by FC on SiO$_2$ using an Analogix® Intelliflash280™ (eluted with Hexanes-EtOAc: 0-30%) to give the title compound. $^1$H NMR (300 MHz, CDCl$_3$) δ ppm 1.19 (s, 9 H), 1.21 (m, 1 H), 1.37 (s, 1 H), 1.94 (s, 2 H), 1.97-2.11 (m, 1 H), 3.65-3.92 (m, 2 H), 3.99-4.33 (m, 2 H), 4.34-4.55 (m, 1 H), 6.82 (s, 1 H), 7.66 (dd, J=9.2, 2.4 Hz, 1 H), 8.34 (d, J=8.8 Hz, 1 H), 8.61 (d, J=2.4 Hz, 1 H); MS (ESI) m/z 486 (M+H)$^+$.

Example 76

2-[(tert-butylamino)oxy]-N-[(2Z)-5-tert-butyl-3-(2-methoxyethyl)-1,3-thiazol-2(3H)-ylidene]-5-(trifluoromethyl)benzamide The title compound was prepared as described in Example 63B substituting Example 1A with Example 41A and substituting N-tert-butylhydroxylamine hydrochloride for Example 63A. $^1$H NMR (300 MHz, DMSO-$d_6$) δ ppm 1.12 (s, 9 H), 1.28-1.36 (m, 9 H), 3.21-3.30 (m, 3 H), 3.71 (t, J=5.4 Hz, 2 H), 4.35 (t, J=5.6 Hz, 2 H), 7.17-7.32 (m, 2 H), 7.63-7.84 (m, 2 H), 8.01 (d, J=2.4 Hz, 1 H). MS (DCI/NH$_3$) m/z 474 (M+H)$^+$. Anal. calcd for 0.5H$_2$O.C$_{22}$H$_{30}$F$_3$N$_3$O$_3$S: C, 55.80; H, 6.39; N, 8.87. Found: C, 55.86; H, 6.51; N, 8.51.

Example 77

N-[(2Z)-5-tert-butyl-3-[(2R)-tetrahydrofuran-2-ylmethyl]-1,3-thiazol-2(3H)-ylidene]-2-({(2S)-1-[2-(hydroxyimino)propyl]pyrrolidin-2-yl}methoxy)-5-(trifluoromethyl)benzamide

Example 77A

N-[(2Z)-5-tert-butyl-3-[(2R)-tetrahydrofuran-2-ylmethyl]-1,3-thiazol-2(3H)-ylidene]-2-{[(2S)-1-(2-oxopropyl)pyrrolidin-2-yl]methoxy}-5-(trifluoromethyl)benzamide The title compound was prepared as described in Example 22C, substituting (S)-1-(2-(hydroxymethyl)pyrrolidin-1-yl)propan-2-one for (R)-(tetrahydrofuran-2-yl)methanol. MS (DCI/NH$_3$) m/z 568 (M+H)$^+$.

Example 77B

N-[(2Z)-5-tert-butyl-3-[(2R)-tetrahydrofuran-2-ylmethyl]-1,3-thiazol-2(3H)-ylidene]-2-({(2S)-1-[2-(hydroxyimino)propyl]pyrrolidin-2-yl}methoxy)-5-(trifluoromethyl)benzamide The title compound was prepared as described in Example 70 substituting Example 72 with Example 77A. $^1$H NMR (300 MHz, DMSO-d$_6$) δ ppm 1.25-1.40 (m, 9 H), 1.50-2.04 (m, 11 H), 2.22 (q, J=8.2 Hz, 1 H), 2.73-3.01 (m, 3 H), 3.54-3.87 (m, 3 H), 3.88-4.11 (m, 2 H), 4.11-4.38 (m, 3 H), 7.16-7.39 (m, 2 H), 7.74 (dd, J=8.7, 2.8 Hz, 1 H), 7.93 (d, J=2.4 Hz, 1 H), 10.25-10.50 (m, 1 H) MS (DCI/NH$_3$) m/z 583 (M+H)$^+$. Anal. calcd for 0.5H$_2$O.C$_{28}$H$_{37}$F$_3$N$_4$O$_4$S: C, 57.72; H, 6.40; N, 9.62. Found: C, 57.39; H, 6.43; H, 9.20.

Example 78

N-[(2Z)-5-tert-butyl-3-[(2R)-tetrahydrofuran-2-ylmethyl]-1,3-thiazol-2(3H)-ylidene]-2-[(diethylamino)oxy]-5-(trifluoromethyl)benzamide The title compound was prepared as described in Example 63B substituting N,N-diethylhydroxylamine for Example 63A. Purification by chromatography (SiO$_2$, eluted with hexane-Et$_2$O: 7:3) afforded 120 mg of the title compound. $^1$H NMR (300 MHz, DMSO-d$_6$) δ ppm 1.06 (t, J=7.5 Hz, 6 H), 1.31-1.36 (m, 9 H), 1.61-1.72 (m, 1 H), 1.76-1.99 (m, 3 H), 2.87-3.06 (m, J=6.8 Hz, 4 H), 3.66 (t, J=7.5 Hz, 1 H), 3.74-3.87 (m, 1 H), 4.16-4.38 (m, 3H), 7.26 (s, 1 H), 7.65-7.82 (m, 2 H), 8.00 (d, J=2.4 Hz, 1 H). MS (DCI/NH$_3$) m/z 500 (M+H)$^+$. Anal calculated for C$_{24}$H$_{32}$F$_3$N$_3$O$_3$S: C, 57.70; H, 6.46; N, 8.41. Found: C, 57.44; H, 6.64; N, 8.05.

Example 79

N-[(2Z)-5-tert-butyl-3-[(2R)-tetrahydrofuran-2-ylmethyl]-1,3-thiazol-2(3H)-ylidene]-2-[(isopropylamino)oxy]-5-(trifluoromethyl)benzamide The title compound was prepared as described in Example 63B substituting N-isopropylhydroxylamine for Example 63A. $^1$H NMR (300 MHz, DMSO-d$_6$) δ ppm 1.05 (d, J=6.3 Hz, 6 H), 1.32 (s, 9 H), 1.60-1.70 (m, 1 H), 1.76-2.00 (m, 3 H), 3.25-3.30 (m, J=6.3 Hz, 1 H), 3.59-3.70 (m, 1 H), 3.74-3.85 (m, 1 H), 4.19-4.36 (m, 3 H), 7.26 (s, 1 H), 7.55 (d, J=5.6 Hz, 1 H), 7.68-7.81 (m, 2 H), 8.02 (d, J=2.4 Hz, 1 H). MS (DCI/NH$_3$) m/z 486 (M+H)$^+$. Anal calculated for C$_{23}$H$_{30}$F$_3$N$_3$O$_3$S: C, 56.89; H, 6.23; N, 8.65. Found: C, 56.88; H, 6.13; N, 8.24.

Example 80

N-[(2Z)-5-tert-butyl-3-[(2R)-tetrahydrofuran-2-ylmethyl]-1,3-thiazol-2(3H)-ylidene]-5-(trifluoromethyl)-2-({[2,2,2-trifluoro-1-methylethylidene]amino}oxy)benzamide The title compound was prepared as described in Example 1B substituting (E)-1,1,1-trifluoropropan-2-one oxime for (R)-tert-butyl 2-(hydroxymethyl)azetidine-1-carboxylate. $^1$H NMR (300 MHz, CDCl$_3$) δ ppm 1.37 (s, 9 H), 1.60-2.17 (m, 4 H), 2.36 (s, 3 H), 3.73-3.91 (m, 2 H), 4.14-4.23 (m, 1 H), 4.23-4.36 (m, 1 H), 4.44 (dd, J=13.56, 2.71 Hz, 1 H), 6.88 (s, 1 H), 7.65-7.65 (m, 1 H), 7.66 (s, 1 H), 8.34 (s, 1 H); MS (ESI) m/z 538 (M+H)$^+$.

Example 81

N-[(2Z)-5-tert-butyl-3-[(2R)-tetrahydrofuran-2-ylmethyl]-1,3-thiazol-2(3H)-ylidene]-2-{[(2R)-2-hydroxypropyl]oxy}-5-(trifluoromethyl)benzamide The title compound was prepared using the procedure as described in Example 1B substituting (R)-propane-1,2-diol for (R)-tert-butyl 2-(hydroxymethyl)azetidine-1-carboxylate. $^1$H NMR (500 MHz, CDCl$_3$) δ ppm 1.23 (d, J=6.41 Hz, 3 H) 1.36 (s, 9 H) 1.66 (dd, J=12.51, 7.93 Hz, 1 H) 1.78-1.84 (m, 1 H) 1.86-1.94 (m, 1 H) 1.98-2.13 (m, 1 H) 3.76-3.80 (m, 1 H) 3.80-3.91 (m, 2 H) 4.17-4.26 (m, 2 H) 4.29 (dd, J=6.71, 2.75 Hz, 1 H) 4.35 (dd, J=9.46, 2.44 Hz, 1 H) 4.41-4.51 (m, 1 H) 6.90 (s, 1 H) 7.08 (d, J=8.54 Hz, 1 H) 7.62 (dd, J=8.54, 2.14 Hz, 1 H) 8.26 (d, J=1.83 Hz, 1 H); MS (DCI/NH$_3$) m/z 487 (M+H)$^+$.

Example 82

2-{[2-tert-butoxyimino)propyl]oxy}-N-[(2Z)-5-tert-butyl-3-[(2R)-tetrahydrofuran-2-ylmethyl]-1,3-thiazol-2(3H)-ylidene]-5-(trifluoromethyl)benzamide

Example 82A

A mixture of 1-hydroxypropan-2-one (0.74 g, 10 mmol) and O-tert-butylhydroxylamine hydrochloride (1.38 g, 11 mmol) in pyridine (10 mL) was stirred at room temperature for 8 hours. The mixture was concentrated under reduced pressure and the residue was partitioned between ethyl acetate and water. The acetate layer was washed with water, brine, dried with MgSO$_4$, filtered, and concentrated under reduced pressure. The residue was purified by chromatography (SiO$_2$, eluted with hexane-Et$_2$O 1:1) to afford 650 mg of the title compound. $^1$H NMR (300 MHz, DMSO-d$_6$) δ ppm 1.21 (s, 9 H), 1.76 (s, 3 H), 3.89 (d, J=5.9 Hz, 2 H), 5.04 (t, 1 H). MS (DCI/NH$_3$) m/z 146 (M+H)$^+$.

Example 82B

2-{[2-tert-butoxyimino)propyl]oxy}-N-[(2Z)-5-tert-butyl-3-[(2R)-tetrahydrofuran-2-ylmethyl]-1,3-thiazol-2(3H)-ylidene]-5-(trifluoromethyl)benzamide The title compound was prepared as described in Example 63B by substituting Example 82A for Example 63A. $^1$H NMR (300 MHz, DMSO-D$_6$) δ ppm 1.23 (s, 9 H), 1.31-1.35

(m, 9 H), 1.58-1.69 (m, 1 H), 1.75-1.94 (m, 6 H), 3.59-3.70 (m, 1 H), 3.74-3.85 (m, 1 H), 4.16-4.35 (m, 3 H), 4.72 (s, 2 H), 7.23-7.36 (m, 2 H), 7.73 (dd, J=8.8, 2.0 Hz, 1 H), 7.99 (d, J=2.7 Hz, 1 H). MS (DCI/NH$_3$) m/z 556 (M+H)$^+$. Anal calculated for $C_{27}H_{36}F_3N_3O_4S$: C, 58.36; H, 6.53; N, 7.56. Found: C, 58.40; H, 6.41; N, 7.08.

Example 83

N-[(2Z)-5-tert-butyl-3-(2R)-(tetrahydrofuran-2-ylmethyl)-1,3-thiazol-2(3H)-ylidene]-2-[(cyclopentylideneamino)oxy]-5-(trifluoromethyl)benzamide The title compound was prepared as described in Example 1B substituting cyclopentanone oxime for (R)-tert-butyl 2-(hydroxymethyl)azetidine-1-carboxylate. $^1$H NMR (300 MHz, DMSO-d$_6$) δ ppm 1.33 (s, 9 H), 1.60-1.98 (m, 8 H), 2.62 (t, J=7.34 Hz, 2H), 3.28-3.33 (m, 2 H), 3.59-3.86 (m, 2 H), 4.18-4.36 (m, 3 H), 7.28 (s, 1 H), 7.57-7.66 (m, 1 H), 7.72-7.79 (m, 1 H), 8.13 (d, J=2.38 Hz, 1 H); MS (ESI) m/z 510 (M+H)$^+$.

Example 84

N-[(2Z)-5-tert-butyl-3-[(2R)-tetrahydrofuran-2-ylmethyl]-1,3-thiazol-2(3H)-ylidene]-2-({[1-methyl-2-oxopropylidene]amino}oxy)-5-(trifluoromethyl) benzamide The title compound was prepared as described in Example 1B substituting (E)-3-(hydroxyimino)butan-2-one for (R)-tert-butyl 2-(hydroxymethyl)azetidine-1-carboxylate. $^1$H NMR (300 MHz, DMSO-d$_6$) δ ppm 1.30-1.35 (m, 9 H), 1.58-1.71 (m, 1 H), 1.74-1.97 (m, 3 H), 2.13 (s, 3 H), 2.43 (s, 3 H), 3.58-3.70 (m, 1 H), 3.72-3.84 (m, 1 H), 4.15-4.36 (m, 3H), 7.30 (s, 1 H), 7.75-7.92 (m, 2 H), 8.21 (d, J=2.37 Hz, 1 H);), MS (ESI) m/z 512 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The invention claimed is:
1. A compound according to formula (I),

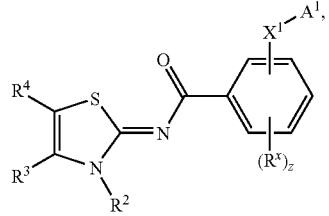

(I)

or a pharmaceutically acceptable salt thereof, wherein
$X^1$ is O, S, S(O), S(O)$_2$, or N(R$^{bx}$); wherein R$^{bx}$ is hydrogen, alkyl, haloalkyl, alkoxyalkyl, —C(O)O(alkyl), monocyclic cycloalkyl, —(CR$^{1c}$ R$^{1d}$)$_{q3}$-(monocyclic cycloalkyl), or haloalkoxyalkyl; and $A^1$ is -G$^{1a}$-G$^{1b}$, —(CR$^{1a}$ R$^{1b}$)$_{q1}$-G$^{1c}$, —(CR$^{1a}$ R$^{1b}$)$_{q1}$-A$^2$, —(CR$^{1g}$R$^{1h}$)$_{q2}$-A$^4$, —N(R$^b$)C(O)R$^a$, —N(R$^b$)C(O)OR$^d$, —N(R$^b$)C(O)N(R$^b$)(R$^c$), —N(R$^b$)(R$^c$), or —N═C(R$^p$)(R$^q$); or $X^1$ and $A^1$ together is N═N(R$^{cx}$); wherein R$^{cx}$ is alkyl, haloalkyl, —(CR$^{1a}$R$^{1b}$)$_{q3}$-A$^3$, G$^{1d}$, or —(CR$^{1a}$R$^{1b}$)$_{q3}$-G$^{1d}$;

R$^p$ is hydrogen, alkyl, haloalkyl, —(CR$^{1a}$R$^{1b}$)$_{q3}$-A$^3$, —C(O)OR$^d$, —C(O)R$^d$, G$^{1d}$, or —(CR$^{1a}$R$^{1b}$)$_{q3}$-G$^{1d}$;

R$^q$ is hydrogen, alkyl, haloalkyl, —N(R$^b$)(R$^c$), —(CR$^{1a}$R$^{1b}$)$_{q3}$-A$^3$, G$^{1d}$, or —(CR$^{1a}$R$^{1b}$)$_{q3}$-G$^{1d}$; or R$^p$ and R$^q$, together with the carbon atom to which they are attached, form a monocyclic 5-, 6-, 7-, or 8-membered cycloalkyl or heterocycle ring, optionally substituted with 1, 2, 3, 4, or 5 substituents independently selected from the group consisting of oxo, alkyl, haloalkyl, and halogen;

$A^2$ is —C(O)R$^a$, —S(O)$_2$R$^d$, —C(O)N(R$^b$)(R$^c$), —C(S)N(R$^b$)(R$^c$), —S(O)$_2$N(R$^b$)(R$^c$), —C(═NOR$^f$)R$^a$, —CN, —N(R$^c$)C(O)R$^m$, —N(R$^c$)C(O)OR$^d$, —N(R$^c$)S(O)$_2$R$^d$, —N(R$^c$)C(O)N(R$^b$)(R$^c$); —N(R$^c$)S(O)$_2$N(R$^b$)(R$^c$), -L$^1$-G$^{1d}$, -L$^1$—(CR$^{1a}$R$^{1b}$)$_{q3}$-G$^{1d}$, -L$^1$—(CR$^{1a}$R$^{1b}$)$_{q1}$-A$^3$, —O—(CR$^{1a}$R$^{1b}$)$_{q2}$—O—alkyl, —OH, or —O(haloalkyl);

$A^3$ is C(O)R$^h$, —S(O)$_2$R$^e$, —C(O)N(R$^h$)$_2$, —C(S)N(R$^h$)$_2$, —S(O)$_2$N(R$^h$)$_2$, —C(═NOR$^h$)R$^h$, —N(R$^h$)C(O)R$^h$, —N(R$^h$)C(O)OR$^e$, —N(R$^h$)S(O)$_2$R$^e$, —N(R$^h$)C(O)N(R$^h$)$_2$, —N(R$^h$)S(O)$_2$N(R$^h$)$_2$, —CN, —OR$^j$, or —N(R$^h$)$_2$;

$A^4$ is cycloalkyl, alkoxy, or N(R$^{1m}$)$_2$;

$L^1$ is O or N(R$^b$);

$R^a$ and $R^c$, at each occurrence, are each independently hydrogen, alkyl, haloalkyl, —(CR$^{1a}$R$^{1b}$)$_{q3}$—O—alkyl, —(CR$^{1a}$R$^{1b}$)$_{q3}$-A$^3$, G$^{1d}$ or —(CR$^{1a}$R$^{1b}$)$_{q3}$-G$^{1d}$;

$R^b$, at each occurrence, is each independently hydrogen, alkyl, haloalkyl, alkoxyalkyl, cycloalkyl, —(CR$^{1c}$R$^{1d}$)$_{q3}$-(cycloalkyl), or haloalkoxyalkyl;

$R^d$, at each occurrence, is alkyl, haloalkyl, —(CR$^{1a}$R$^{1b}$)$_{q3}$—O-alkyl, —(CR$^{1a}$R$^{1b}$)$_{q3}$-A$^3$, G$^{1d}$, or —(CR$^{1a}$R$^{1b}$)$_{q3}$-G$^{1d}$;

$R^j$ is hydrogen, $C_1$-$C_4$ haloalkyl, monocyclic cycloalkyl, or —(CR$^{1c}$R$^{1d}$)$_{q3}$-(monocyclic cycloalkyl);

$R^m$ is haloalkyl, —(CR$^{1a}$R$^{1b}$)$_{q3}$—O-alkyl, —(CR$^{1a}$R$^{1b}$)$_{q3}$-A$^3$, G$^{1d}$, or —(CR$^{1a}$R$^{1b}$)$_{q3}$-G$^{1d}$;

R$^{1b}$, at each occurrence, is independently hydrogen, halo, $C_1$-$C_4$ alkyl, $C_1$-$C_4$ haloalkyl, —OR$^h$, —N(R$^h$)$_2$, —N(R$^h$)C(O)R$^h$, —N(R$^h$)C(O)OR$^e$, or —N(R$^h$)S(O)$_2$R$^e$;

R$^{1g}$, at each occurrence, is independently hydrogen, halo, $C_1$-$C_4$ alkyl, $C_1$-$C_4$ haloalkyl, —OR$^h$, —N(R$^h$)$_2$, —N(R$^h$)C(O)R$^h$, —N(R$^h$)C(O)OR$^e$, or —N(R$^h$)S(O)$_2$R$^e$; provided that at least one occurrence of R$^{1g}$ is halo, $C_1$-$C_4$ haloalkyl, —OR$^h$, —N(R$^h$)$_2$, —N(R$^h$)C(O)R$^h$, —N(R$^h$)C(O)OR$^e$, or —N(R$^h$)S(O)$_2$R$^e$;

R$^{1m}$ is hydrogen, alkyl, haloalkyl, alkylcarbonyl, formyl, or alkoxyalkyl; or two R$^{1m}$ taken together with the nitrogen atom to which they are attached form a heterocyclic ring, optionally substituted with 1, 2, 3, or 4 substituents selected from alkyl, hydroxy, oxo and haloalkyl;

G$^{1a}$ and G$^{1b}$, are each independently cycloalkyl, cycloalkenyl, heterocycle, aryl, or heteroaryl;

G$^{1c}$ is cycloalkenyl, heterocycle, aryl, or heteroaryl;

wherein the ring as represented by G$^{1a}$ is optionally substituted with 1, 2, 3, 4, or 5 substituents independently selected from the group consisting of alkyl, alkenyl, alkynyl, halo, haloalkyl, =N—CN, =N—OR$^f$, —CN, oxo, —OR$^f$, —OC(O)R$^f$, —OC(O)N(R$^f$)$_2$, —S(O)$_2$R$^e$, —S(O)$_2$N(R$^f$)$_2$, —C(O)R$^f$, —C(O)OR$^f$, —C(O)N(R$^f$)$_2$, —N(R$^f$)$_2$, —N(R$^f$)C(O)R$^f$, —N(R$^f$)S(O)$_2$R$^e$, —N(R$^f$)C(O)O(R$^e$), and —N(R$^f$)C(O)N(R$^f$)$_2$;

wherein the cycloalkyl of A$^4$ and the rings as represented by G$^{1b}$ and G$^{1c}$, are each optionally substituted with 1, 2, 3, 4, or 5 substituents independently selected from the group consisting of G$^{1d}$, —(CR$^{1c}$R$^{1d}$)$_{q3}$-G$^{1d}$, alkyl, alkenyl, alkynyl, halo, haloalkyl, =N—CN, —CN, oxo, —OR$^f$, —OC(O)R$^f$, —OC(O)N(R$^f$)$_2$, —S(O)$_2$R$^e$, —S(O)$_2$N(R$^f$)$_2$, —C(O)R$^f$, —C(O)OR$^f$, —C(O)N(R$^f$)$_2$, —N(R$^f$)$_2$, —N(R$^f$)C(O)R$^f$, —N(R$^f$)S(O)$_2$R$^e$, —N(R$^f$)C(O)O(R$^e$), —N(R$^f$)(R$^f$)C(O)N(R$^f$)$_2$, —(CR$^{1c}$R$^{1d}$)$_{q3}$—C(=NOR$^f$)(R$^a$), —(CR$^{1c}$R$^{1d}$)$_{q3}$—OR$^f$, —(CR$^{1c}$R$^{1d}$)$_{q3}$—OC(O)R$^f$, —(CR$^{1c}$R$^{1d}$)$_{q3}$—OC(O)N(R$^f$)$_2$, —(CR$^{1c}$R$^{1d}$)$_{q3}$—S(O)$_2$R$^e$, —(CR$^{1c}$R$^{1d}$)$_{q3}$—S(O)$_2$N(R$^f$)$_2$, —(CR$^{1c}$R$^{1d}$)$_{q3}$—C(O)R$^f$, —(CR$^{1c}$R$^{1d}$)$_{q3}$—C(O)OR$^f$, —(CR$^{1c}$R$^{1d}$)$_{q3}$—C(O)N(R$^f$)$_2$, —(CR$^{1c}$R$^{1d}$)$_{q3}$—N(R$^f$)$_2$, —(CR$^{1c}$R$^{1d}$)$_{q3}$—N(R$^f$)C(O)R$^f$, —(CR$^{1c}$R$^{1d}$)$_{q3}$—N(R$^f$)S(O)$_2$R$^e$, —(CR$^{1c}$R$^{1d}$)$_{q3}$—N(R$^f$)C(O)(R$^e$), —(CR$^{1c}$R$^{1d}$)$_{q3}$—N(R$^f$)C(O)N(R$^f$)$_2$, and —(CR$^{1c}$R$^{1d}$)$_{q3}$—CN;

G$^{1d}$, at each occurrence, is independently a monocyclic heterocycle, a monocyclic heteroaryl, a phenyl, a monocyclic cycloalkyl, or a monocyclic cycloalkenyl; optionally substituted with 1, 2, 3, or 4 substituents selected from the group consisting of —N(R$^h$)$_2$, —CN, oxo, alkyl, haloalkyl, alkoxy, haloalkoxy, halo, and hydroxy;

R$_e$ and R$^i$, at each occurrence, are each independently C$_1$-C$_4$ alkyl, C$_1$-C$_4$ haloalkyl, monocyclic cycloalkyl, or —(CR$^{1c}$R$^{1d}$)$_3$-(monocyclic cycloalkyl);

R$^f$, at each occurrence, is independently hydrogen, C$_1$-C$_4$ alkyl, C$_1$-C$_4$ haloalkyl, —(CR$^{1c}$R$^{1d}$)$_{q3}$—OR$^g$, monocyclic cycloalkyl, monocyclic heterocycle, or —(CR$^{1c}$R$^{1d}$)$_{q3}$-(monocyclic cycloalkyl);

R$^g$ and R$^h$, at each occurrence, are each independently hydrogen, C$_1$-C$_4$ alkyl, C$_1$-C$_4$ haloalkyl, monocyclic cycloalkyl, or —(CR$^{1c}$R$^{1d}$)$_{q3}$-(monocyclic cycloalkyl);

wherein the cycloalkyl, the monocyclic cycloalkyl, and the monocyclic heterocycle, as a substituent or part of a substituent, of R$^b$, R$^{bx}$, R$^e$, R$^i$, R$^f$, R$^g$, R$^h$, and R$^j$, at each occurrence, are each independently unsubstituted or substituted with 1, 2, 3, or 4 substituents selected from the group consisting of C$_1$-C$_4$ alkyl, halo, hydroxy, C$_1$-C$_4$ alkoxy, C$_1$-C$_4$ haloalkoxy, and C$_1$-C$_4$ haloalkyl;

R$^2$ is —(CR$^{2a}$R$^{2b}$)$_{q5}$-G$^2$;

G$^2$ is a 4-, 5-, 6-, 7-, 8-, or 9-membered monocyclic heterocycle containing zero or one double bond, one or two oxygen, and zero or one nitrogen as ring atoms; two non-adjacent atoms of said heterocycle ring can be optionally linked by an alkenylene bridge of 2, 3, or 4 carbon atoms, or optionally linked by an alkylene bridge of 1, 2, 3, or 4 carbon atoms; or G$^2$ is furanyl, oxazolyl, isoxazolyl, or oxadiazolyl; each ring G$^2$ is optionally fused with a monocyclic ring selected from the group consisting of benzo, cycloalkyl, cycloalkenyl, heterocycle and heteroaryl; and each G$^2$ is independently unsubstituted or substituted with 1, 2, 3, 4, 5, or 6 substituents independently selected from the group consisting of oxo, alkyl, halo, —OH, alkoxy, and haloalkyl;

R$^3$ and R$^4$ are each independently G$^3$, hydrogen, alkyl, alkenyl, alkynyl, —NO$_2$, —CN, halo, —OR$^h$, —N(R$^h$)$_2$, —C(O)R$^h$, —C(O)O(R$^h$), haloalkyl, —(CR$^{3a}$R$^{3b}$)$_{q6}$—OR$^h$, —(CR$^{3a}$R$^{3b}$)$_{q6}$—N(R$^h$)$_2$, —(CR$^{3a}$R$^{3b}$)$_{q6}$—C(O)R$^h$, or —(CR$^{3a}$R$^{3b}$)C(O)O(R$^h$);

R$^3$ and R$^4$, together with the carbon atoms to which they are attached, optionally form a 4-, 5-, 6-, or 7-membered monocyclic ring that contains zero, one or two additional double bond, zero or one oxygen atom, and zero, one or two nitrogen atom as ring atoms; two non-adjacent atoms of said monocyclic ring can be optionally linked by an alkenylene bridge of 2, 3, or 4 carbon atoms, or optionally linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, —OH, alkoxy, and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl;

G$^3$ is cycloalkyl, cycloalkenyl, aryl, heterocycle, or heteroaryl, each of which is independently unsubstituted or substituted with 1, 2, 3, or 4 substituents selected from the group consisting of C$_1$-C$_4$ alkyl, C$_2$-C$_4$ alkenyl, C$_2$-C$_4$ alkynyl, halo, C$_1$-C$_4$ haloalkyl, =N—CN, =N—OR$^h$, —CN, oxo, —OR$^h$, —OC(O)R$^h$, —OC(O)N(R$^h$)$_2$, —S(O)$_2$R$^i$—S(O)$_2$N (R$^h$)$_2$, —C(O)R$^h$, —C(O)OR$^h$, —C(O)N(R$^h$)$_2$, —N(R$^h$)$_2$, —N(R$^h$)C(O)R$^h$, —N(R$^h$)S(O)$_2$R$^i$, —N(R$^h$)C(O)O(R$^i$), and —N(R$^h$)C(O)N(R$^h$)$_2$;

R$^{1a}$, R$^{1h}$ R$^{1c}$, R$^{1d}$, R$^{2a}$, R$^{2b}$, R$^{2c}$, R$^{2d}$, R$^{3a}$, and R$^{3b}$, at each occurrence, are each independently hydrogen, halo, C$_1$-C$_4$ alkyl, or C$_1$-C$_4$ haloalkyl;

R$^x$, at each occurrence, is independently G$^{1d}$, alkyl, alkenyl, alkynyl, haloalkyl, —CN, —OC(O)R$^f$, —OC(O)N(R$^f$)$_2$, —S(O)$_2$R$^e$, —S(O)$_2$N(R$^f$)$_2$, —C(O)R$^f$, —C(O)OR$^f$, —C(O)N(R$^f$)$_2$, —N(R$^f$)$_2$, —N(R$^f$)C(O)R$^f$, —N(R$^f$)S(O)$_2$R$^e$, —N(R$^f$)C(O)O(R$^e$), —N(R$^f$)C(O)N(R$^f$)$_2$, —(CR$^{1c}$R$^{1d}$)$_{q3}$—OR$^f$, —(CR$^{1c}$R$^{1d}$)$_{q3}$—OC(O)R$^f$, —(CR$^{1c}$R$^{1d}$)$_{q3}$—OC(O)N(R$^f$)$_2$, —(CR$^{1c}$R$^{1d}$)$_{q3}$—S(O)$_2$R$^e$, —(CR$^{1c}$R$^{1d}$)$_{q3}$—S(O)$_2$N(R$^f$)$_2$, —(CR$^{1c}$R$^{1d}$)$_{q3}$—C(O)R$^f$, —(CR$^{1c}$R$^{1d}$)$_{q3}$—C(O)OR$^f$, —(CR$^{1c}$R$^{1d}$)$_{q3}$—C(O)N(R$^f$)$_2$, —(CR$^{1c}$R$^{1d}$)$_{q3}$—N(R$^f$)$_2$, —(CR$^{1c}$R$^{1d}$)$_{q3}$—N(R$^f$)C(O)R$^f$, —(CR$^{1c}$R$^{1d}$)$_{q3}$—N(R$^f$)S(O)$_2$R$^e$, —(CR$^{1c}$R$^{1d}$)$_{q3}$—N(R$^f$)C(O)O(R$^e$), —(CR$^{1c}$R$^{1d}$)$_{q3}$—N(R$^f$)C(O)N(R$^f$)$_2$, or —(CR$^{1c}$R$^{1d}$)$_{q3}$—CN;

q1 is 1, 2, 3, or 4;

q2 and q4, at each occurrence, are each independently 2, 3, 4, or 5;

q3 is 1, 2 or, 3;

q5 and q6, at each occurrence, are each independently 1, 2, 3, 4, 5, or 6; and z is 1, 2, 3, or 4;

with the proviso that (i) when X$^1$ is N(R$^{bx}$) wherein R$^{bx}$ is hydrogen, alkyl, haloalkyl or alkoxyalkyl; and R$_2$ is —(CR$^{2a}$R$^{2b}$)$_{q4}$—OH or —(CR$^{2a}$R$^{2b}$)$_{q4}$—O-alkyl; then A$^1$ is not —(CR$^{1a}$R$^{1b}$)$_{q1}$—OH;

(ii) when X$^1$ is O; and G$^{1b}$ and G$^{1c}$ are heterocycle, then G$^{1b}$ and G$^{1c}$ are each connected to the parent moiety through the ring carbon atom; and (iii) when X$^1$ is S(O)$_2$ and R$^2$ is —(CR$^{2a}$R$^{2b}$)$_{q4}$—O-alkyl; then A$^1$ is not N(H)$_2$, N(alkyl)(H), or N (alkyl)$_2$.

2. The compound according to claim 1 or a pharmaceutically acceptable salt thereof, wherein

83

R³ and R⁴ are each independently G³, hydrogen, alkyl, alkenyl, alkynyl, —CN, halo, —OR$^h$, haloalkyl, —(CR$^{3a}$R$^{3b}$)$_{q6}$—OR$^h$, or —(CR$^{3a}$R$^{3b}$)$_{q6}$—N(R$^h$)$_2$.

3. The compound according to claim 2 or a pharmaceutically acceptable salt thereof, wherein
X¹ is O or N(R$^{bx}$); and
A¹ is —(CR$^{1a}$R$^{1b}$)$_{q1}$-G$^{1c}$.

4. The compound according to claim 3 or a pharmaceutically acceptable salt thereof, wherein
G² is a 4-, 5-, 6-, or 7-membered monocyclic heterocycle containing zero or one double bond, one or two oxygen, and zero or one nitrogen as ring atoms; or G² is furanyl, oxazolyl, isoxazolyl, or oxadiazolyl; and each G² is independently unsubstituted or substituted with 1, 2, 3, 4, 5, or 6 substituents independently selected from the group consisting of oxo, alkyl, halo, —OH, alkoxy, and haloalkyl.

5. The compound according to claim 2 or a pharmaceutically acceptable salt thereof, wherein
X¹ is O or N(R$^{bx}$); and
A¹ is —(CR$^{1a}$R$^{1b}$)$_{q1}$-A².

6. The compound according to claim 5 or a pharmaceutically acceptable salt thereof, wherein
G² is a 4-, 5-, 6-, or 7-membered monocyclic heterocycle containing zero or one double bond, one or two oxygen, and zero or one nitrogen as ring atoms; or G² is furanyl, oxazolyl, isoxazolyl, or oxadiazolyl; and each G² is independently unsubstituted or substituted with 1, 2, 3, 4, 5, or 6 substituents independently selected from the group consisting of oxo, alkyl, halo, —OH, alkoxy, and haloalkyl.

7. The compound according to claim 2 or a pharmaceutically acceptable salt, thereof, wherein
X¹ is O or N(R$^{bx}$); and
A¹ is —(CR$^{1a}$R$^{1b}$)$_{q1}$—OH.

8. The compound according to claim 7 or a pharmaceutically acceptable salt thereof, wherein
G² is a 4-, 5-, 6-, or 7-membered monocyclic heterocycle containing zero or one double bond, one or two oxygen, and zero or one nitrogen as ring atoms; or G² is furanyl, oxazolyl, isoxazolyl, or oxadiazolyl; and each G² is independently unsubstituted or substituted with 1, 2, 3, 4, 5, or 6 substituents independently selected from the group consisting of oxo, alkyl, halo, —OH, alkoxy, and haloalkyl.

9. The compound according to claim 2 or a pharmaceutically acceptable salt thereof, wherein
X¹ is O or N(R$^{bx}$); and
A¹ is —N(R$^b$)C(O)R$^a$, —N(R$^b$)C(O)OR$^d$, —N(R$^b$)C(O)N(R$^b$)(R$^c$), —N(R$^b$)(R$^c$), or —N=C(R$^p$)(R$^q$).

10. The compound according to claim 9 or a pharmaceutically acceptable salt thereof, wherein
G² is a 4-, 5-, 6-, or 7-membered monocyclic heterocycle containing zero or one double bond, one or two oxygen, and zero or one nitrogen as ring atoms; or G² is furanyl, oxazolyl, isoxazolyl, or oxadiazolyl; and each G² is independently unsubstituted or substituted with 1, 2, 3, 4, 5, or 6 substituents independently selected from the group consisting of oxo, alkyl, halo, —OH, alkoxy, and haloalkyl.

11. The compound according to claim 2 or a pharmaceutically acceptable salt thereof, wherein
X¹ is O or N(R$^{bx}$); and
A¹ is —N(R$^b$)(R$^c$).

12. The compound according to claim 11 or a pharmaceutically acceptable salt thereof, wherein

84

G² is a 4-, 5-, 6-, or 7-membered monocyclic heterocycle containing zero or one double bond, one or two oxygen, and zero or one nitrogen as ring atoms; or G² is furanyl, oxazolyl, isoxazolyl, or oxadiazolyl; and each G² is independently unsubstituted or substituted with 1, 2, 3, 4, 5, or 6 substituents independently selected from the group consisting of oxo, alkyl, halo, —OH, alkoxy, and haloalkyl.

13. The compound according to claim 1 having formula (II),

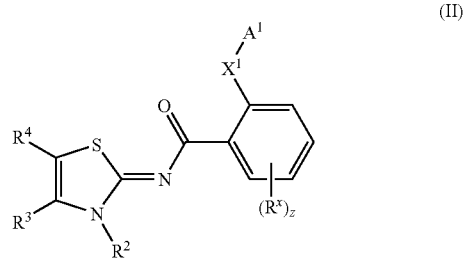

(II)

or a pharmaceutically acceptable salt thereof.

14. The compound according to claim 13 or a pharmaceutically acceptable salt thereof, wherein
X¹ is O or N(R$^{bx}$).

15. The compound according to claim 13 or a pharmaceutically acceptable salt thereof, wherein
X¹ is O or N(R$^{bx}$);
R³ and R⁴ are each independently G³, hydrogen, alkyl, alkenyl, alkynyl, —CN, halo, —OR$^h$, haloalkyl, —(CR$^{3a}$R$^{3b}$)—OR$^h$, or —(CR$^{3a}$R$^{3b}$)—N(R$^h$)$_2$; and
A¹ is —(CR$^{1a}$R$^{1b}$)$_{q1}$-G$^{1c}$, —(CR$^{1a}$R$^{1b}$)$_{q1}$-A², —N(R$^b$)C(O)Ra, —N(R$^b$)C(O)OR$^d$, —N(R$^b$)(R$^c$), or —N=C(R$^p$)(R$^q$).

16. The compound according to claim 15 or a pharmaceutically acceptable salt thereof, wherein
G² is a 4-, 5-, 6-, or 7-membered monocyclic heterocycle containing zero or one double bond, one or two oxygen, and zero or one nitrogen as ring atoms; or G² is furanyl, oxazolyl, isoxazolyl, or oxadiazolyl; and each G² is independently unsubstituted or substituted with 1, 2, 3, 4, 5, or 6 substituents independently selected from the group consisting of oxo, alkyl, halo, —OH, alkoxy, and haloalkyl.

17. The compound according to claim 13 or a pharmaceutically acceptable salt thereof, wherein
X¹ is O or N(R$^{bx}$);
R³ and R⁴ are each independently G³, hydrogen, alkyl, alkenyl, alkynyl, —CN, halo, —OR$^h$, haloalkyl, —(CR$^{3a}$R$^{3b}$)—OR$^h$, or —(CR$^{3a}$R$^{3b}$)—N(R$^h$)$_2$; and
A¹ is —(CR$^{1a}$R$^{1b}$)$_{q1}$—OH.

18. The compound according to claim 17 or a pharmaceutically acceptable salt thereof, wherein
G² is a 4-, 5-, 6-, or 7-membered monocyclic heterocycle containing zero or one double bond, one or two oxygen, and zero or one nitrogen as ring atoms; or G² is furanyl, oxazolyl, isoxazolyl, or oxadiazolyl; and each G² is independently unsubstituted or substituted with 1, 2, 3, 4, 5, or 6 substituents independently selected from the group consisting of oxo, alkyl, halo, —OH, alkoxy, and haloalkyl.

19. The compound according to claim 13 or a pharmaceutically acceptable salt thereof, wherein $X^1$ is O or $N(R^{bx})$;

$R^3$ and $R^4$ are each independently $G^3$, hydrogen, alkyl, alkenyl, alkynyl, —CN, halo, —$OR^h$, haloalkyl, —$(CR^{3a}R^{3b})$—$OR^h$, or —$(CR^{3a}R^{3b})$—$N(R^h)_2$; and $A^1$ is —$N(R^b)(R^c)$.

20. The compound according to claim 19, or a pharmaceutically acceptable salt thereof, wherein $G^2$ is a 4-, 5-, 6-, or 7-membered monocyclic heterocycle containing zero or one double bond, one or two oxygen, and zero or one nitrogen as ring atoms; or $G^2$ is furanyl, oxazolyl, isoxazolyl, or oxadiazolyl; and each $G^2$ is independently unsubstituted or substituted with 1, 2, 3, 4, 5, or 6 substituents independently selected from the group consisting of oxo, alkyl, halo, —OH, alkoxy, and haloalkyl.

21. The compound according to claim 1 selected from the group consisting of

2-[(2R)-azetidin-2-ylmethoxy]-N-[(2Z)-5-tert-butyl-3-[(2R)-tetrahydrofuran-2-ylmethyl]-1,3-thiazol-2(3H)-ylidene]-5-(trifluoromethyl)benzamide;

2-[(2S)-azetidin-2-ylmethoxy]-N-[(2Z)-5-tert-butyl-3-[(2R)-tetrahydrofuran-2-ylmethyl]-1,3-thiazol-2(3H)-ylidene]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S)-1-methylazetidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(2S) -piperidin-2-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S)-1-methylpiperidin-2-yl]methoxy}-5-(trifluoromethyl)benzamide;

N-[(2Z)-5-tert-butyl-3-[(2R)-tetrahydrofuran-2-ylmethyl]- 1,3-thiazol-2(3H)-ylidene]-2-[(2R) -piperidin-2-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2R)-1-methylpiperidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2R)-1-methylazetidin-2-yl]methoxy}-5-(trifluoromethyl)benzamide;

2-(azetidin-3-ylmethoxy) -N-[(2Z)-5-tert-butyl-3-[(2R)-tetrahydrofuran-2-ylmethyl]-1,3-thiazol-2(3H)-ylidene]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(3R) -piperidin-3-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(3R)-1-methylpiperidin-3-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(1-methylazetidin-3-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(3S) -piperidin-3-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(3S)-1-methylpiperidin-3-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(1 -methylpiperidin-4-yl)methoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-(piperidin-4-ylmethoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(1-methyl-1H-imidazol-5-yl)methoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-(pyridin-2-ylmethoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-(pyrazin-2-ylmethoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(1-oxidopyridin-2-yl)methoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-(pyridin-3-ylmethoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(2R) -tetrahydrofuran-2-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(2S) -tetrahydrofuran-2-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S)-1-methylpyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(2R) -pyrrolidin-2-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2R)-1-methylpyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[2-(1-methylpyrrolidin-2-yl)ethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(3R) -pyrrolidin-3-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(3S) -pyrrolidin-3-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(3R)-1-methylpyrrolidin-3-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(3S)-1-methylpyrrolidin-3-yl]methoxy}-5-(trifluoromethyl)benzamide;

2-[(4-benzylmorpholin-2-yl)methoxy]-N-[(2Z)-5-tert-butyl-3-[(2S)-tetrahydrofuran-2-ylmethyl]-1,3-thiazol-2 (3H)-ylidene]-5-(trifluoromethyl)benzamide;

2-{[(2R)-2-amino-3-hydroxypropyl]oxy}-N-[(2Z)-5-tert-butyl-3-[(2S)-tetrahydrofuran-2-ylmethyl]-1,3-thiazol-2(3H)-ylidene]-5-(trifluoromethyl)benzamide;

N-[(2Z)-5-tert-butyl-3-[(2S)-tetrahydrofuran-2-ylmethyl]-1,3-thiazol-2(3H)-ylidene]-2-[(1,4-dimethylpiperazin-2-ylmethyl]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{2-[methyl(phenyl)amino]ethoxy}-5-(trifluoromethyl)benzamide;

2-(benzyloxy)-N-[(2Z)-5-tert-butyl-3-[(2R)-tetrahydrofuran-2-ylmethyl]-1,3-thiazol-2(3H)-ylidene]-5-(trifluoromethyl)benzamide;

N-[(2Z)-5-tert-butyl-3-[(2R)-tetrahydrofuran-2-ylmethyl]-1,3-thiazol-2(3H)-ylidene]-2-(1,3-oxazol-5-ylmethoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-(1,3-thiazol-2-ylmethoxy)-5-(trifluoromethyl)benzamide;

2-(2-tert-butylhydrazino)-N-[(2Z)-5-tert-butyl-3-[(2R)-tetrahydrofuran-2-ylmethyl]-1,3-thiazol-2(3H)-ylidene]-5-(trifluoromethyl)benzamide;

tert-butyl2-[2-({[(2Z)-5-tert-butyl-3-[(2R)-tetrahydrofuran-2-ylmethyl]-1,3-thiazol-2(3H)-ylidene]amino}carbonyl)-4-(trifluoromethyl)phenyl]hydrazinecarboxylate;

N-[(2Z)-5-tert-butyl-3-[(2R)-tetrahydrofuran-2-ylmethyl]-1,3-thiazol-2(3H)-ylidene]-2-{[(2S)-1-methyl-5-oxopyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(2S)-pyrrolidin-2-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S)-1-ethylpyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S)-1-isopropylpyrrolidin-2-yl]methoxy}-5-(trifluoromethyl)benzamide;

2-{[(2S)-1-acetylpyrrolidin-2-yl]methoxy}-N-[(2Z)-5-tert-butyl-3-[(2R)-tetrahydrofuran-2-ylmethyl]-1,3-thiazol-2(3H)-ylidene]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S)-1-(methylsulfonyl)pyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(2R)-(1-methyl-1-oxidopyrrolidin-2-yl)methoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-(3-hydroxy-3-methylbutoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2S,4S)-4-fluoro-1-methylpyrrolidin-2-yl]methoxy}-5-(trifluoromethyl) benzamide;

N-[(2Z)-5-tert-butyl-3-[(2R)-tetrahydrofuran-2-ylmethyl]-1,3-thiazol-2(3H)-ylidene]-2-{[(2S,4R)-4-fluoro-1-methylpyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-({[(2S)-1-methylpyrrolidin-2-yl]methyl}amino)-5-(trifluoromethyl)benzamide;

N-[(2Z)-5-tert-butyl-3-[(2R)-tetrahydrofuran-2-ylmethyl]-1,3-thiazol-2(3H)-ylidene]-2-(1H-pyrazol-5-ylmethoxy)-5-(trifluoromethyl)benzamide;

N-[(2Z)-4-tert-butyl-3-[(2R)-tetrahydrofuran-2-ylmethyl]-1,3-thiazol-2(3H)-ylidene]-2-{[(2S)-1-methylpyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-{2-[(2-hydroxyethyl)amino]ethoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-5-cyano-2-{[(2S)-1-methylpyrrolidin-2-yl]methoxy}benzamide;

N-[(2Z)-4,5-dimethyl-3-[(2R)-tetrahydrofuran-2-ylmethyl]-1,3-thiazol-2(3H)-ylidene]-2-{[(2S)-1-methylpyrrolidin-2-yl]methyoxy}-5-(trifluoromethyl)benzamide;

N-[(2Z)-5-tert-butyl-4-methyl-3-[(2R)-tetrahydrofuran-2-ylmethyl]-1,3-thiazol-2(3H)-ylidene]-2-{[(2S)-1-methylpyrrolidin-2-yl]methoxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(3S)-morpholin-3-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-({2-[(tetrahydro-2H-pyran-2-yloxy)imino]propyl}oxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-({(2R)-3-hydroxy-2-[(trifluoroacetyl)amino]propyl}oxy)-5-(trifluoromethyl)benzamide;

2-[(tert-butylamino)oxy]-N-[(2Z)-5-tert-butyl-3-[(2R)-tetrahydrofuran-2-ylmethyl]-1,3-thiazol-2(3H)-ylidene]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(2S)-morpholin-2-ylmethoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(1-methyl-1H-imidazol-5-yl)methoxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(1-methyl-1H-imidazol-4-yl)methoxy]-5-(trifluoromethyl)benzamide;

2-{[(2R)-2-amino-3-hydroxypropyl]oxy}-N-[(2Z)-5-tert-butyl-3-[(2R)-tetrahydrofuran-2-ylmethyl]-1,3-thiazol-2(3H)-ylidene]-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2Z)-2-(hydroxyimino)-3,3-dimethylbutyl]oxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[(2E)-2-(hydroxyimino)-3,3-dimethylbutyl]oxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-(3,3-dimethyl-2-oxobutoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-{[2-(hydroxyimino)propyl]oxy}-5-(trifluoromethyl)benzamide;

N-[(2Z)-5-tert-butyl-3-[(2R)-tetrahydrofuran-2-ylmethyl]-1,3-thiazol-2(3H)-ylidene]-2-[2-methyl-2-(1H-pyrrol-1-yl)propoxy]-5-(trifluoromethyl)benzamide;

2-[(acetylamino)oxy]-N-[(2Z)-5-tert-butyl-3-[(2R)-tetrahydrofuran-2-ylmethyl]-1,3-thiazol-2(3H)-ylidene]-5-(trifluoromethyl)benzamide;

N-[(2Z)-5-tert-butyl-3-[(2R)-tetrahydrofuran-2-ylmethyl]-1,3-thiazol-2(3H)-ylidene]-2-({(2S)-1-[2-(hydroxyimino)propyl]pyrrolidin-2-yl}methoxy)-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(diethylamino)oxy]-5-(trifluoromethyl)benzamide;

N-[(2Z)-5-tert-butyl-3-[(2R)-tetrahydrofuran-2-ylmethyl]-1,3-thiazol-2(3H)-ylidene]-2-[(isopropylamino)oxy]-5-(trifluoromethyl)benzamide;

N-[(2Z)-5-tert-butyl-3-[(2R)-tetrahydrofuran-2-ylmethyl]-1,3-thiazol-2(3H)-ylidene]-5-(trifluoromethyl)-2-({[2,2,2-trifluoro-1-methylethylidene]amino}oxy)benzamide;

N-[(2Z)-5-tert-butyl-3-[(2R)-tetrahydrofuran-2-ylmethyl]-1,3-thiazol-2(3H)-ylidene]-2-{[(2R)-2-hydroxypropyl]oxy}-5-(trifluoromethyl)benzamide;

2-{[2-(tert-butoxyimino)propyl]oxy}-N-[2Z)-5-tert-butyl-3-[(2R)-tetrahydrofuran-2-ylmethyl]-1,3-thiazol-2(3H)-ylidene]-5-(trifluoromethyl)benzamide;

N-[(2Z)-5-tert-butyl-3-(tetrahydrofuran-2-ylmethyl)-1,3-thiazol-2(3H)-ylidene]-2-[(cyclopentylideneamino)oxy]-5-(trifluoromethyl)benzamide; and N-[(2Z)-5-tert-butyl-3-[(2R)-tetrahydrofuran-2-ylmethyl]-1,3-thiazol-2(3H)-ylidene]-2-({[1-methyl-2-oxopropylidene]amino}oxy)-5-(trifluoromethyl)benzamide;

or a pharmaceutically acceptable salt thereof.

22. A pharmaceutical composition comprising a therapeutically effective amount of a compound of formula (I) according to claim 1 or a pharmaceutically acceptable salt thereof, in combination with a pharmaceutically acceptable carrier.

\* \* \* \* \*